United States Patent
Chien et al.

(10) Patent No.: US 11,628,031 B2
(45) Date of Patent: Apr. 18, 2023

(54) BARRIER DISPENSER AND METHOD OF USING THE SAME

(71) Applicant: Sano Curatio, LLC, Henderson, NV (US)

(72) Inventors: Norman Tien-Yo Chien, Sierra Madre, CA (US); Richard Alan Swartzbaugh, Henderson, NV (US)

(73) Assignee: SANO CURATIO, LLC, Henderson, NV (US)

( * ) Notice: Subject to any disclaimer, the term of this patent is extended or adjusted under 35 U.S.C. 154(b) by 0 days.

(21) Appl. No.: 17/488,057

(22) Filed: Sep. 28, 2021

(65) Prior Publication Data

US 2022/0087767 A1 Mar. 24, 2022

Related U.S. Application Data

(63) Continuation-in-part of application No. 16/992,614, filed on Aug. 13, 2020, now Pat. No. 11,291,518,
(Continued)

(51) Int. Cl.
*A61B 50/30* (2016.01)
*A61B 90/00* (2016.01)
(Continued)

(52) U.S. Cl.
CPC .............. *A61B 50/30* (2016.02); *A61B 90/08* (2016.02); *A61B 7/00* (2013.01); *A61B 7/026* (2013.01);
(Continued)

(58) Field of Classification Search
CPC ..................................................... A61B 50/30
See application file for complete search history.

(56) References Cited

U.S. PATENT DOCUMENTS 4,130,228 A 12/1978 Perrin
4,461,368 A 7/1984 Plourde
(Continued)

FOREIGN PATENT DOCUMENTS

EP 2238909 A1 10/2010
JP 2004329245 A 11/2004
(Continued)

OTHER PUBLICATIONS

Co-pending U.S. Appl. No. 29/809,528, inventors Chien; Norman Tien-Yo et al., filed Sep. 28, 2021.
(Continued)

*Primary Examiner* — Gene O Crawford
*Assistant Examiner* — Ayodeji T Ojofeitimi
(74) *Attorney, Agent, or Firm* — Wilson Sonsini Goodrich & Rosati

(57) ABSTRACT

The present disclosure provides an apparatus comprising a housing with a left side panel, right side panel, and top panel, each of which may comprise a slot. The apparatus may comprise a front panel that is insertable into the slots of the left and right-side panels. The front panel may comprise a recessed region configured to receive a portion of a medical instrument. A source of a barrier material may be supported by the left and right-side panels. The apparatus may comprise a lid cover comprising a roller portion that is insertable into a slot of the top panel. The lid cover may pivot relative to the housing when the roller portion is inserted into the slot of the top panel. The lid cover and the front panel may form a gap through which a portion of the barrier material may extend when the barrier material is dispensed.

22 Claims, 77 Drawing Sheets

Related U.S. Application Data which is a continuation of application No. 16/354,032, filed on Mar. 14, 2019, now Pat. No. 10,743,957, which is a continuation of application No. 15/636,483, filed on Jun. 28, 2017, now Pat. No. 10,271,919.

(60) Provisional application No. 62/460,178, filed on Feb. 17, 2017, provisional application No. 62/436,105, filed on Dec. 19, 2016, provisional application No. 62/355,551, filed on Jun. 28, 2016.

(51) Int. Cl.
    *A61B 7/00*     (2006.01)
    *A61B 46/10*     (2016.01)
    *A61B 7/02*     (2006.01)

(52) U.S. Cl.
    CPC ....... *A61B 46/10* (2016.02); *A61B 2090/0813* (2016.02)

(56) References Cited

U.S. PATENT DOCUMENTS

| | | |
|---|---|---|
| 5,365,023 A | 11/1994 | Lawton |
| 5,424,495 A | 6/1995 | Wurzburger |
| 5,448,025 A | 9/1995 | Stark et al. |
| 5,466,897 A | 11/1995 | Ross et al. |
| 5,486,659 A | 1/1996 | Rosenbush |
| 5,528,004 A | 6/1996 | Wurzburger |
| 5,647,506 A | 7/1997 | Julius |
| 5,686,706 A | 11/1997 | Wurzburger |
| 5,747,751 A | 5/1998 | Weckerle et al. |
| 5,798,489 A | 8/1998 | Gillio |
| 5,808,244 A | 9/1998 | Knight et al. |
| 5,813,992 A | 9/1998 | Henwood |
| 5,892,233 A | 4/1999 | Clement |
| 5,921,941 A | 7/1999 | Longobardo et al. |
| 5,949,032 A | 9/1999 | Wurzburger |
| 6,009,971 A | 1/2000 | Weidman et al. |
| 6,018,835 A | 2/2000 | Schonfeld |
| 6,019,187 A | 2/2000 | Appavu |
| 6,041,889 A | 3/2000 | Stark et al. |
| 6,206,134 B1 | 3/2001 | Stark et al. |
| 6,467,568 B1 | 10/2002 | Kemper |
| 6,499,560 B1 | 12/2002 | Lang et al. |
| 6,520,281 B1 | 2/2003 | Deslauriers et al. |
| 6,575,917 B2 | 6/2003 | Giroux et al. |
| 7,117,971 B1 | 10/2006 | Cornacchia |
| 7,360,625 B2 | 4/2008 | Stickley |
| 7,424,929 B1 | 9/2008 | Martinez |
| 7,469,769 B1 | 12/2008 | Hmayakyan et al. |
| 7,705,325 B2 | 4/2010 | Vestal |
| 7,712,575 B1 | 5/2010 | Moore |
| 7,757,807 B1 | 7/2010 | Martinez |
| D621,504 S | 8/2010 | Martinez |
| 7,823,690 B2 | 11/2010 | Hirsch et al. |
| 7,891,462 B2 | 2/2011 | Hmayakyan et al. |
| 7,921,959 B2 | 4/2011 | Statner et al. |
| 7,942,597 B2 | 5/2011 | Perlman et al. |
| 8,025,120 B2 | 9/2011 | Eddy |
| 8,042,646 B2 | 10/2011 | Gross |
| 8,057,117 B2 | 11/2011 | Perlman et al. |
| 8,387,745 B2 | 3/2013 | Gross |
| 8,393,818 B2 | 3/2013 | Perlman et al. |
| 8,779,385 B2 | 7/2014 | Noori |
| 8,795,438 B2 | 8/2014 | Rubin et al. |
| 8,985,267 B2 | 3/2015 | Fishberger et al. |
| 9,486,287 B2 | 11/2016 | Beebe et al. |
| 9,561,079 B2 | 2/2017 | Perlman et al. |
| 10,271,919 B2 | 4/2019 | Skroski et al. |
| 10,743,957 B2 | 8/2020 | Swartzbaugh et al. |
| 11,291,518 B2 | 4/2022 | Swartzbaugh et al. |
| 2001/0009258 A1 | 7/2001 | Wakayama |
| 2002/0170771 A1 | 11/2002 | Milam et al. |
| 2004/0159561 A1 | 8/2004 | Fellinger |
| 2005/0092765 A1 | 5/2005 | Chasid et al. |
| 2006/0076184 A1 | 4/2006 | Robinson |
| 2006/0147339 A1 | 7/2006 | Hunter et al. |
| 2006/0213920 A1 | 9/2006 | Agarwal et al. |
| 2007/0045039 A1 | 3/2007 | Agahi et al. |
| 2008/0166384 A1 | 7/2008 | Jones |
| 2008/0223867 A1 | 9/2008 | Carr |
| 2008/0230303 A1 | 9/2008 | Weidman |
| 2008/0251313 A1 | 10/2008 | Knight et al. |
| 2008/0257637 A1 | 10/2008 | Miller et al. |
| 2009/0145685 A1 | 6/2009 | Hmayakyan et al. |
| 2010/0116841 A1 | 5/2010 | Perlman et al. |
| 2010/0212995 A1 | 8/2010 | Hmayakyan et al. |
| 2010/0326850 A1 | 12/2010 | Manlapaz |
| 2011/0186590 A1 | 8/2011 | Lee |
| 2012/0051969 A1 | 3/2012 | Nahman et al. |
| 2012/0261593 A1 | 10/2012 | Noori |
| 2012/0318606 A1 | 12/2012 | Wang |
| 2013/0108507 A1 | 5/2013 | Reiseneder et al. |
| 2013/0245677 A1 | 9/2013 | Sargeant et al. |
| 2013/0341223 A1 | 12/2013 | Fong |
| 2014/0319000 A1 | 10/2014 | Fishberger et al. |
| 2015/0014348 A1 | 1/2015 | Tedesco et al. |
| 2015/0327933 A1 | 11/2015 | Perlman |
| 2016/0000508 A1 | 1/2016 | Finn |
| 2016/0045266 A1 | 2/2016 | Deporto et al. |
| 2016/0296199 A1 | 10/2016 | Mukherjee et al. |
| 2016/0338790 A1 | 11/2016 | Krupnick |
| 2017/0020618 A1 | 1/2017 | Lakes |
| 2017/0053076 A1 | 2/2017 | Lulla et al. |
| 2017/0258435 A1 | 9/2017 | Fishberger et al. |
| 2018/0201433 A1 | 7/2018 | Mader et al. |

FOREIGN PATENT DOCUMENTS

| | | |
|---|---|---|
| KR | 20170002815 A | 1/2017 |
| WO | WO-2009151583 A1 | 12/2009 |
| WO | WO-2010031151 A1 | 3/2010 |
| WO | WO-2014186362 A1 | 11/2014 |
| WO | WO-2014204518 A2 | 12/2014 |
| WO | WO-2018005703 A1 | 1/2018 |

OTHER PUBLICATIONS

International search report and written opinion dated Sep. 6, 2017 for PCT Application PCT-US2017039837.
U.S. Appl. No. 16/354,032 Notice of Allowance dated Apr. 30, 2020.
U.S. Appl. No. 15/636,483 Notice of Allowance dated Dec. 14, 2018.
U.S. Appl. No. 15/636,483 Office Action dated May 15, 2018.
U.S. Appl. No. 16/354,032 Office Action dated Oct. 25, 2019.
U.S. Appl. No. 16/992,614 Notice of Allowance dated Dec. 13, 2021.
U.S. Appl. No. 16/992,614 Office Action dated May 13, 2021.
Co-pending U.S. Appl. No. 17/685,276, inventors Swartzbaugh; Richard Alan et al., filed Mar. 2, 2022.

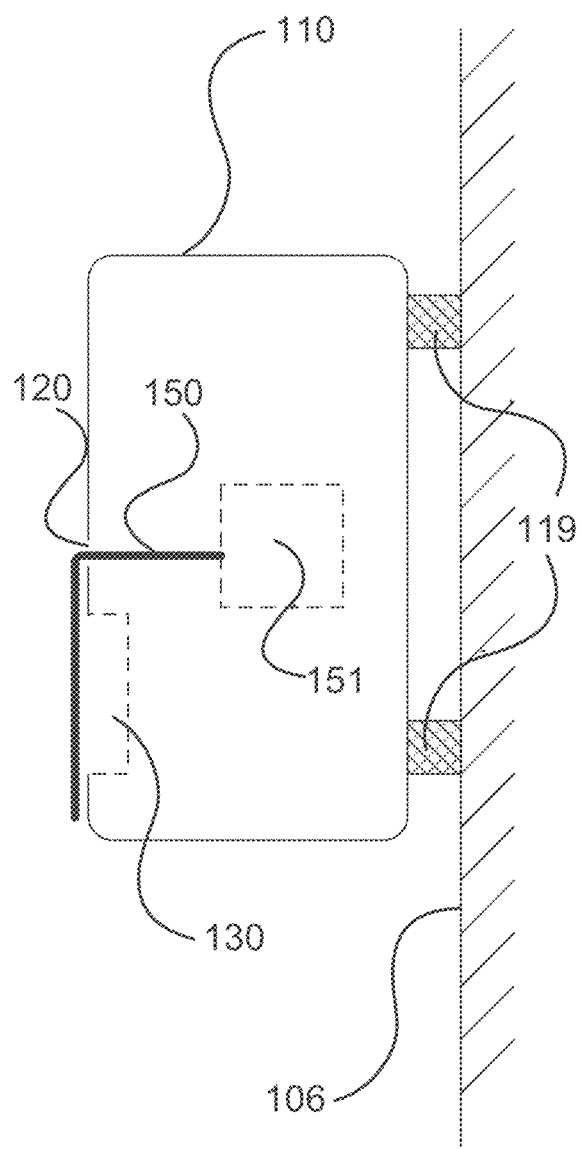
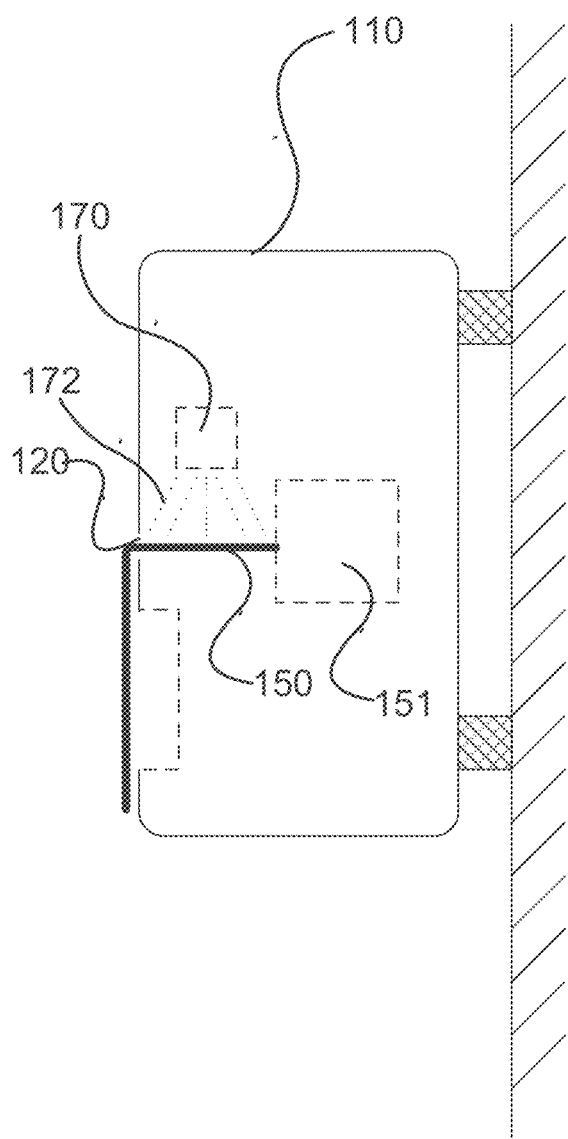
FIG. 2B
FIG. 2C 2600
2600
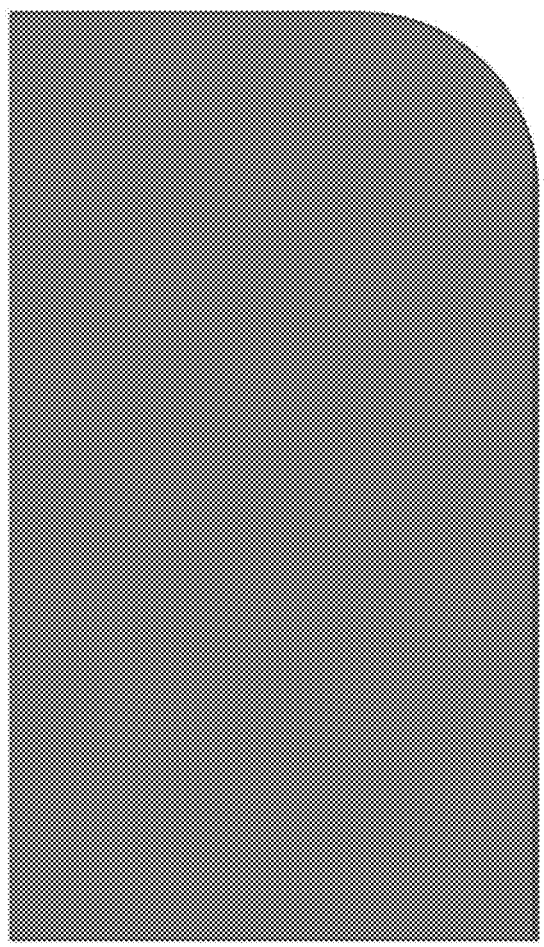
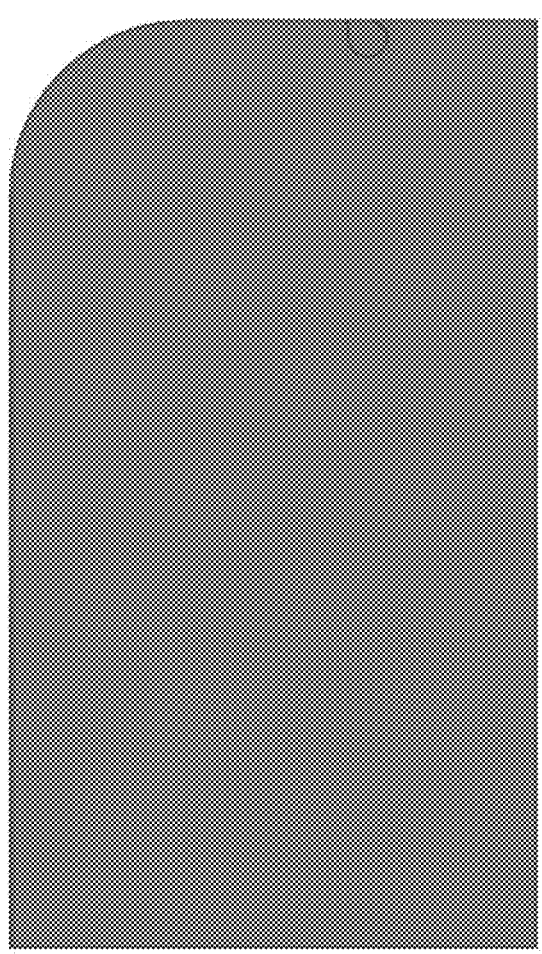
FIG. 28A
FIG. 28B

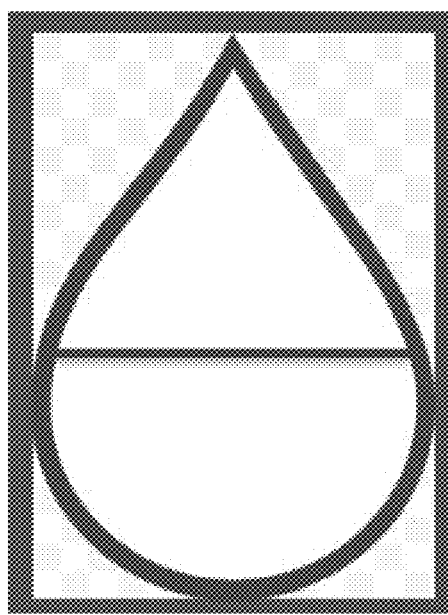
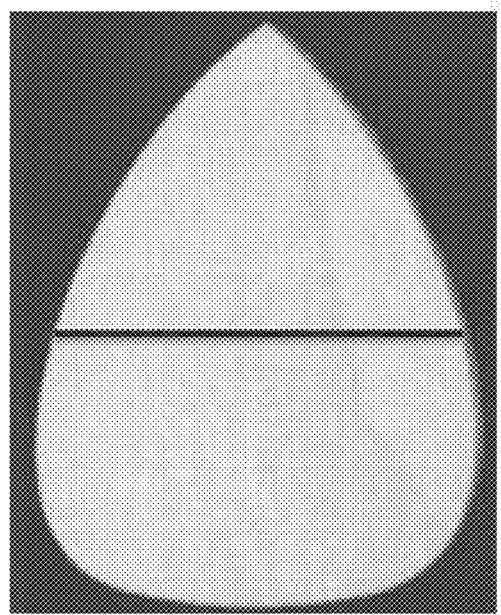
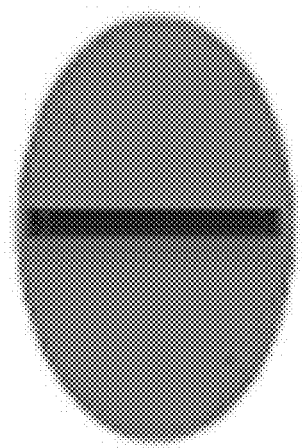
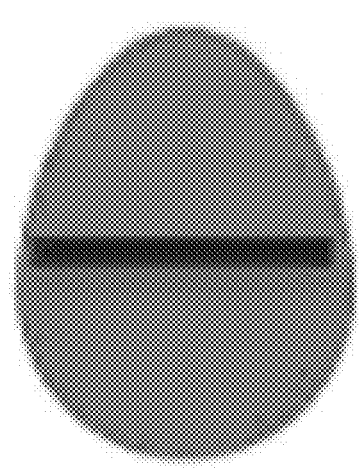
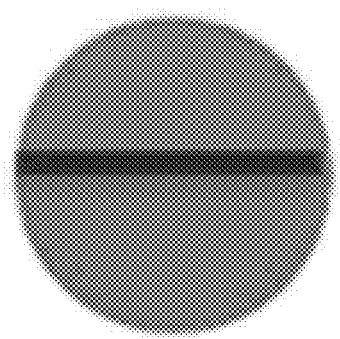
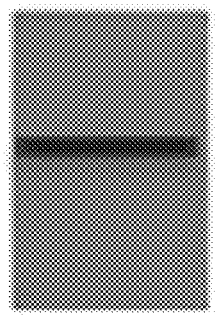
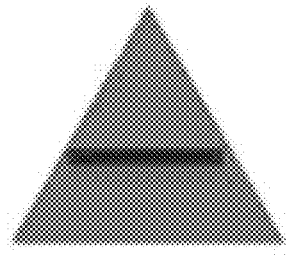
FIG. 47

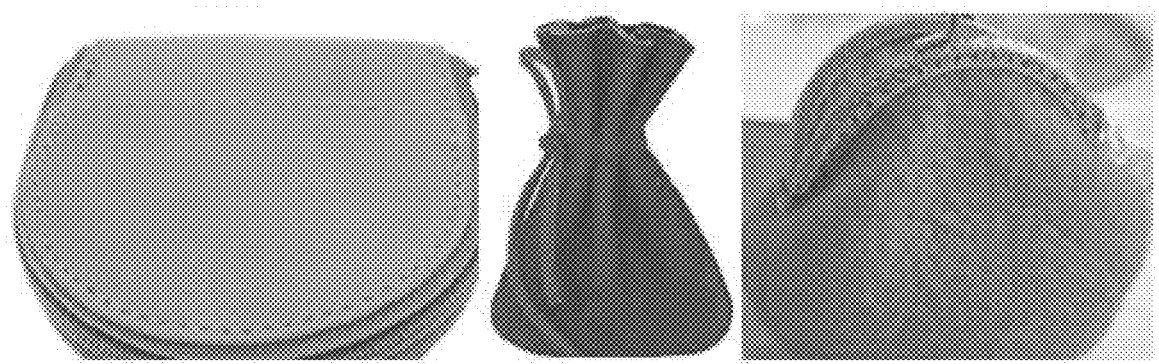
FIG. 49

FIG. S9

BARRIER DISPENSER AND METHOD OF USING THE SAME

CROSS-REFERENCE

This application is a continuation-in-part of U.S. patent application Ser. No. 16/992,614, filed Aug. 13, 2020, now U.S. Pat. No. 11,291,518; which is a continuation of U.S. patent application Ser. No. 16/354,032, filed Mar. 14, 2019, now U.S. Pat. No. 10,743,957; which is a continuation of U.S. patent application Ser. No. 15/636,483, filed on Jun. 28, 2017, now U.S. Pat. No. 10,271,919; which claims the benefit of U.S. Provisional Patent Application No. 62/355,551, filed Jun. 28, 2016; U.S. Provisional Patent Application No. 62/436,105, filed Dec. 19, 2016; and U.S. Provisional Patent Application No. 62/460,178, filed Feb. 17, 2017; each of which is incorporated herein by reference in its entirety for all purposes.

BACKGROUND

Hospital-acquired infections (HAIs) pose a real and monumental threat to the health and life of patients across the healthcare continuum, including acute care hospitals, skilled nursing facilities, and outpatient environments such as primary care physician (PCP) & specialty hospital clinics, surgery centers, occupational health clinics, and physician offices. HAIs are generally acquired from acute & post-acute settings. The Centers for Disease Control (CDC) and Prevention recognize that hospital-acquired infections (HAIs) are one of the major challenges in US hospitals. Transmission of contaminants typically occurs in one out of every 32 patient encounters, and healthcare personnel (doctors, nurses, etc.) are required to clean stethoscopes between patients for 60 seconds. However, studies have shown that more than 95% of healthcare personnel may be non-compliant with the above practice. Thus, a significant need exists for protection from contaminated stethoscopes, which is one of the major contributors to the risk of HAIs to both patients and healthcare personnel. Depending upon the type of disease(s) on a contaminated stethoscope, a waterfall of negative potential outcomes are possible, including, but not limited to injury, illness, syndrome, interruption of work, death, reduced quality of life, reduced lifespan(s), increased costs to diagnose, prognose, treat patient(s), with cumulative negative effect(s) upon the Planet, a nation, state, municipality, employer, family, GDP, etc.

SUMMARY

Apparatus and methods for applying protective barriers to medical scopes are provided herein. A medical scope as described herein may include a stethoscope, and may be interchangeably referred to herein as a stethoscope, medical scope, scope, or scopes. The apparatus and methods can be used with scopes of various shapes and/or sizes, and with different types of scopes, including, but not limited to adult stethoscopes, cardiac stethoscopes, electronic stethoscopes, and/or pediatric stethoscopes. The barrier can be used to reduce or eliminate contamination to a stethoscope head or drum, and may be interchangeably referred to herein as film, protective barrier, barrier, shield, or proprietary membrane. The barrier can be used to reduce the risk of microbial, bacterial, viral, disease, or pathogenic transmissions between patients and/or users. The barrier can be an aseptic, antiseptic, antimicrobial, antiviral, antipathogenic, or antibacterial barrier. The barrier can serve as an aseptic, antiseptic, antimicrobial, antiviral, antipathogenic, or antibacterial barrier for the stethoscope head. The barrier may include an antimicrobial, antiviral, antipathogenic, or antibacterial substance that can reduce, neutralize or destroy microbes, organic matter, contain disinfectants, metals, or a combination of both. The barrier can help to reduce or eliminate contamination of the stethoscope head when the stethoscope is being used on multiple patients. The risk of hospital-acquired infections (HAIs) to patients and users (e.g. healthcare personnel) can be significantly reduced, through use of the protective barrier applied using the apparatus and methods described herein. The barrier may be branded by a client utilizing their logo, trademark, "Doing Business As" (DBA), company name, product name, or stock keeping unit (SKU), and also a license to manufacture or distribute under license from a third-party, other holder of intellectual property, or a license to manufacture or distribute from Sano Curatio, LLC, any future parent, sister, daughter, or affiliated entity of San Curatio, LLC or a combination of the same.

According to some aspects of the invention, an apparatus for dispensing a film for use with a medical scope is provided. The apparatus may include a source of film and a housing. The housing may include a chamber configured to receive and support therein the source of film. The housing may also include an opening provided through a wall of the housing, wherein the opening is configured to permit a portion of the film to extend out of the chamber from the opening when the film is dispensed. An additional layer of material may be on top of, and also under the film to facilitate the delivery of the film. The housing may also include a cover so that no film is exposed until use, or may also leave the film exposed until use. The housing may further include a recess provided on the housing and located such that the extended portion of the film is permitted to hang freely in proximity to the recess. Some portions of the film may be affixed using fingertips. The recess is sized to receive a distal portion of the medical scope. The recess is adapted to allow the extended portion of the film to be applied to the distal portion of the medical scope when said distal portion is placed into the recess with the portion of the film located therebetween. The housing may have a cutter. The shield may be affixed using friction, form-fitting, stretching, adhesive, light adhesive, folding, covering, pulling over, applying, sonic, heat, static, static electricity adhesion, or other form(s) of adhesion.

The device may be mounted utilizing an adhesive, screws, nailed, glued, bolts, nuts, snap-on, slide-on, or otherwise vertically affixed to a wall, cubicle, medication cart, nurses' office, inside an ambulance, or any other vertical surface accessible to health care professionals.

Further aspects of the invention provide a method for dispensing a film for use with a medical scope. The method may include providing an apparatus for dispensing the film, wherein the apparatus comprises a chamber configured to receive and support therein a source of film. The method may also include dispensing a portion of the film from an opening provided through a wall of the housing; extending the portion of the film such that the extended portion hangs freely over a recess provided on the housing, wherein the recess is sized to receive a distal portion of the medical scope; placing the distal portion of the medical scope into the recess with the extended portion of the film located therebetween; and applying the extended portion of the film to the distal portion of the medical scope. Some portions of the film may be affixed using fingertips. The method may also include dispensing a portion of the film from an opening provided through a wall of the housing; extending the portion of the film such that the extended portion is suspended over a covered recess provided on the housing, wherein the recess is sized to receive a distal portion of a stethoscope; placing the distal portion of the stethoscope into the recess with the extended portion of the film located therebetween; and applying the extended portion of the film to the distal portion of the stethoscope.

In another aspect, the present disclosure provides an apparatus for dispensing barrier materials. The apparatus may comprise a housing comprising a left side panel, a right-side panel, and a top panel. In some embodiments, the housing may further comprise a back panel comprising one or more holes for fastening the housing to a wall.

In some cases, the left side panel, the right-side panel, and the top panel each comprise one or more slots. In some embodiments, the apparatus may comprise a front panel that is insertable into the one or more slots of the left side panel and the right-side panel. In some cases, the front panel comprises one or more recessed regions sized and shaped to receive a portion of a medical tool or instrument. In some cases, the medical tool or instrument comprises a scope.

In some embodiments, the apparatus may comprise a source of a barrier material that is disposed within the housing and supported by the left side panel and the right-side panel. In some embodiments, at least one of the left side panel, the right-side panel, and the front panel comprises an optically transparent surface for viewing the source of the barrier material. In some cases, the source of the barrier material is provided on a roller. The roller may be supported at each end by one of the left-side panel and the right-side panel.

In some embodiments, the source of the barrier material comprises a roll of the barrier material. In some embodiments, the barrier material comprises an antimicrobial, antiviral, antipathogenic, antiseptic, aseptic, or antibacterial material that is configured to reduce or eliminate contamination of the medical tool or instrument when applied on or around the medical tool or instrument, or any other material of a clean, non-sterile nature.

In some embodiments, the barrier material comprises a plurality of layers. In some embodiments, the barrier material is configured to envelope at least a portion of a tool or instrument such that a plurality of surfaces of the tool or instrument is covered by the barrier material. In some embodiments, the barrier material comprises one or more pouches, pockets, and/or flaps for receiving or covering at least a portion of a tool or instrument. In some embodiments, the barrier material comprises a pouch or pocket on a front side of the barrier material and a half pouch or flap on a back side of the barrier material.

In some embodiments, the apparatus may comprise a lid cover comprising a roller portion that is insertable into the one or more slots of the top panel. In some cases, the lid cover is pivotable relative to the housing when the roller portion is inserted into the one or more slots of the top panel. In some embodiments, the lid cover comprises a curved profile that conforms to a shape or a profile of the left side panel and the right-side panel. In some embodiments, the lid cover and the front panel form a gap through which a portion of the barrier material is permitted to extend when the barrier material is dispensed such that the extended portion of the barrier material hangs freely in proximity to the one or more recessed regions of the front panel. In some embodiments, the apparatus may further comprise a latch mechanism to secure the lid cover in a closed position.

In some embodiments, the left-side panel and the right-side panel comprise one or more curved edges that conform to the curved profile of the lid cover. In some embodiments, the left-side panel and the right-side panel each comprise a spacing sized and shaped to receive the lid cover when the lid cover is in a closed position such that the lid cover lies flush with one or more edges of the left side panel and the right-side panel.

In some embodiments, the front panel comprises a cutter for cutting and releasing the barrier material. In some embodiments, the cutter comprises a slidable cutting edge for cutting or releasing the barrier material when the barrier material is extended below the cutter.

In some embodiments, the one or more recessed regions are adapted to allow the extended portion of the barrier material to be applied to the portion of the medical tool or instrument when the portion of the medical tool or instrument is placed within the one or more recessed regions. In some embodiments, the one or more recessed regions comprise a first recessed region disposed above the cutter and a second recessed region disposed below the cutter. In some embodiments, the one or more recessed regions comprise (i) a first recessed region that is adapted to allow the extended portion of the barrier material to be applied to a first portion of the medical tool or instrument when the barrier material is extended by a first length and (ii) a second recessed region that is adapted to allow the extended portion of the barrier material to be applied to a second portion of the medical tool or instrument when the barrier material is extended by a second length. In some embodiments, the second length is greater than the first length. In some embodiments, the one or more recessed regions comprise two or more recessed regions having different sizes or shapes.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, patent applications, trademarks, copyrights, trade secrets, industrial design(s), design(s), license(s), and any other recognized form(s) of intellectual property mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2B is a schematic cross-sectional side view of the dispenser of FIG. 2A mounted to a vertical surface;

FIG. 2C is a schematic cross-sectional side view of the dispenser of FIG. 2A further comprising a UV light source, or other light source(s), in accordance with an embodiment;

FIGS. 9 through 17 are perspective views showing application of the barrier to the stethoscope head in accordance with the method shown in FIGS. 8A-8F;

FIG. 9 is a perspective view showing a film dispensed from the opening of the dispenser;

FIG. 10 is a perspective view showing a stethoscope head being placed onto the portion of the film in front of the recess;

FIG. 11 is a perspective view showing the stethoscope head being moved from a center of the recess to a first rounded concave lobe;

FIG. 12 is a perspective view showing the stethoscope head being moved from the first rounded concave lobe to a second rounded concave lobe within the recess;

FIG. 13 is a perspective view showing the stethoscope head being moved from the second rounded concave lobe to a third rounded concave lobe within the recess;

FIG. 14 is a perspective view showing the stethoscope head being moved from the third rounded concave lobe back to the first rounded concave lobe within the recess;

FIG. 15 is a perspective view showing the stethoscope head and the film being pulled downwards until the stethoscope head is below the cutting edge;

FIG. 17 is a perspective view showing the barrier as applied to the stethoscope head;

FIGS. 26A-26B, 27A-27B, 28A-28B, and 29A-29B schematically illustrate various examples of barrier dispensers, in accordance with an embodiment;

FIGS. 47-54 schematically illustrate various non-limiting examples of designs for a barrier material that can be dispensed using the barrier dispensers disclosed herein;

DETAILED DESCRIPTION

Figure 1A:
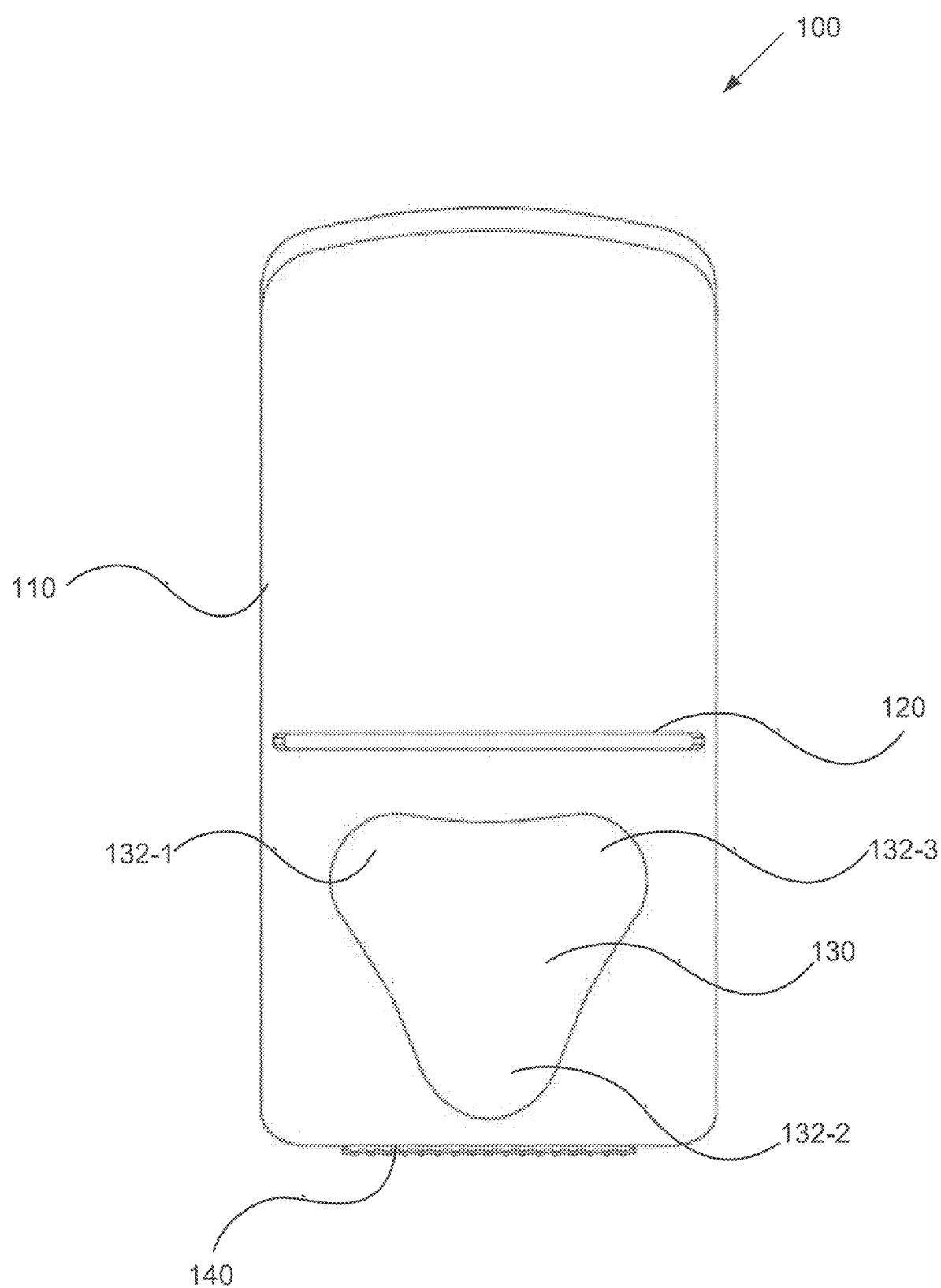
FIG. 1A is a front view of a barrier dispenser in accordance with an embodiment.

While preferred embodiments of the present invention have been shown and described herein, it will be appreciated by those skilled in the art that such embodiments are provided by way of example only. Numerous variations, changes, and substitutions will now occur to those skilled in the art without departing from the invention. It should be understood that various alternatives to the embodiments described herein may be employed in practicing the invention. It is intended that the following claims define the scope of the invention and that methods and structures within the scope of these claims and their equivalents be covered thereby.

The invention provides apparatus and methods for applying a barrier to medical scopes, for example to the drum or head of a stethoscope. The drum or head of the stethoscope may include one or more acoustic sensors. The stethoscope head may be configured to be placed onto a patient's body. The apparatus and methods disclosed herein can be used with scopes of various shapes and/or sizes, and with different types of scopes such as adult stethoscopes and pediatric stethoscopes. The barrier can be clean, non-sterile, antimicrobial, antiviral, powder-free, powdered, aseptic, antiseptic, antipathogenic, sterile, or antibacterial. The barrier can serve as a clean, non-sterile, antimicrobial, antiviral, powder-free, powdered, aseptic, antiseptic, antipathogenic, sterile, or antibacterial barrier for the stethoscope head. The barrier may include a clean, non-sterile, antimicrobial, antiviral, powder-free, powdered, aseptic, antiseptic, antipathogenic or antibacterial substance that can neutralize or destroy microbes, organic matter, contain disinfectants, metals, or a combination of both. The barrier can help to reduce or eliminate contamination of the stethoscope head when the stethoscope is being used on multiple patients. The risk of hospital-acquired infections (HAIs) to patients and healthcare personnel can be significantly reduced, through use of the protective barrier applied using the apparatus and methods described herein. Additionally, the invention does not require complex mechanical systems to apply the barrier, thereby reducing manufacturing, assembly and parts costs. In most cases, the cost of the apparatus and the barrier can be less than $0.15 per use (wholesale cost of goods sold), and can provide an economical solution compared to the use of disinfecting solutions (e.g., for killing pathogens such methicillin-resistant *Staphylococcus aureus* (MRSA) or C Diff *Clostridium difficile*) which generally cost more per unit/gallon. The disclosed apparatus and methods are reliable, robust and can be used for multiple patient encounters over extended periods of time. The apparatus can also be easily assembled and disassembled, and can be used with various types of barrier materials provided in different forms such as films, membranes, rolls, stacked sheets, perforated sheets, wraps, cassette dispensers, etc.

The barrier may comply with a variety of standards (e.g., Modified-Draize-95 Test, ASTM F 1671, ASTM F 1671-13, EN ISO 374-5, ASTM D5151, ASTM D6319, ASTM D7907, AQL 1.5, EN 455-1, EN 455-2, EN 455-3, ASTM D6124-06, PPE (EU) 2016/425, EN 374-2, EN 374-4, EN 420, EN ISO 374-5, ASTM D6978, EC 1935/2004, EU 10/2011, Japan Sanitation Law, 21 CFR 177.2600, ASTM F1671, EN ISO 374-1, ISO 16523-1, ISO 9001, ISO 14001, OHSAS 18001, ISO 13485, EN ISO 13485, EC, JGMP, U.S. FDA, U.S. FDA 510(K), U.S. FDA 510(K) exempt, China FDA, UL Certification, NFPA, ANVISA, ISEGA, PPE Certification(s), ISO 10282, ISO 10993, ISO 10993-1, ISO 10993-5, ISO 10993-10, ISO 10993-11, ISO 16604, Malaysian Rubber Board (MRB) In House Method, European Union MDD 93/42/EEC Annex IX: Class I (Rule 5), European Union MDR 2017/745 Annex VIII Rule 14, point 2 of Article 1 of Directive 2001/83/EC, bacteriological testing, bacteriophage penetration testing, University testing, private lab testing, public lab testing, lab testing, Institutional Review Board (I.R.B.), watertight testing, waterproof testing, water resistant testing, viral penetration testing, protection from penetration by blood-borne pathogens, Phi-X174 virus, Phi-X174 Bacteriophage, Covid, 2019-nCov, SARS-CoV-2, SARS-CoV-2 variants (e.g., Alpha (B.1.1.7), Beta (B.1.351, B.1.351.2, B.1.351.3), Delta (B.1.617.2, AY.1, AY.2, AY.3), Gamma (P.1, P.1.1, P.1.2), Mu (e.g., lineage B.1.621 or VUI-21JUL-1), T951, Y144S, Y145N, R346K, E484K or the escape mutation, N501 V, D614G P681H, and D109N and all future mutations and related strain(s)/virus (es)), *Enterococcus faecalis* (VRE), *Enterococcus faecium*, MRSA, *Staphylococcus aureus*, *Streptococcus pyogenes*, *Escherichia coli*, *Klebsiella pneumoniae*, and other microbe (s).

The barrier material(s) may contain citrus, citrus oil, water-based, alkaline, non-alkaline material, 1,2-Hexanediol, Air, Ammonium bicarbonate, Ammonium carbonate, antimicrobial materials, antiseptic materials, aseptic materials, bleach, chlorine dioxide, citric acid, Dodecylbenzenesulfonic acid, Ethanol (Ethyl alcohol), Ethanol, Glutaraldehyde, Glycolic acid, Hydrochloric acid, Hydrogen chloride, Hydrogen peroxide, Hypochlorous acid, Iodine, Isopropanol (Isopropyl alcohol), lactic acid, L-Lactic acid, Octanoic acid, Octanoic acid, Oxygen, Peracetic acid, Peroxyacetic acid, Peroxyoctanoic acid, Phenolic, PHMB, Potassium peroxymonosulfate, Quaternary ammonium, silver ion, silver, Sodium carbonate peroxyhydrate, Sodium carbonate, Sodium chlorite, Sodium dichloroisocyanurate dihydrate, Sodium dichloroisocyanurate, Sodium hypochlorite, Tetraacetyl ethylenediamine, Thymol, Triethylene glycol, UV, non-leaching antimicrobial materials, leaching antimicrobial materials, photosensitizer, photosensitizer reacting with oxygen in the immediate area to generate singlet oxygen, oxidizers, materials that facilitate photodynamic reactions leading to microbial cell death, and/or materials that facilitate reactions leading to microbial cell death.

The apparatus and methods disclosed herein provide a sanitary, clean (non-sterile), sterile, aseptic, or antiseptic way of applying a barrier to a stethoscope head, thereby reducing or eliminating human contact during application of the barrier. This can help to address the issue of poor stethoscope hygiene. Accordingly, exposure to microbial, viral, pathogenic or bacterial contaminants between patients and healthcare personnel can be largely eliminated, mitigated, or reduced properly using the apparatus, methods, and protocols described herein. The apparatus and methods disclosed herein may be used to complement and/or replace protocols for handling infectious disease(s), stethoscope cleaning, stethoscope care, medical equipment disinfection guidelines, stethoscope disinfection, and stethoscope manufacturer's instructions.

Various aspects of the invention described herein may be applied to any of the particular applications set forth below and for any other types of scopes in addition to stethoscopes. The invention may be used in any system that requires application of a protective barrier to an object. The invention may be applied as a standalone apparatus or method, or as part of a medical system in a healthcare environment. It shall be understood that different aspects of the invention can be appreciated individually, collectively, or in combination with each other.

FIG. 1A is a front view of a barrier dispenser 100 in accordance with an embodiment. A barrier dispenser as described herein may refer to any apparatus, device or system that is designed, configured, or used for applying a barrier to a medical scope such as a stethoscope. The barrier can serve as a protective barrier or shield for the head or drum of the stethoscope. The dispenser can be configured to apply a barrier onto a variety of stethoscopes including adult care stethoscopes, pediatric stethoscopes, cardiology stethoscopes, electronic stethoscopes, Emergency Medical Technicians (EMT)/Emergency Medical Services (EMS) stethoscopes, anesthesiologist stethoscopes, and the like. The dispenser can be used to apply the barrier onto the stethoscopes for different applications including adult cardiac diagnoses, pediatric diagnoses, etc. The dispenser and the barrier can be used in a variety of environments including hospitals, clinics, emergency rooms, patient examination rooms, acute care patient rooms, ambulatory care, pediatrics, field environments, nurse's offices in educational settings, occupational health clinics, surgery or operation rooms, pre-acute settings, acute settings, post-acute settings, places that pose high risk of infection from microbes, viruses, pathogens, germs, diseases, bacteria, etc. The barrier is designed such that it does not interfere with the acoustic detection of the stethoscope. For example, the barrier may be a thin membrane that allows acoustic signals from the body to be transmitted through in an unimpeded manner. In some cases, loss of decibel(s) is not material. The barrier is disposable and designed for use in a single patient encounter. The film may be created through a custom formulation, or utilize "off-the-shelf" materials prepared by other manufacture's customized and/or licensed to this application, thus allowing the customer to customize the attributes of the film based on the healthcare setting, budget, clinical requirements, and other patient & business factors.

The dispenser can be used to apply a barrier to the stethoscope head prior to the stethoscope head contacting the patient's body, so as to reduce or prevent contamination of the stethoscope head or risk of infection to the patient. The barrier may be a thin film or a membrane, and may be made of a polymer such as polyurethane, or any other medical-grade or food-grade plastics. The film may be latex free. Alternatively, the film may comprise latex, plastic, cellophane, vinyl, acetate, polyethylene acrylic, butyl rubber, ethylene-vinyl acetate, natural rubber, a nitrile, nitrile powdered, latex powdered, latex polymer, polymer, polyisoprene powder free, polyisoprene powdered, silicone rubber, Nitrile Clean Room Class 100, Clean Room Class 100, latex powder free chlorinated, colloidal oatmeal, accelerator-free, biodegradable, biocompatible (non-sensitizing & low dermatitis potential, non-toxic, non-cytotoxic, non-irritating, non-sensitizing, sensitizing), metal detectable, surgical, specialty, industrial, commercial, a styrene block copolymer, a vinyl ether, or a tackifier. Antimicrobial, antiseptic, aseptic, antiviral, materials may include but are not limited to: sodium bicarbonate; hydrogen peroxide; benzalkonium chloride; chlorhexidine; hexachlorophene; iodine compounds; and combinations thereof. In some embodiments, the antimicrobial, antiseptic, or aseptic materials may not include alcohols (such as ethanol, 1-propanol and 2-propanol/isopropanol or mixtures of these alcohols), since solvents/alcohols may promote the airborne transmission of certain types of micro-organisms, and certain type of microbes may be resistant to alcohols. For example, certain types of microorganisms (e.g., *Clostridium Difficile* (C. Diff)) can cause spores and facilitate airborne transmission when interacting with solvents. Depending upon the film material and properties selected, the barrier may comply with a variety of standards (e.g., Modified-Draize-95 Test, ASTM F 1671, ASTM F 1671-13, EN ISO 374-5, ASTM D5151, ASTM D6319, ASTM D7907, AQL 1.5, EN 455-1, EN 455-2, EN 455-3, ASTM D6124-06, PPE (EU) 2016/425, EN 374-2, EN 374-4, EN 420, EN ISO 374-5, ASTM D6978, EC 1935/2004, EU 10/2011, Japan Sanitation Law, 21 CFR 177.2600, ASTM F1671, EN ISO 374-1, ISO 16523-1, ISO 9001, ISO 14001, OHSAS 18001, ISO 13485, EN ISO 13485, EC, JGMP, U.S. FDA, U.S. FDA 510(K), U.S FDA 510(K) exempt, China FDA, UL Certification, NFPA, ANVISA, ISEGA, PPE Certification(s), ISO 10282, ISO 10993, ISO 10993-1, ISO 10993-5, ISO 10993-10, ISO 10993-11, ISO 16604, Malaysian Rubber Board (MRB) In House Method, European Union MDD 93/42/EEC Annex IX: Class I (Rule 5), European Union MDR 2017/745 Annex VIII Rule 14, point 2 of Article 1 of Directive 2001/83/EC, bacteriological testing, bacteriophage penetration testing, University testing, private lab testing, public lab testing, lab testing, Institutional Review Board (I.R.B.), watertight testing, waterproof testing, water resistant testing, viral penetration testing, protection from penetration by blood-borne pathogens, Phi-X174 virus, Phi-X174 Bacteriophage, Covid, 2019-nCov, SARS-CoV-2, SARS-CoV-2 variants (e.g.; Alpha (B.1.1.7), Beta (B.1.351, B.1.351.2, B.1.351.3), Delta (B.1.617.2, AY.1, AY.2, AY.3), Gamma (P.1, P.1.1, P.1.2), Mu (e.g., lineage B.1.621 or VUI-21JUL-1), T951, Y144S, Y145N, R346K, E484K or the escape mutation. N501Y, D614G, P681H, and D109N and all future mutations and related strain(s)/virus(es)), *Enterococcus faecalis* (VRE), *Enterococcus faecium*, MRSA, *Staphylococcus aureus*, *Streptococcus pyogenes*, *Escherichia coli*, *Klebsiella pneumoniae*, and other microbe(s). The film may include antimicrobial, antiviral, germicidal, antipathogenic, antiseptic, aseptic, and/or bactericidal properties. The film may or may not include silver, copper, titanium, other metals, formulas, or compounds. The film may also include any other antimicrobial formula, property, surface, or agent that is designed to help reduce concentrations of microbes, viruses, germs, pathogens, microorganisms, disease, microbe-killing, or bacteria on the stethoscope head, including, for example, materials, substances, products, or compounds that are citrus-based, water-based, alkaline, non-alkaline material, 1,2-Hexanediol, Air, Ammonium bicarbonate, Ammonium carbonate, bleach, chlorine dioxide, citric acid, Dodecylbenzenesulfonic acid, Ethanol (Ethyl alcohol), Ethanol, Glutaraldehyde, Glycolic acid, Hydrochloric acid, Hydrogen chloride, Hydrogen peroxide, Hypochlorous acid, Iodine, Isopropanol (Isopropyl alcohol), lactic acid, L-Lactic acid, Octanoic acid, Octanoic acid, Oxygen, Peracetic acid, Peroxyacetic acid, Peroxyoctanoic acid, Phenolic, PHMB, Potassium peroxymonosulfate, Quaternary ammonium, silver ion, silver, Sodium carbonate peroxyhydrate, Sodium carbonate, Sodium chlorite, Sodium dichloroisocyanurate dihydrate, Sodium dichloroisocyanurate, Sodium hypochlorite, Tetraacetyl ethylenediamine, Thymol, Triethylene glycol, UV, non-leaching antimicrobial materials, leaching antimicrobial materials, photosensitizer, photosensitizer reacting with oxygen in the immediate area to generate singlet oxygen, oxidizers, or materials that facilitate photodynamic reactions leading to microbial cell death.

The dispenser can include biologically acceptable materials suitable for medical applications, depending on the particular application and/or preference of a medical practitioner. For example, components of the dispenser can include or be fabricated from materials such as cellophane, vinyl, acetate, polyethylene acrylic, butyl rubber, ethylene-vinyl acetate, natural rubber, a nitrile, nitrile powdered, latex powdered, latex polymer, polymer, polyisoprene powder free, polyisoprene powdered, silicone rubber, Nitrile Clean Room Class 100, Clean Room Class 100, latex powder free chlorinated, colloidal oatmeal, accelerator-free, biodegradable, metal detectable, surgical, specialty, industrial, commercial, non-leaching antimicrobial, leaching antimicrobial, a styrene block copolymer, a vinyl ether, or a tackifier. Antimicrobial and/or antiseptic and/or aseptic materials include but are not limited to: sodium bicarbonate; hydrogen peroxide; benzalkonium chloride; chlorohexidine; hexachlorophene; iodine compounds; combinations thereof; and other formulas and compounds. In some embodiments, the antimicrobial and/or antiseptic and/or aseptic materials may not include alcohols (such as ethanol, 1-propanol and 2-propanol/isopropanol or mixtures of these alcohols), since solvents/alcohols may promote the airborne transmission of certain types of micro-organisms, and certain type of microbes may be resistant to alcohols. For example, certain types of microorganisms (e.g., *Clostridium Difficile* (C. Diff)) can cause spores and facilitate airborne transmission when interacting with solvents.

Antimicrobial materials, antiseptic, aseptic can further include but are not limited to: beta-lactam antibiotics (such as penicillin, cephalosporin); protein synthesis inhibitors (such as aminoglycosides, macrolides, tetracycline, chloramphenicol, polypeptides); sulphonamides; cotrimoxazole; quinolones; anti-viral agents; anti-fungal agents; anti-cancer drugs; anti-malarial drugs; anti-tuberculosis drugs; anti-leprotic drugs; anti-protozoal drugs and combinations thereof.

An antimicrobial, antiseptic, aseptic material may include, for example, a silver-based antimicrobial material, a copper-based antimicrobial material, a titanium-based antimicrobial material, chlorhexidene gluconate, benzalkonium chloride, a monoquaternary and/or polyquaternary ammonium salt-based antimicrobial material, a biguanide-based antimicrobial such as polyhexamethylene biguanide, triclosan, zinc pyridine, an isothiazolinone-based antimicrobial, a 10,10'-oxybisphenoxarsine-based antimicrobial, a peptide-based antimicrobial, a natural antimicrobial such as hops extract, honey, a chitosan-based antimicrobial, and combinations thereof.

Other film materials may be citrus-based, citrus oil, water-based, alkaline, non-alkaline material, 1,2-Hexanediol, Air, Ammonium bicarbonate, Ammonium carbonate, bleach, chlorine dioxide, citric acid, Dodecylbenzenesulfonic acid, Ethanol (Ethyl alcohol), Ethanol, Glutaraldehyde, Glycolic acid, Hydrochloric acid, Hydrogen chloride, Hydrogen peroxide, Hypochlorous acid, Iodine, Isopropanol (Isopropyl alcohol), lactic acid, L-Lactic acid, Octanoic acid, Octanoic acid, Oxygen, Peracetic acid, Peroxyacetic acid, Peroxyoctanoic acid, Phenolic, PHMB, Potassium peroxymonosulfate, Quaternary ammonium, silver ion, silver, Sodium carbonate peroxyhydrate, Sodium carbonate, Sodium chlorite, Sodium dichloroisocyanurate dihydrate, Sodium dichloroisocyanurate, Sodium hypochlorite, Tetraacetyl ethylenediamine, Thymol, Triethylene glycol, UV, non-leaching antimicrobial, leaching antimicrobial, photosensitizer, photosensitizer reacting with oxygen in the immediate area to generate singlet oxygen, oxidizers, photodynamic reactions leading to microbial cell death, antiseptic, aseptic.

Other shield transportation materials (single sheet, top sheet, bottom sheet, and/or top & bottom sheet) may be citrus-based, water-based, alkaline, non-alkaline material, 1,2-Hexanediol, Air, Ammonium bicarbonate, Ammonium carbonate, bleach, chlorine dioxide, citric acid, Dodecylbenzenesulfonic acid, Ethanol (Ethyl alcohol), Ethanol, Glutaraldehyde, Glycolic acid, Hydrochloric acid, Hydrogen chloride, Hydrogen peroxide, Hypochlorous acid, Iodine, Isopropanol (Isopropyl alcohol), lactic acid, L-Lactic acid, Octanoic acid, Octanoic acid, Oxygen, Peracetic acid, Peroxyacetic acid, Peroxyoctanoic acid, Phenolic, PHMB, Potassium peroxymonosulfate, Quaternary ammonium, silver ion, silver, Sodium carbonate peroxyhydrate, Sodium carbonate, Sodium chlorite, Sodium dichloroisocyanurate dihydrate, Sodium dichloroisocyanurate, Sodium hypochlorite, Tetraacetyl ethylenediamine, Thymol, Triethylene glycol, UV, non-leaching antimicrobial, leaching antimicrobial, photosensitizer, photosensitizer reacting with oxygen in the immediate area to generate singlet oxygen, oxidizers, photodynamic reactions leading to microbial cell death, antiseptic, aseptic.

Optionally in any of the embodiments disclosed herein, one or more components of the dispenser can include or be fabricated from materials such as polyvinyl chloride, polyvinylidene chloride, low density polyethylene, linear low density polyethylene, polyisobutene, poly[ethylene-vinylacetate] copolymer, lightweight aluminum foil and combinations thereof, stainless steel alloys, commercially pure titanium, titanium alloys, silver alloys, copper alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of the dispenser may have material composites, including one or more of the above materials, to achieve various desired characteristics such as strength, rigidity, elasticity, compliance, biomechanical performance, durability and/or radiolucency preference. One or more of the components of the dispenser may comprise antimicrobial and/or antiseptic and/or aseptic materials. The components of the dispenser, individually or collectively, may also be fabricated from a heterogeneous material such as a combination of two or more of the above-described materials. The components of the dispenser may be monolithically formed or integrally connected.

It is well-known in the art that certain forms of electromagnetic energy, such as UV light and specifically UV-C, has potent germicidal properties. Optionally, the present disclosure provides methods for sterilizing or disinfecting a film or barrier, including: exposing the film or the barrier to electromagnetic energy having a wavelength preferably between about 100 nm and about 280 nm, more preferably between about 200 nm-280 nm, or even more preferably between about 240 nm-270 nm, where the exposure may result in sanitization or disinfection of the film or barrier, or even sterilization of the film or barrier depending on how much UV energy is applied to the film or barrier.

The barrier that is applied a stethoscope head may be optically translucent, transparent, or branded by client utilizing their logo, trademark, "Doing Business As" (DBA), company name, product name, or stock keeping unit (SKU), or licensed by Sano Curatio, LLC. Alternatively, the barrier may be opaque. The barrier/film may have tensile strength of ranging from about 5 to 30 lbs/in, and an elongation ranging from about 110% to 240%. The barrier may include an anti-microbial, antiviral, antipathogenic, or antibacterial material for reducing the amount of microbes, viruses, pathogens, germs, diseases, or bacteria on the stethoscope head before patient use. The barrier protects the healthcare professional and patient. The antimicrobial, antiviral, germicidal, antipathogenic, antiseptic, aseptic, and/or bactericidal properties may be pre-fabricated into the film/barrier. The antimicrobial, antiviral, germicidal, antipathogenic, antiseptic, aseptic, and/or bactericidal properties may also be applied to the barrier. For example, a material comprising the anti-microbial, antiviral, germicidal, antipathogenic, antiseptic, aseptic, and/or bactericidal properties may be coated or sprayed onto the barrier after the barrier has been applied onto the stethoscope head. Optionally in any of the embodiments disclosed herein, UV/UV-C light may also be applied to the barrier, barrier roll, barrier cassette, or individual barrier sheets. The barrier may include an adhesive for detachably attaching the barrier to the stethoscope head. The adhesive may be a weak adhesive that preferably does not leave a residue on the stethoscope head when removed therefrom. The adhesive may have an adhesion strength that prevents the barrier from peeling or falling off the stethoscope head during use with a patient, but that allows the barrier to be easily and manually removed from the stethoscope head after use (for disposal). Optionally in any of the embodiments disclosed herein, the adhesive may an adhesive or peel strength ranging from about 1 to 20 oz/in. The barrier may comprise a material that is acoustically transmissive and substantially impermeable to microorganisms and fluids. Optionally in any of the embodiments disclosed herein, the barrier may comprise polyvinyl chloride, polyvinylidene chloride, low density polyethylene, linear low-density polyethylene, polyisobutene, polyethylene-vinylacetate copolymer, copper, copper-based, silver, silver-based, lightweight aluminum foil, and/or any combinations thereof.

The dispenser may be rigidly or detachably mounted to any structure. For example, the dispenser can be mounted to the wall of a hospital room, edge of a table, side of a medication cart, interior wall of a medical transport vehicle, cube wall, or any other appropriate vertical surface, in any pre-acute, acute, or post-acute setting, or other setting(s). The dispenser can also be mounted to a vehicle, for example within a compartment or sidewall of an ambulance, emergency vehicle, or air ambulance (helicopter, or plane). Alternatively, a portable, single-use dispenser can be standalone and need not be mounted onto any object. In some cases, the dispenser may be worn or carried by a user, for example on a lab coat, pocket, purse, or on the hip. The dispenser may be portable and configured for use in a variety of environments or applications as described herein. The housing can be configured to support a source of barrier material (e.g., rolled, a roll of film, a cassette of film, stacked, boxed, individual, individually packaged, interleafed-sheets, or individual sheets of film) as described elsewhere herein.

Referring to FIG. 1A, the dispenser 100 may include a housing 110. The housing may be formed to have any shape and/or size. The housing can be configured to support a source of barrier material (e.g., rolled, a roll of film, a cassette of film, stacked, boxed, individual, individually packaged, interleafed-sheets, or individual sheets of film) as described elsewhere herein. Optionally in any of the embodiments disclosed herein, the housing may be a substantially rectangular plastic hollow box. The housing may be, for example approximately 3-6 inches wide, approximately 9-12 inches long, and 3-6 inches deep; the housing may be wider, longer, or deeper. The housing may be configured for mounting on a vertical surface such as, for example, a wall of a room, cube wall, interior of a medical transport, medication cart. Optionally in any of the embodiments disclosed herein, a bracket may be provided that allows the housing to be mounted directly to the vertical surface. The housing may engage the bracket in a manner that affixes the housing relative to the vertical surface. The housing may be formed using any number of techniques known in the art such as injection molding, blow molding, three-dimensional (3D) printing (plastic or metal), etc.

The housing may include a chamber (not shown). The chamber may be configured to receive and support a source of barrier material. The barrier material may include a film, shield, or membrane. Optionally in any of the embodiments disclosed herein, the source may include a source of film for use with a medical scope. The film may be delivered to the healthcare professional sandwiched on a single layer or dual layer material, with the film adhered to one layer, and an optional top layer to help protect the cleanliness of the film. FIGS. 53, 54, and 61-64 show examples of films that are sandwiched between two layers and films with multiple layers. The film may have a thickness ranging from about 10 μm to about 1000 μm. For example, the film may preferably have a thickness from about 10 μm to about 200 μm, and most preferably from about 20 μm to about 30 μm. In some cases, the film may have a thickness less than 10 μm or greater than 1000 μm, or anything in between. Weight (grams) may vary from under 2 grams to more than 6 grams, and anything in between. Thickness (millimeters or mm) may be under 1 mm and more than 8 mm or anything in between. Thickness may be under 0.01 mm and more than 0.10 mm and anything in between. Optionally in any of the embodiments disclosed herein, the film may have a thickness of about 1 mil. The dispenser can be configured to dispense the film to form a barrier on the stethoscope head (using the healthcare professional's gloved hand.) The barrier can be formed by covering the stethoscope head with the film as described later herein. An opening 120 may be provided through a wall of the housing. The opening may be a through-hole that provides access between the chamber of the housing and an external environment. The opening can permit the film to extend out of the chamber when the film is being dispensed. In the example of FIG. 1A, the opening is formed as a slot although the invention is not limited thereto. The opening can be formed having any shape and/or size to accommodate the dimensions of the film and to allow the film to pass through but preferably is sized to accommodate the film width and thickness to allow the film to pass through the slot while minimizing the slot opening thereby helping to prevent dust, particles or other contaminants from entering the housing. In one or more of the embodiments described herein, the opening may be formed having a circular or elliptical shape, and configured to permit separate sheets to be dispensed from a plurality of interleaved stacked sheets.

The housing 100 may further include a recess 130. The recess may be provided on a wall of the housing. As shown in FIG. 1A, the recess is located below the opening although the invention is not limited thereto. In some cases, the recess can be located above the opening or anywhere on the housing. The recess may be formed having any shape, design, depth, and/or size. Examples of possible shapes or designs include but are not limited to: mathematical shapes, two-dimensional geometric shapes, multi-dimensional geometric shapes, curves, polygons, polyhedral, polytopes, minimal surfaces, ruled surfaces, non-orientable surfaces, quadrics, pseudospherical surfaces, algebraic surfaces, miscellaneous surfaces, riemann surfaces, box-drawing characters, cuisenaire rods, geometric shapes, shapes with metaphorical names, symbols, unicode geometric shapes, shapes based on math symbols characters from any language history music art science religion, or any other form. Optionally in any of the embodiments disclosed herein, the recess may have a substantially circular or elliptical shape.

In the example of FIG. 1A, the recess 130 may have a substantially triangular shape, or any other shape. The recess may be symmetrical, for example an equilateral triangle. Alternatively, the recess may have an irregular shape and need not be symmetrical. The recess may have rounded corners. For example, each corner of the recess may be rounded having a radius in a range from about 5 mm to about 50 mm. In some cases, the radius of the corner may be less than 5 mm or greater than 50 mm. Optionally in any of the embodiments disclosed herein, each corner of the recess may include rounded concave lobe. For example, in FIG. 1A, the recess may include a plurality of rounded concave lobes 132 forming the triangular shaped recess. A first lobe 132-1 may be located at the top left corner of the recess, a second lobe 132-2 may be located at the bottom corner of the recess, and a third lobe 132-3 may be located at the top right corner of the recess. The recess may include any number of rounded concave lobes.

The recess 130 can be sized and/or shaped to receive a distal portion of a medical scope, for example the head or drum of a stethoscope. The recess may be formed as a sunken cavity or trench on the wall of the housing. In some cases, the recess may be formed as a molded extrusion into the chamber of the housing. The recess may have a depth ranging from about 2 mm to about 10 mm, or preferably at least deep enough to receive the head or drum of the stethoscope. In some cases, the recess may have a depth that is less than 2 mm or greater than 10 mm.

Optionally in any of the embodiments disclosed herein, the recess may be coated or sprayed with a citrus, citric, oxygen-generating, copper, silver, titanium or other metal (s), coating, or any other antimicrobial material, anti-septic, aseptic, anti-viral material, surfactants or agents that are designed to reduce microorganisms, disease, virus, cellular, bacteria, or airborne or surface particulates from clinging onto the surface and/or edges of the recess. Optionally in any of the embodiments disclosed herein, one or more walls of the recess may be impregnated with an antimicrobial material. For example, the antimicrobial material may be integrally formed with the recess of the housing to help control the bacterial level present on or within the recess.

The dispenser may optionally include a cutting edge. For example, FIG. 1A shows a cutting edge 140 located on a bottom portion of the housing 110. A sliding cutter may also be included. The cutting edge may be detachably coupled to the housing, or integrally formed as part of the housing. The cutting edge can include a serrated sharp edge or it may simply be a sharp edge that is used to cut and release a portion of the film after the barrier has been applied to a stethoscope head.

Optionally in any of the embodiments disclosed herein, the dispenser need not include a cutting edge. For example, the film may be segmented into a plurality of pieces that are separably coupled together by perforations. The plurality of pieces may include any number of pieces, for example 100, 200, 300, 400, 500, 600, 700, 800, 900, 1000, 2500, greater than 2500, or any number in-between. The perforations allow each piece to be manually separated from the rest of the roll for a single use with the stethoscope. Alternatively, each piece or sheet may be stacked individually and interleaved together, for example similar to interleaved stacked tissue sheets (e.g. Kleenex®). Each piece may be used to form a barrier on the stethoscope head. Accordingly, a cutting edge, or a rolling cutter can be omitted in those embodiments since the pieces of film can be manually and easily separated by hand along the perforations, and are separate and distinct sheets of barrier.

Figure 1B:
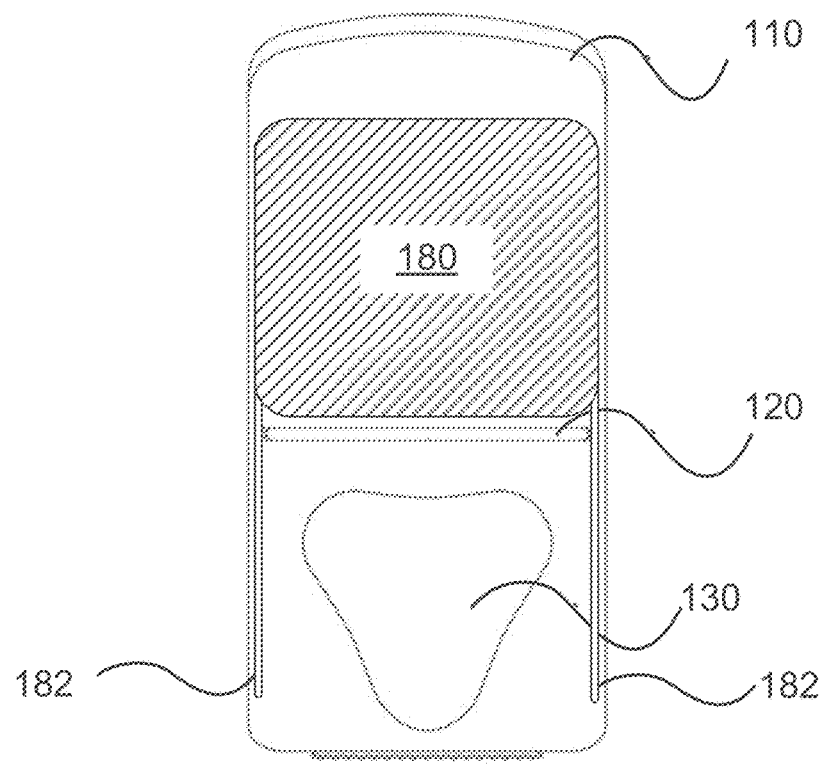
FIGS. 1B and 1C are front views of a barrier dispenser comprising a cover in accordance with an embodiment.
Figure 1C:
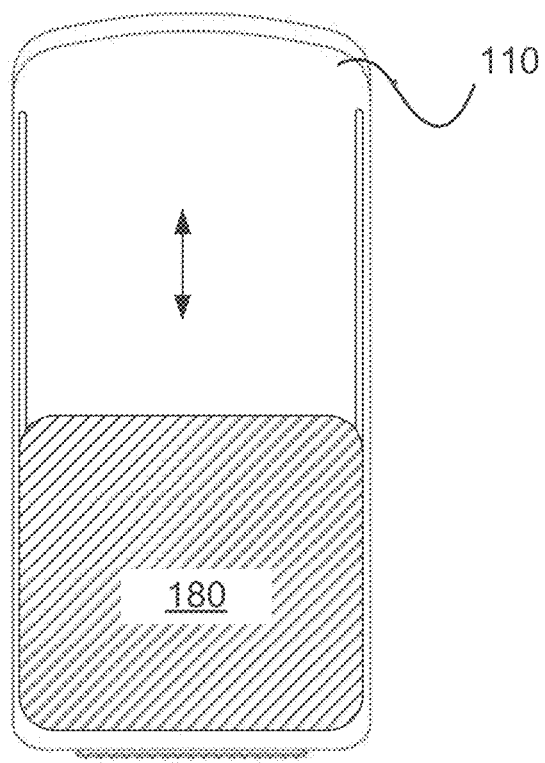

Optionally in any of the embodiments described herein, a cover may be provided on the housing. For example, FIGS. 1B and 1C show front views of a barrier dispenser comprising a cover 180. The cover may be located on the front portion of the housing 110, or anywhere on the housing. The cover may be configured to cover the opening 120 and the recess 130 when the dispenser is not in use, so as to protect the recess and the barrier material within the housing from microbes, viruses, germs, pathogens, microorganisms, disease, or bacteria possibly transmitted airborne or via human contact. The cover may be moved to an open position to permit access to the opening 120 and the recess 130 when the dispenser is in use or to be used. The cover can be movable, for example with the aid of a sliding mechanism 182. The sliding mechanism may include rails, bearings, wheels, dovetail designs, belts, chains, rack and pinion, or any combination thereof. The cover may be manually opened or closed by a user sliding the cover between an open position (FIG. 1B) and a closed position (FIG. 1C). The sliding motion may include translation along a vertical axis. Optionally in any of the embodiments described herein, the cover may be opened or closed via a combination of translation and/or rotation motions. Optionally in any of the embodiments described herein, the cover may be configured to automatically open or close in response to an input from an operator, for example via switches, actuators, motion detection sensors, etc.

Figure 2A:
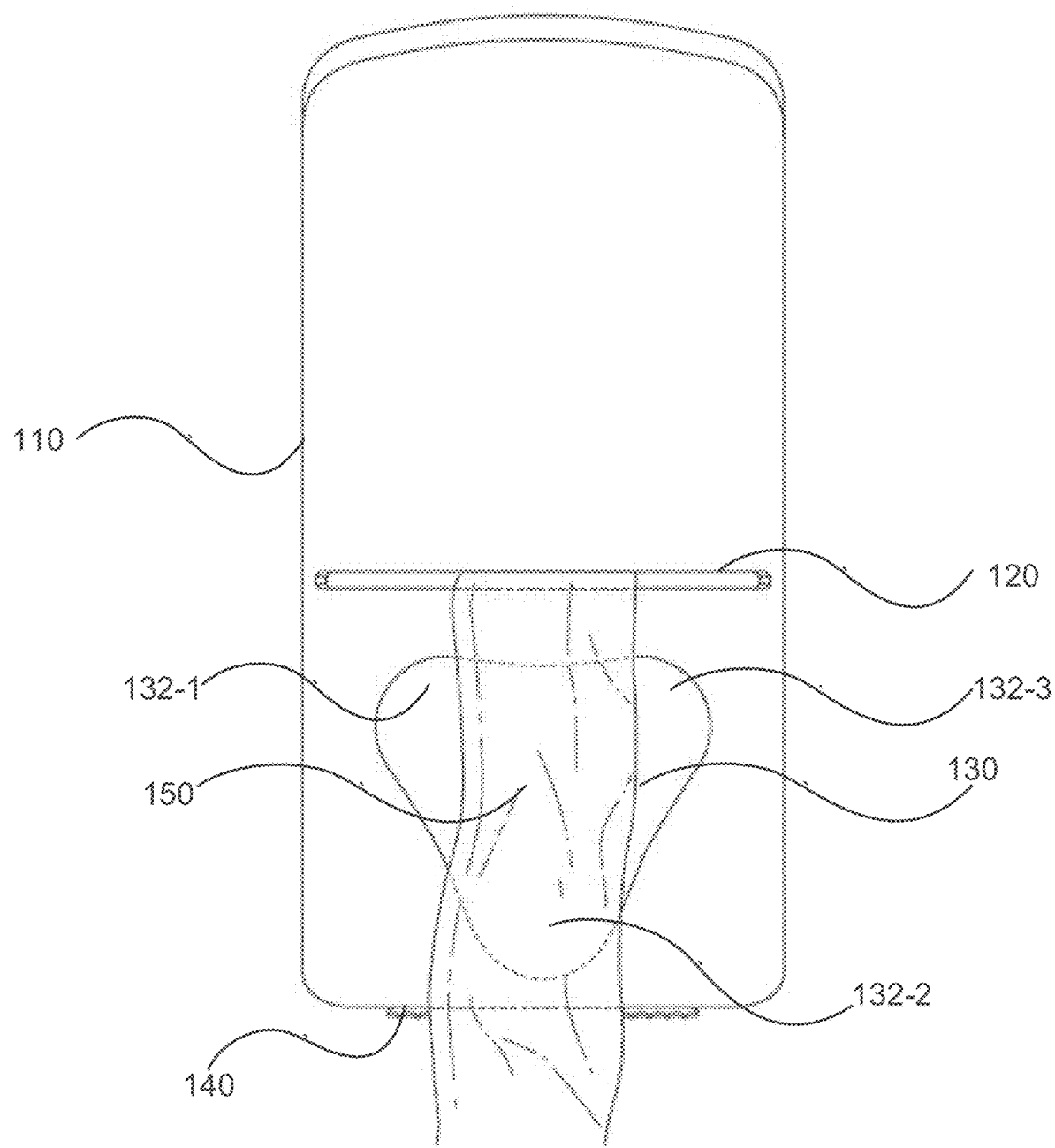
FIG. 2A is a front view of the dispenser of FIG. 1A and shows a film hanging in proximity to a recess.

FIG. 2A is a front view of the barrier dispenser from FIG. 1A showing a film hanging in proximity to a recess. The recess 130 may be located such that a film 150 is permitted to hang freely in proximity to the recess. The film may be dispensed from the opening 120 to hang or drape freely over the recess. Prior to use, an operator may remove a hanging piece of film, pull out a fresh or new piece of film, and proceed with applying the fresh or new piece of film to the stethoscope head. The film may be provided as a roll of film, cassette, or individual stacked sheets of film supported within the chamber of the housing 110. The roll of film, cassette, or individual stacked sheets of film may contain sufficient film for applying a plurality of barriers onto the stethoscope head for a large number of patient encounters (for example, tens, hundreds or thousands of patients). The dispenser may be configured to dispense the film from the opening, in a manner similar to paper towel dispensers that are used in public restrooms. The dispenser may include a mechanism for a user to manually dispense the film (for example by cranking a bar or turning a knob on the housing). Alternatively, the dispenser may be configured to automatically dispense a predetermined amount of film to form a single barrier for each use or patient encounter.

As shown in FIG. 2A, the film 150 may be dispensed such that it hangs directly in front of the recess. The film may drape over the recess. The film may or may not completely cover the recess. In the example of FIG. 2A, the film may extend over the recess covering only the second lobe 132-2 at the bottom corner of the recess. The first lobe 132-1 and third lobe 132-3 at the top left and right corners of the recess may not be covered by the film. Optionally in any of the embodiments disclosed herein, the film may drape over the recess completely covering the first, second and third lobes as described and illustrated elsewhere herein.

The recess 130 can be adapted to allow the film 150 to be applied to a stethoscope head when the stethoscope head is placed into the recess with the film located in-between. For example, a user can place the stethoscope head onto the overhanging film and into the recess, and move the stethoscope head within the recess to apply the film to the stethoscope head to form the barrier. The radius of the corners and/or the rounded concave lobes can be adapted to receive different stethoscope heads having different dimensions (e.g. diameter or thickness). The radius of the corners and/or the lobes can be adapted to allow the film to conform or wrap around the stethoscope head, when the stethoscope head is moved within the recess between the corners and/or the rounded concave lobes. The radius of the corners and/or the lobes can be configured to permit a user to slide the stethoscope head in a smooth manner from a first position to a second position within the recess thereby securing the film to the scope. Exemplary methods of forming or applying the barrier to the stethoscope head will be described in more detail elsewhere herein.

The recess 130 may have a larger size than the stethoscope head in order to permit translation and/or rotation of the stethoscope head within the recess. Optionally in any of the embodiments disclosed herein, the size of the recess may be greater than the size of the stethoscope head by at least about 5%, 10%, 15%, 20%, 25%, 30%, 35%, 40%, 45%, or 50%. The size of the recess may be defined by one or more dimensions of the recess, e.g., diameter, circumference, diagonal, length, width, height, thickness, area, volume, distance between two or more arbitrary points, etc. The size of the stethoscope head may be defined in a similar manner, for example based on its width, diameter and/or thickness. The stethoscope heads may have different shapes and/or sizes, and can be configured for different uses (e.g., adult, pediatric, etc.) as previously described. The recess can be configured to receive stethoscope heads of different shapes and/or sizes, and stethoscopes for different applications (e.g., adult, pediatric, EMS, etc.) as described elsewhere herein. As an example, the recess can be configured to receive stethoscope heads of different diameters, thicknesses, and/or form factors. Optionally in any of the embodiments disclosed herein, a width of the recess may range from about 2 to 6 inches, it could be less, in between, or more. Alternatively, the width of the recess may be less than 2 inches or greater than 6 inches, it could be less, in between, or more.

The bottom of the recess may be substantially planar to permit in-plane movement of the stethoscope head within the recess. The bottom of the recess may be configured to be substantially planar if the stethoscope head has a substantially planar surface at its distal end. Optionally in any of the embodiments disclosed herein, a surface profile at the bottom of the recess can be configured or designed to match the distal surface of the stethoscope head. For example, if the stethoscope head has a slight convex profile at its distal end, the bottom of the recess may be slightly concaved to increase contact area between the two. Increased contact area allows the film to be sufficiently and evenly applied over the distal surface of the stethoscope head, with reduced airgaps or creases in-between, thereby forming a well-adhered protective barrier.

The recess may include a surface at its bottom on which the stethoscope head (and film) is configured to move. Essentially, any conceivable material may be employed in forming the surface of the recess. The surface of the recess may be made of metals, plastics, composites, glass, organic materials, inorganic materials, or a combination of any of these. The surface of the recess may have any convenient shape, such as a curved shape, spherical, hemispherical, square, circle, cuboid, trapezoidal, disc, etc. The surface of the recess may be smooth, or may take on a variety of alternative surface configurations. For example, in some cases, the surface of the recess may contain raised or depressed regions. In some cases, the surface of the recess may include plates, sheets, pads, slices, films, slides, bearing layers, etc. In some cases, tracks can be formed on the surface of the recess. By way of example, the tracks may include grooves, trenches, mesa structures, or the like. The stethoscope head can be configured to move along the tracks on the surface of the recess. The surface of the recess may comprise a number of discrete pieces arranged together leaving gaps therebetween to form the tracks. Alternatively, the tracks may be machined or etched onto the surface of the recess using well-known techniques to provide for desired surface features. For example, machining processes such as milling, laser cutting, water jets, etc. can be employed in the formation of the tracks on the surface of the recess.

Optionally in any of the embodiments disclosed herein, the bottom of the recess may include a material that has a lower adhesion strength/affinity to the film than to the stethoscope head. This ensures that the film does not adhere to the bottom of the recess when the stethoscope head is placed into the recess, moved within the recess, or removed from the recess. In some cases, the bottom of the recess may be sprayed or coated with a material having non-stick properties that prevents the film from sticking or adhering to the bottom of the recess.

The bottom of the recess may have a rigid surface that does not deform when the stethoscope head is pressed into and moved within the recess. Alternatively, the bottom of the recess may include an elastic material such as an elastomer. The elastic material may be configured to conform to the shape of the stethoscope head. The elastic material may compress or press the film against the stethoscope head when the stethoscope head is placed into or moved within the recess. The compression may help to improve the contact area between the film and the stethoscope head. As described above, increased contact area allows the film to be sufficiently applied over the distal end of the stethoscope head, with reduced airgaps or creases in-between, thereby forming a well-adhered protective barrier.

Any of the dispensers described herein can be mounted to a surface. For example, FIG. 2B is a schematic side view of the dispenser of FIG. 2A attached or mounted to a vertical surface 106. The vertical surface may be, for example part of a wall, cubicle, medication cart, nurses' office, inside an ambulance, or any other vertical surface accessible to health care professionals. Exemplary means of attachment 119 may include nuts and bolts, rivets, screws, nails, locks, latches, wires, joints, soldering, welding, gluing and the like. In any of the embodiments described herein, the housing 110 of the dispenser may include mounting brackets for coupling the dispenser to the vertical surface. In some cases, the dispenser may be mounted horizontally onto a horizontal surface.

The dispenser may include a source 151 of barrier material in the form of film 150. The source 151 may be supported within the chamber of the housing. The film 150 may extend from the source 151 such that a distal portion of the film exits the opening 120 and drapes over the recess 130.

Optionally in any of the embodiments described herein, the dispenser may further include an energy source 170, for example as shown in FIG. 2C. The energy source may be provided within the chamber of the housing 110. The energy source may comprise a UV light source configured to illuminate UV/UV-C light 172 onto the film 150. The UV light source may comprise one or more UV-LEDs. The UV light source may be powered by a power supply located on the dispenser or remote to the dispenser. In any of the embodiments described herein, the UV light source or other light source can be powered by a solar panel. The solar panel may comprise one or more solar energy cells. The solar panel can be mounted on the dispenser, for example on a front, side or top portion of the housing 110. The solar panel may include monocrystalline silicon or any other semiconductor materials for harnessing solar energy. In some cases, the solar panel may be configured to output power, for example 0.2 W or higher. The solar panel can be configured to provide any power output, depending on the size of the chamber, the amount or thickness of the barrier material to be irradiated, the type of barrier material, etc. The solar panel may be formed having any shape, size and/or design to match the housing, and can be located on a portion of the housing that does not interfere with the barrier dispensing operation of the dispenser or the operation of the solar panel.

The UV light source may be configured to illuminate a top portion of the film between the source 151 and the opening 120, for example as shown in FIG. 2C. Alternatively, the UV light source or other light source may be configured to irradiate the film from a plurality of directions (e.g., top, bottom and lateral sides), thereby effectively providing a UV chamber/bath/shower for sterilizing the film prior to use, and prior to application of the film to a stethoscope head.

Figure 3A:
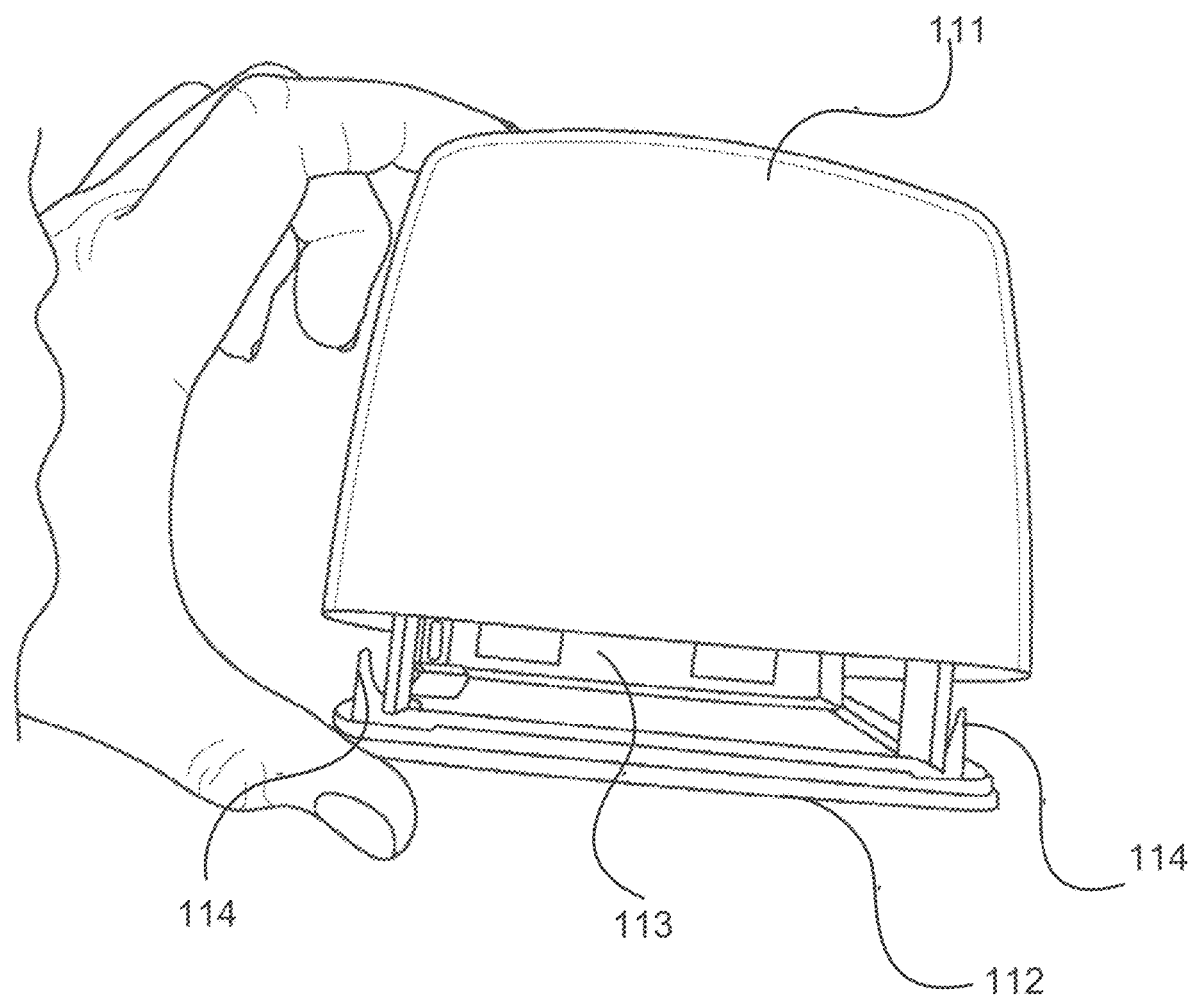
FIG. 3A is a perspective view showing a housing assembly of a barrier dispenser in accordance with an embodiment.

FIG. 3A is a perspective view showing a housing assembly of a barrier dispenser, in accordance with an embodiment which may include FIG. 1A or any of the embodiments described in this specification. The housing 110 may include a cover 111 and a base 112 configured to be coupled together. In some cases, the cover may be detachably coupled to the base such that the cover can be completely removed from the base via a locking/unlocking mechanism (e.g., snapfits, screws, etc.). In some cases, the cover may be rotatably coupled to the base using hinges. The hinges may be coupled to pivot pins such that the cover can rotate relative to the base. The cover may be closed or opened. A chamber 113 is provided within the housing when the cover is in a closed position. The cover can be opened by releasing snapfits 114 or any other type of unlocking mechanisms. The cover can be opened to allow a user to load a source of barrier material (e.g., a roll of film) into the housing. This allows an operator to easily access the inside of the dispenser, especially when replacing the film, or to allow easy cleaning of the chamber.

Figure 3B:
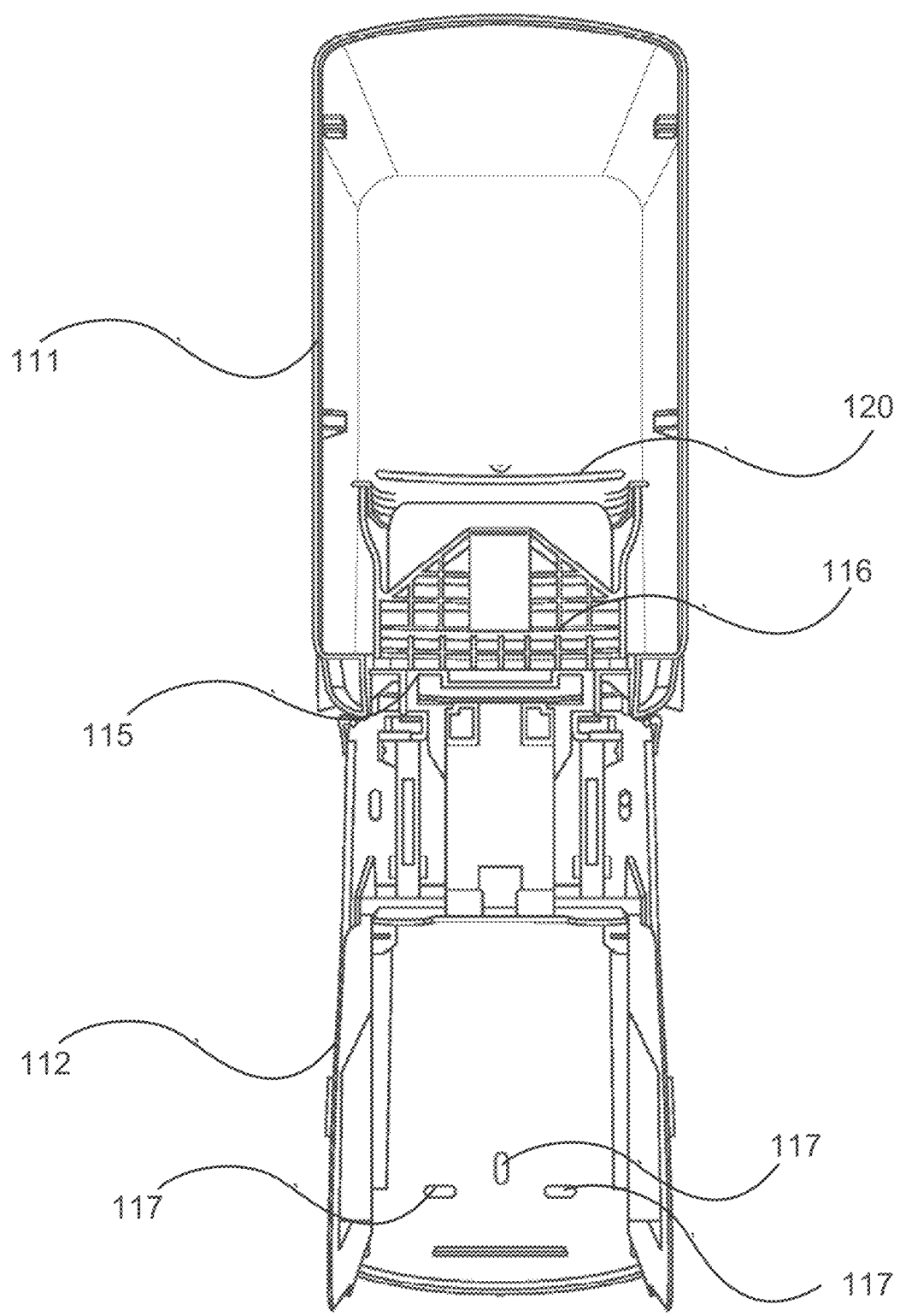
FIG. 3B is a perspective view of an internal structure of the barrier dispenser of FIG. 3A.

FIG. 3B is a perspective view showing an internal structure of the barrier dispenser of FIG. 3A. The cover 111 can be opened, for example by rotating the cover about hinges 115, to expose the inside of the housing. The opening 120 may be formed on the cover. The recess 130 (not shown) may be provided on a front side of the cover. Optionally in any of the embodiments disclosed herein, ribs 116 may be provided to reinforce a rear portion of the recess. Structural reinforcement can be advantageous for prolonging the life of the dispenser since the recess is subject to repeated forces by a user during application of the barriers to the stethoscope head for multiple users (patient encounters). The base 112 may include a plurality of mounting holes 117-1, 117-2, and 117-3 for allowing the dispenser to be attached a structure (e.g., a wall). Optionally in any of the embodiments disclosed herein, an energy source (e.g., a UV/UV-C light source or other light source) may be provided on the inside of the housing, for example as described later in the specification and illustrated in FIG. 4E.

Figure 4A:
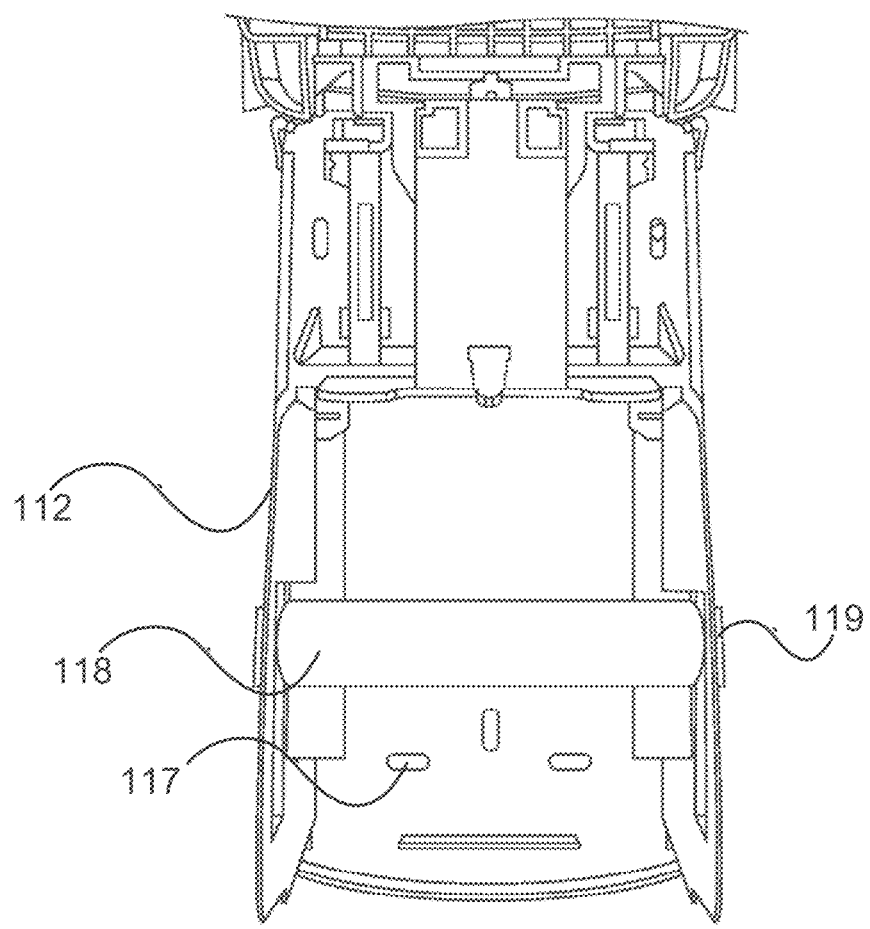
FIG. 4A is a perspective view showing a roller coupled to an inner portion of a barrier dispenser, in accordance with an embodiment.
Figure 4B:
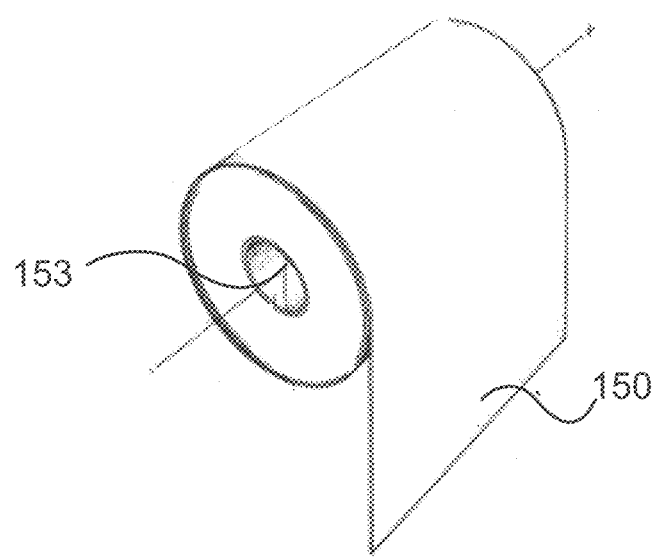
FIG. 4B is a perspective view showing a roll of film that is configured to be coupled to the roller of FIG. 4A.
Figure 4C:
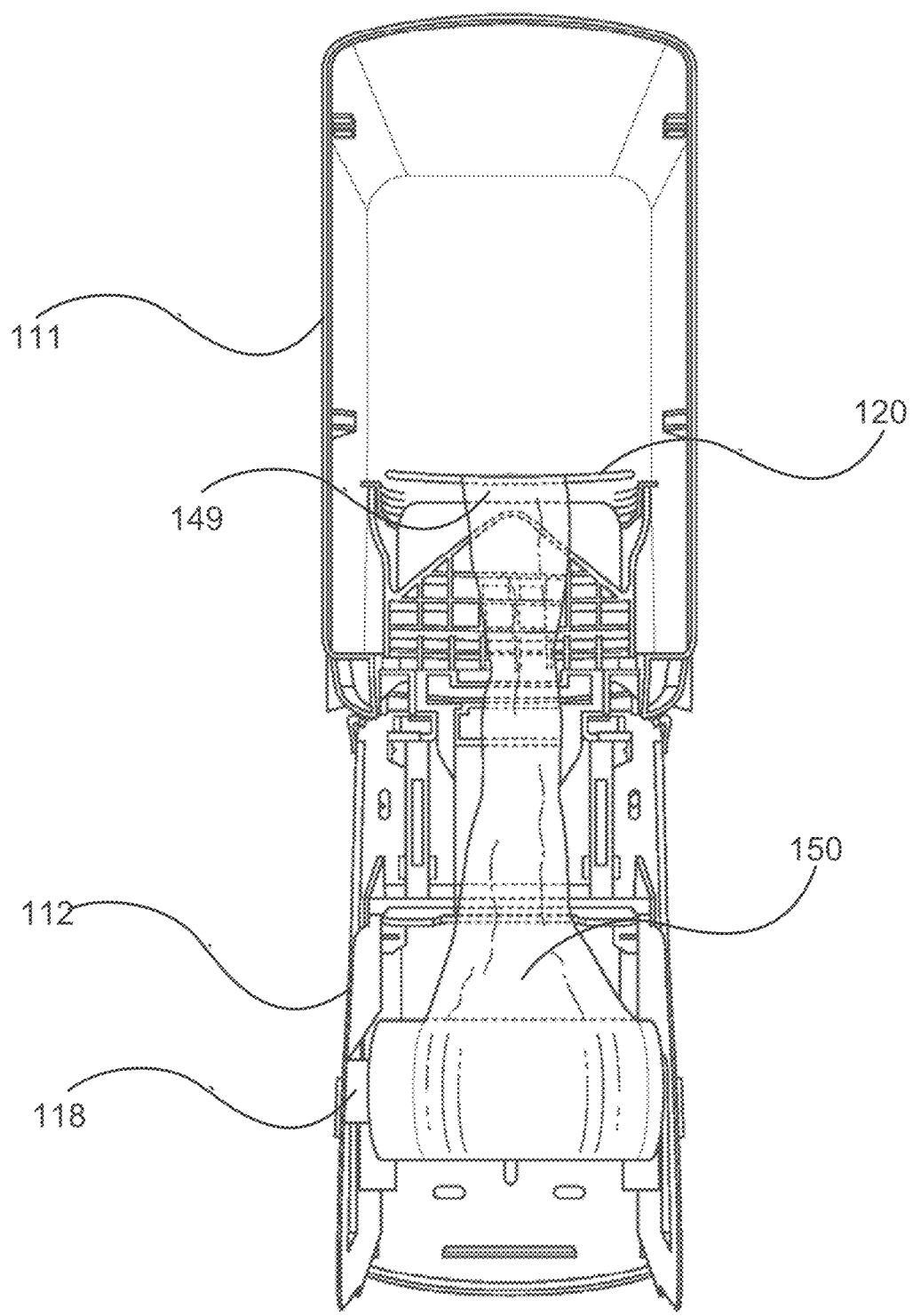
FIG. 4C is a perspective view showing the roll of film coupled to the roller and extending to a slot opening of the barrier dispenser, in accordance with an embodiment.

FIG. 4A is a perspective view showing a roller coupled to an inner portion of the barrier dispenser which may be in any of the embodiments disclosed herein. A roller 118 may be coupled to the base 112. The roller may be rotatably coupled to the base via hinges or tabs 119. The roller may be configured to support and dispense a source of barrier material (e.g., a roll of film 150 as shown in FIG. 4B). The film may be wound around a longitudinal tube 153 multiple times to form the roll of film. The roller may be detached from the housing, inserted through the tube (roll of film), and then mounted back into the housing, for example as shown in FIG. 4C. The base may include a dispense mechanism (not shown) operably coupled to the roller and configured to cause the roller to rotate. The dispense mechanism may include, for example a knob, crank, automated mechanism, bar, stored energy mechanism, etc. When a roll of film is mounted to the roller, rotation of the roller in one direction (clockwise or counterclockwise) can cause the roll of film to unroll and dispense. A user can manually dispense the film, for example by cranking the bar or turning the knob on the housing, or pulling up a sheet in a manually dispensed scenario. In some cases, the dispense mechanism may be omitted for manually dispensed barriers. For example, the dispenser may be configured to automatically dispense a predetermined amount of film to form a single barrier for each use or patient encounter. Optionally in any of the embodiments disclosed herein, the dispense mechanism may include a sensor that detects when a scope is adjacent the housing and automatically triggers the dispense mechanism to dispense the film.

FIG. 4C is a perspective view showing a source of film coupled to the roller and extending to an opening of the barrier dispenser that may apply to any embodiment disclosed herein. A source of the barrier material may include a roll of film 150. The roll of film may be mounted onto the roller 118. The roll of film can be unrolled such that a distal portion 149 of the film extends to the opening 120. The distal portion of the film can be inserted through the opening to extend beyond the cover 111. The distal portion of the film can be extended such that it hangs in proximity to the recess of the housing, as described elsewhere herein.

Figure 4D:
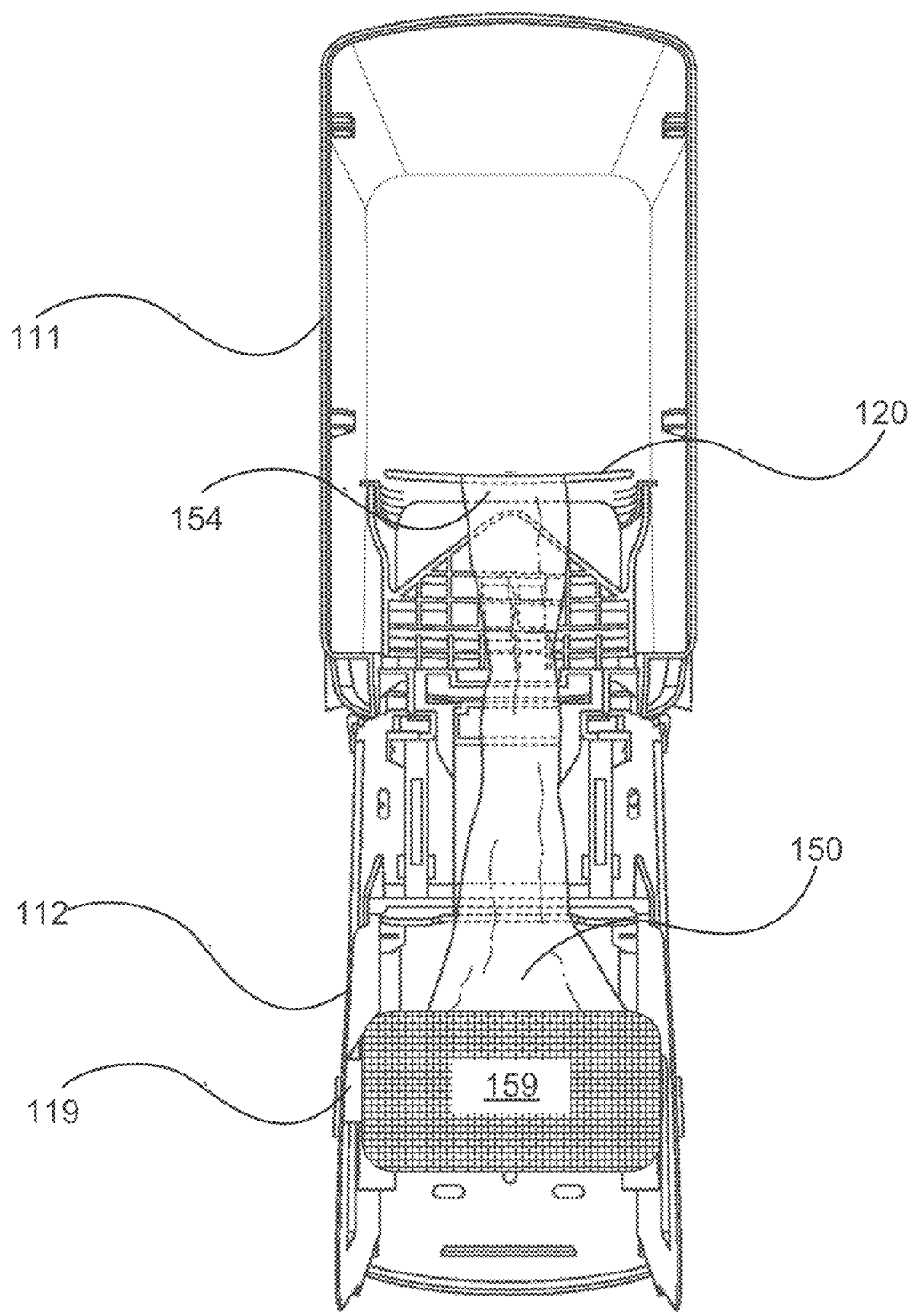
FIG. 4D is a perspective view showing the roll of film being provided in a cassette, in accordance with an embodiment.

FIG. 4D is a perspective view showing the roll of film being provided within a cassette 159 that may apply to any embodiment disclosed herein. The cassette can help to keep the roll of film in a clean environment, and protect the film from contaminants, dust, microbes, germs, bacteria, moisture, etc. The cassette can be easily coupled to the base via hinges or tabs 119 to permit quick loading/unloading of the cassette. The cassette may comprise a stored energy mechanism for automatic film dispensing. For example, the stored energy mechanism may include a spring that is energized when a user pulls and withdraws film from the dispenser. The spring can be configured to move the roll of film to dispense more film (or a preset amount of film) upon release of the stored energy in the spring. The cassette can be removed from the housing when the film has been depleted, to be replaced by another new cassette.

Figure 4E:
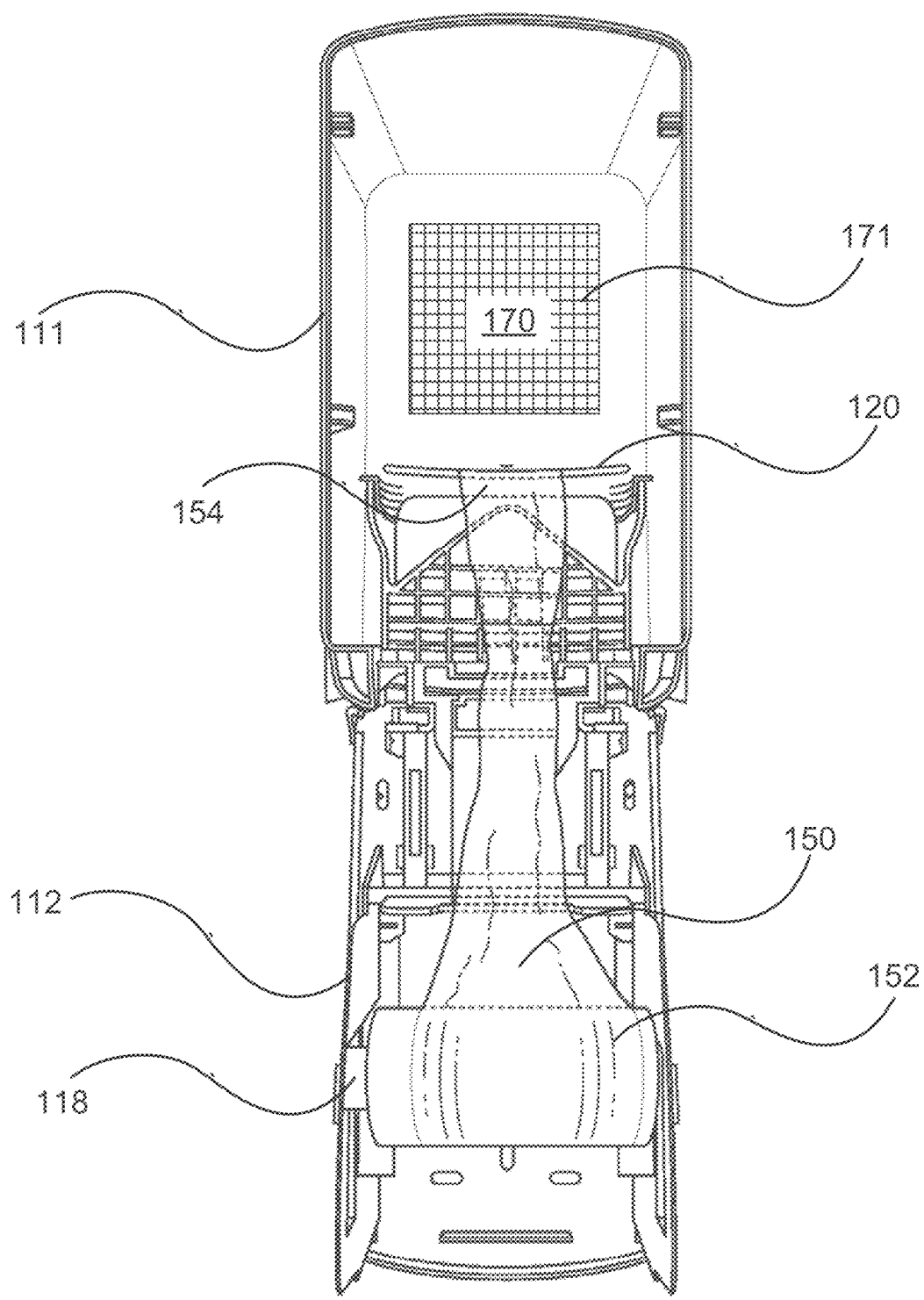
FIG. 4E is a perspective view showing a UV or other light source disposed within the housing, in accordance with an embodiment.

FIG. 4E is a perspective view showing a UV light source or other light source disposed within the housing, that may apply to any embodiment disclosed herein. As previously described, the dispenser may optionally include an energy source 170. The energy source may comprise a UV light source configured to illuminate UV/UV-C light or other light 172 onto the film 150. The UV light source may be provided within the chamber of the housing 110. For example, as shown in FIG. 4E, the UV light source or other light may be attached to or integrally formed on an inside of the cover 111. The UV light source or other light may comprise one or more UV-LEDs or other LEDs. For example, a plurality of UV-LEDs or other LEDs 171 may be provided in a grid pattern on the inside of the cover. Alternatively, the UV-LEDs or other LEDs may be provided in a radial pattern, or any regular or irregular pattern. The plurality of UV-LEDs or other LEDs may be controlled, either individually or collectively, to illuminate the film inside the housing with the UV/UV-C light source or other light source. The UV light source or other light source may be configured to illuminate a portion or all of the film stored within the housing. Alternatively, the UV light source or other light source may be configured to irradiate the film from a plurality of directions (e.g., top, bottom and lateral sides from within the chamber), thereby effectively providing a UV chamber/bath/shower for sterilizing the film prior to use, and prior to application of the film to a stethoscope head.

The UV light source or other light source shown in FIG. 4E or any of the embodiments disclosed herein may be powered by a power supply located on the dispenser or remote to the dispenser. For example, in any of the embodiments described herein, the UV light source or other light source can be powered by a solar panel. The solar panel may comprise one or more solar energy cells. The solar panel can be mounted on the dispenser, for example on an exterior front, side or top portion of the housing 110. In FIG. 4E, the solar panel may be mounted (not shown) on an outer surface of the cover 111 that is opposite to a surface on which the energy source 170 (UV light source or other light source) is mounted. The solar panel and the energy source 170 (UV light source or other light source) are electrically coupled together such that the solar panel is configured to provide power to the UV light source or other light source (e.g. UV-LEDs or other LEDs). The solar panel may include monocrystalline silicon or any other semiconductor materials for harnessing solar energy. In some cases, the solar panel may be configured to output power, for example 0.2 W or higher or lower. The solar panel may be formed having any shape, size and/or design to match the housing, and can be located on a portion of the housing that does not interfere with the barrier dispensing operation of the dispenser or the operation of the solar panel.

Figure 5A:
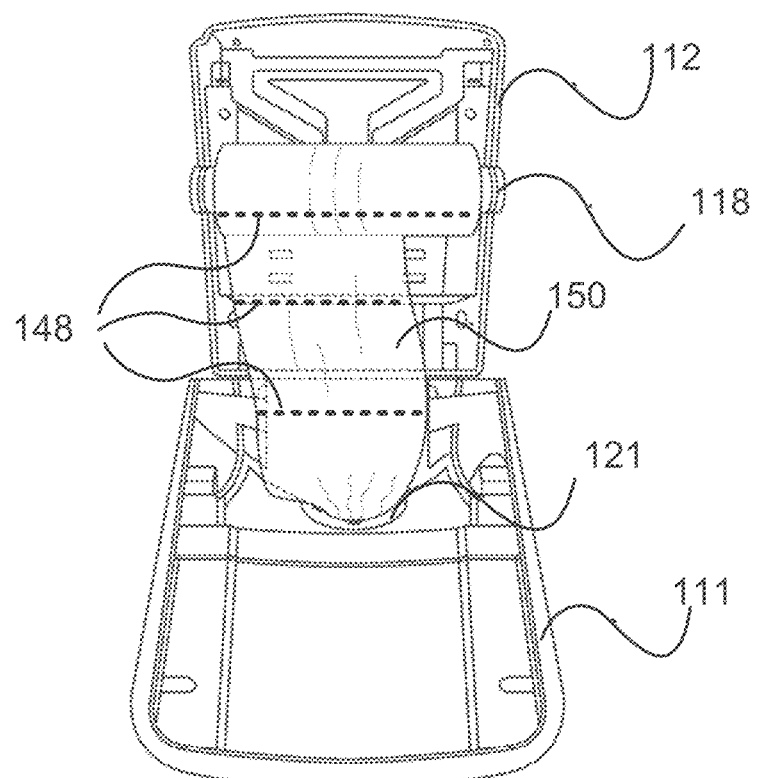
FIG. 5A is a perspective view showing a roll of film coupled to a roller and extending to a circular opening of a barrier dispenser, in accordance with an embodiment.
Figure 5B:
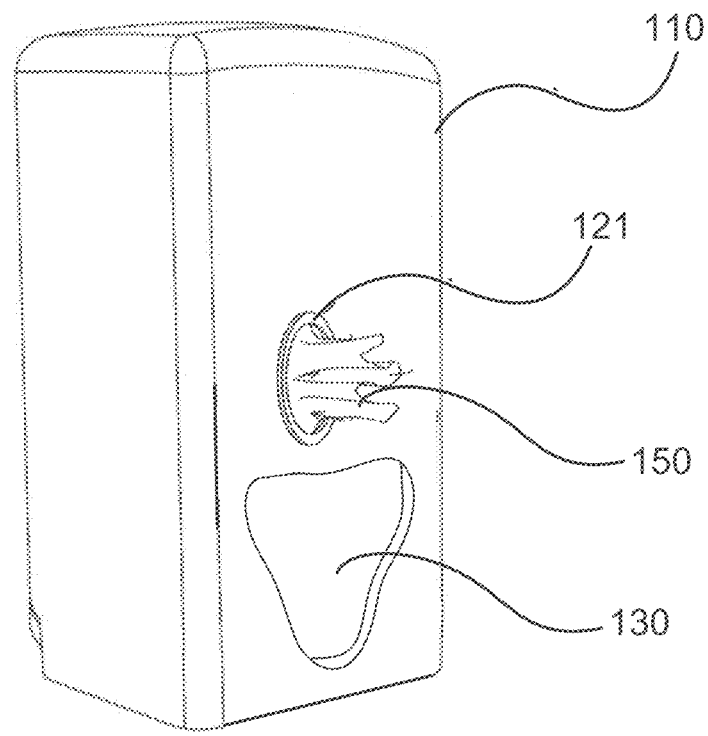
FIG. 5B is a perspective view of the assembled dispenser of FIG. 5A and shows film being dispensed from the circular opening, in accordance with an embodiment.

FIG. 5A is a perspective view showing a roll of film coupled to a roller and extending to a circular opening of a barrier dispenser, that may apply to any embodiment disclosed herein. FIG. 5B is a perspective view of the assembled dispenser of FIG. 5A and shows the film being dispensed from the circular opening. The dispenser may include a substantially circular opening 121 instead of the horizontal slot opening 120 described elsewhere herein. The opening 121 may also be formed having an elliptical shape or any shape that permits the roll of film 150 to be dispensed from the opening without impeding movement of the film. The roll of film may comprise perforations 148 that allow sheets of film to be easily and manually separated by the user by hand. FIG. 5B shows a sheet of film 150 partially extending from the circular opening 121. A user can pull out the film, and separate the sheet from the remaining roll of film by tearing along the perforations. Accordingly, the dispenser shown in FIGS. 5A and 5B optionally need not include any separating mechanism for cutting the film, since the film can be easily separated by hand along the perforations.

Figure 6A:
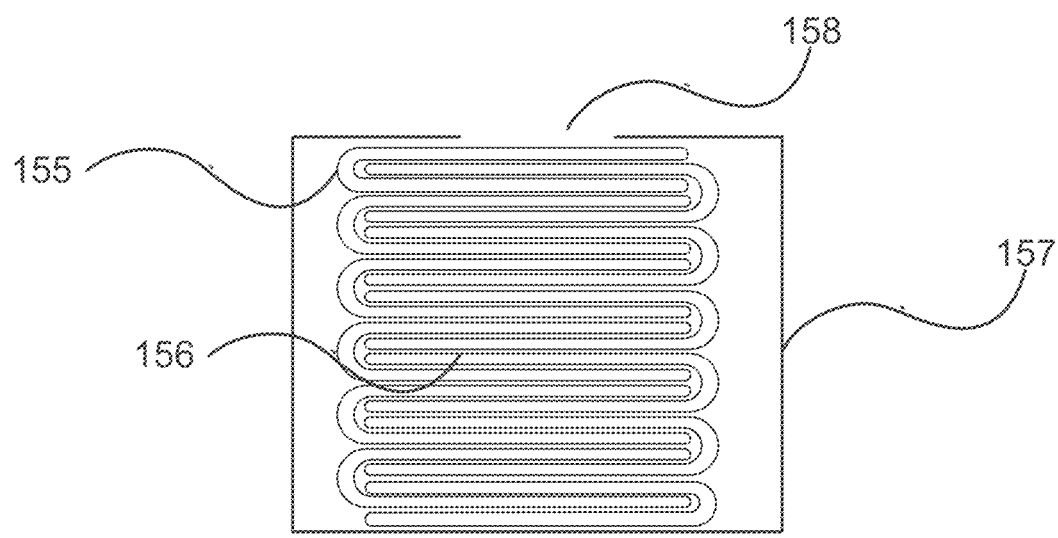
FIG. 6A is a schematic view of a source of barrier material provided in the form of interleaved stacked sheets, in accordance with an embodiment.
Figure 6B:
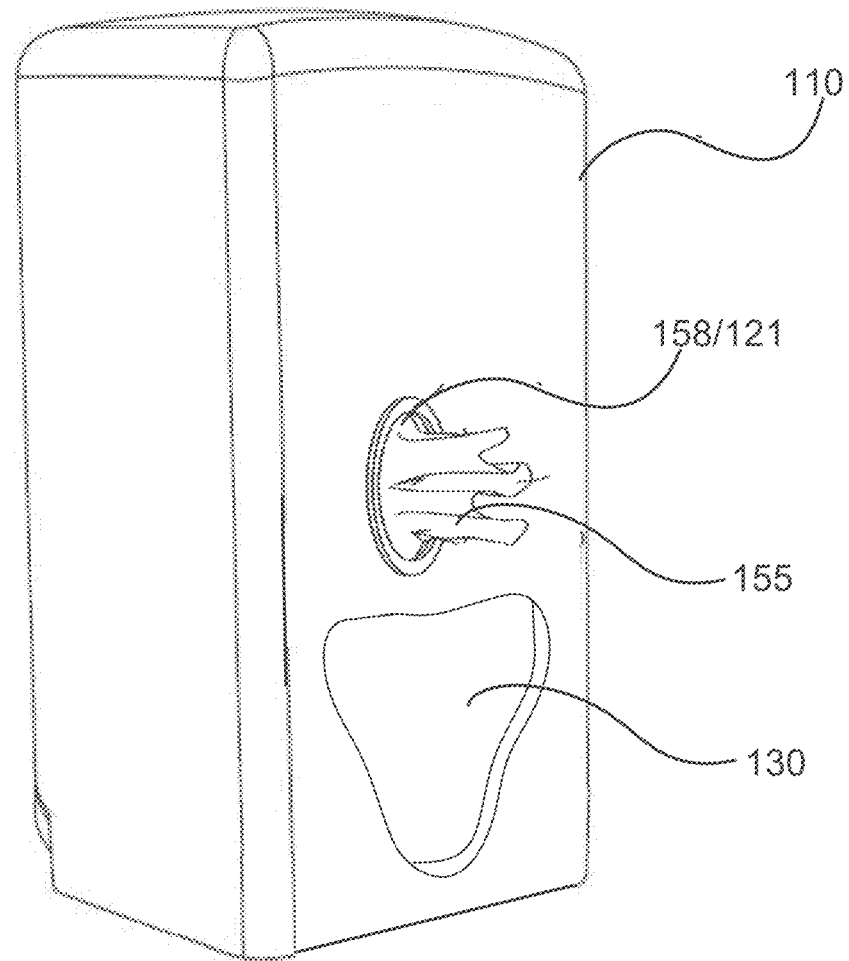
FIG. 6B is a perspective view of a barrier dispenser showing the dispense of a single sheet from the interleaved stacked sheets of FIG. 6A, in accordance with an embodiment.

FIG. 6A is a schematic side view of barrier material provided in the form of interleaved stacked sheets, that may apply to any embodiment disclosed herein. FIG. 6B is a perspective view of a barrier dispenser showing the dispense of a single sheet from the interleaved stacked sheets of FIG. 6A. Referring to FIG. 6A, the barrier material may be provided as a plurality of separate sheets 155 that are folded, interleaved 156 and stacked together in the configuration as shown. The stack of interleaved sheets may be stored in a sheet container 157. The sheet container comprises an opening 158 that is configured to permit a sheet that is closest to the opening to be removed. The sheets are interleaved such that when a user pulls out and removes a sheet from the opening 158, an underlying sheet beneath would be transformed from a planar folded configuration to a three-dimensional configuration. The underlying sheet would then extend out from the opening to replace the sheet that was removed, thereby allowing a user to retrieve sheets from the container easily without having to probe into the container with fingers. FIG. 6B shows the three-dimensional configuration of a single sheet extending out of the opening 158 of the container and the opening 121 of the housing. In the example of FIGS. 6A and 6B, the dispenser may include a substantially circular opening 121 instead of the horizontal slot opening 120 described elsewhere herein. The opening 121 may also be formed having an elliptical shape or any shape that permits the interleaved stacked sheets to be dispensed from the opening. For example, the shape and/or size of the opening may be configured based on the interleaving pattern of the sheets, so as to allow separate sheets to be dispensed easily while preventing the underlying sheet from falling back into the sheet container.

Figure 7:
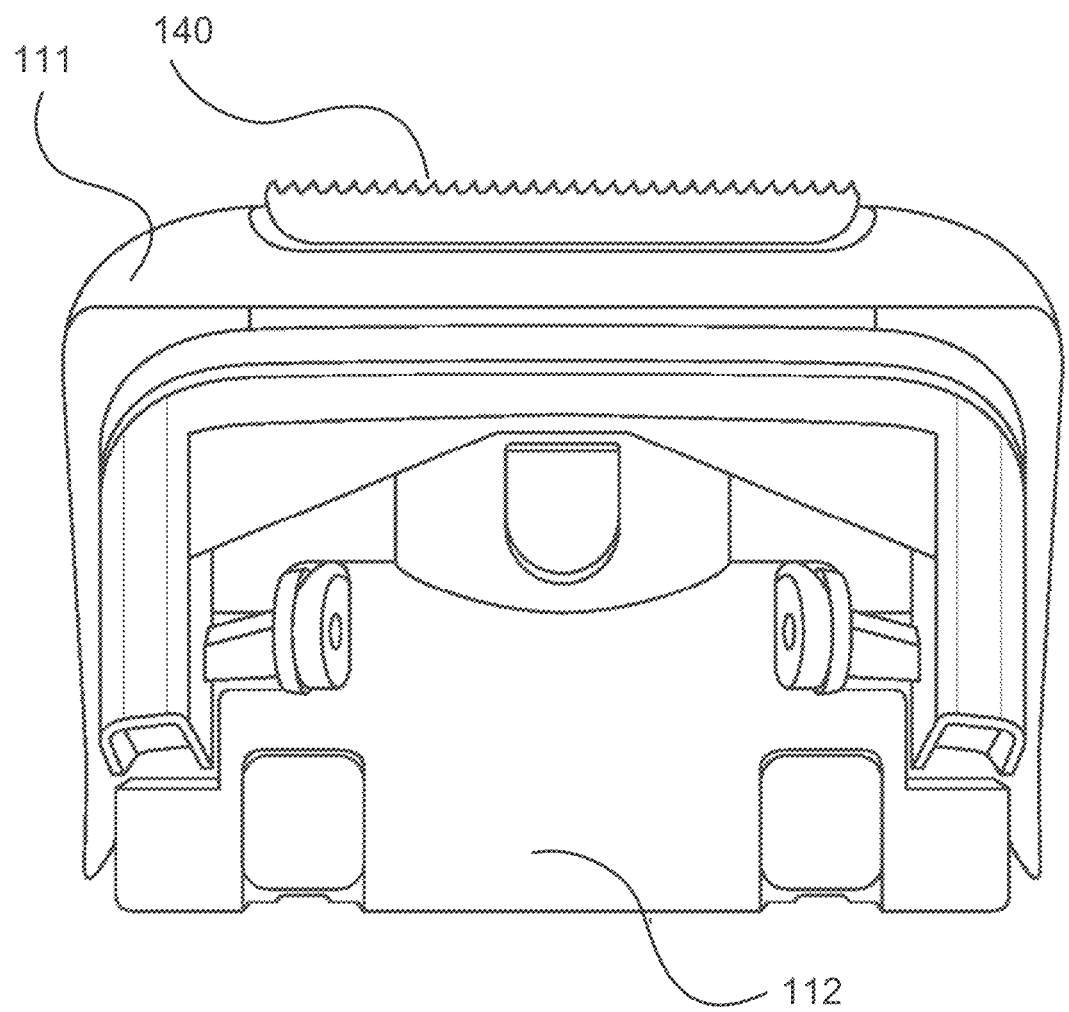
FIG. 7 is a bottom perspective view showing a cutting edge of a barrier dispenser in accordance with an embodiment.

FIG. 7 is a bottom perspective view showing a cutting edge of a barrier dispenser that may apply to any embodiment disclosed herein. As previously described, the dispenser may optionally include a cutting edge 140 and optionally may be used with any dispenser disclosed herein. The cutting edge may be located on a bottom front portion of the cover 111. The cutting edge may be detachably coupled to the cover, or integrally formed as part of the cover. The cutting edge can be fixed or movable. For example, a sliding cutter may also be used. Optionally in any of the embodiments disclosed herein, the cutting edge may be located on the base 112 instead of the cover. The cutting edge can include a serrated sharp edge that is used to cut and release a portion of the film after the barrier has been applied to a stethoscope head, or it may be a straight cutting edge. The cutting edge can be configured to cut and release a portion of the film after the film has been applied to a stethoscope head to form a barrier. The length of the cutting edge can be customized to permit an entire width of the film to be cut. In some cases, a longitudinal length of the cutting edge may be the same or longer than the width of the film to be cut. The cutting edge may be oriented at an angle that permits the film to be cut easily when a user pulls down the film and applies pressure to the film over the cutting edge. In any of the embodiments described herein, the cutting edge or a cutter can be omitted, if the barrier material is provided in the form of perforated film, or as a stack of separate interleaved sheets that can be manually dispensed without requiring cutting.

FIGS. 8A through 8F illustrate an exemplary method of moving a stethoscope head within a recess to apply a barrier to the stethoscope head, in accordance with any of the embodiments disclosed herein. FIGS. 9 through 17 are perspective views showing application of the barrier to the stethoscope head in accordance with the method shown in FIGS. 8A-8F as will be described below. The stethoscope head can be translated and/or rotated within the recess. A user can move the stethoscope head in a clockwise or counterclockwise direction within the recess, and by any amount (for example, ranging from about 10 degrees to 360 degrees). The translation and/or rotation can cause the film to wrap around the stethoscope head, thereby forming the barrier on the stethoscope head, as described below.

Figure 9:
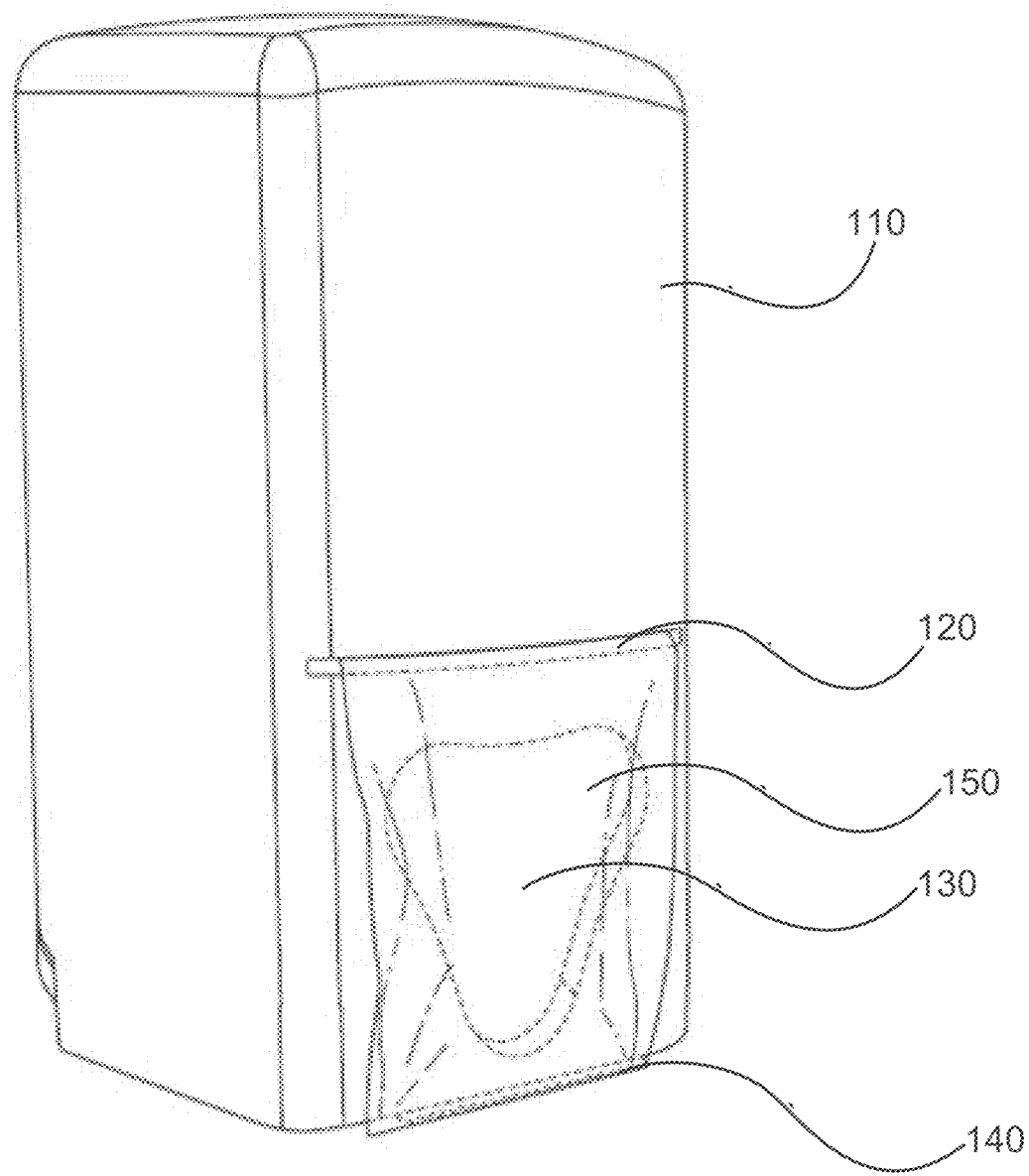

Referring to FIG. 9, the film 150 may be dispensed from the opening 120 such that it hangs over the recess 130. The extended portion of the film may completely cover the recess. In some other cases, the extended portion of the film may cover the recess partially as described elsewhere herein.

Figure 10:
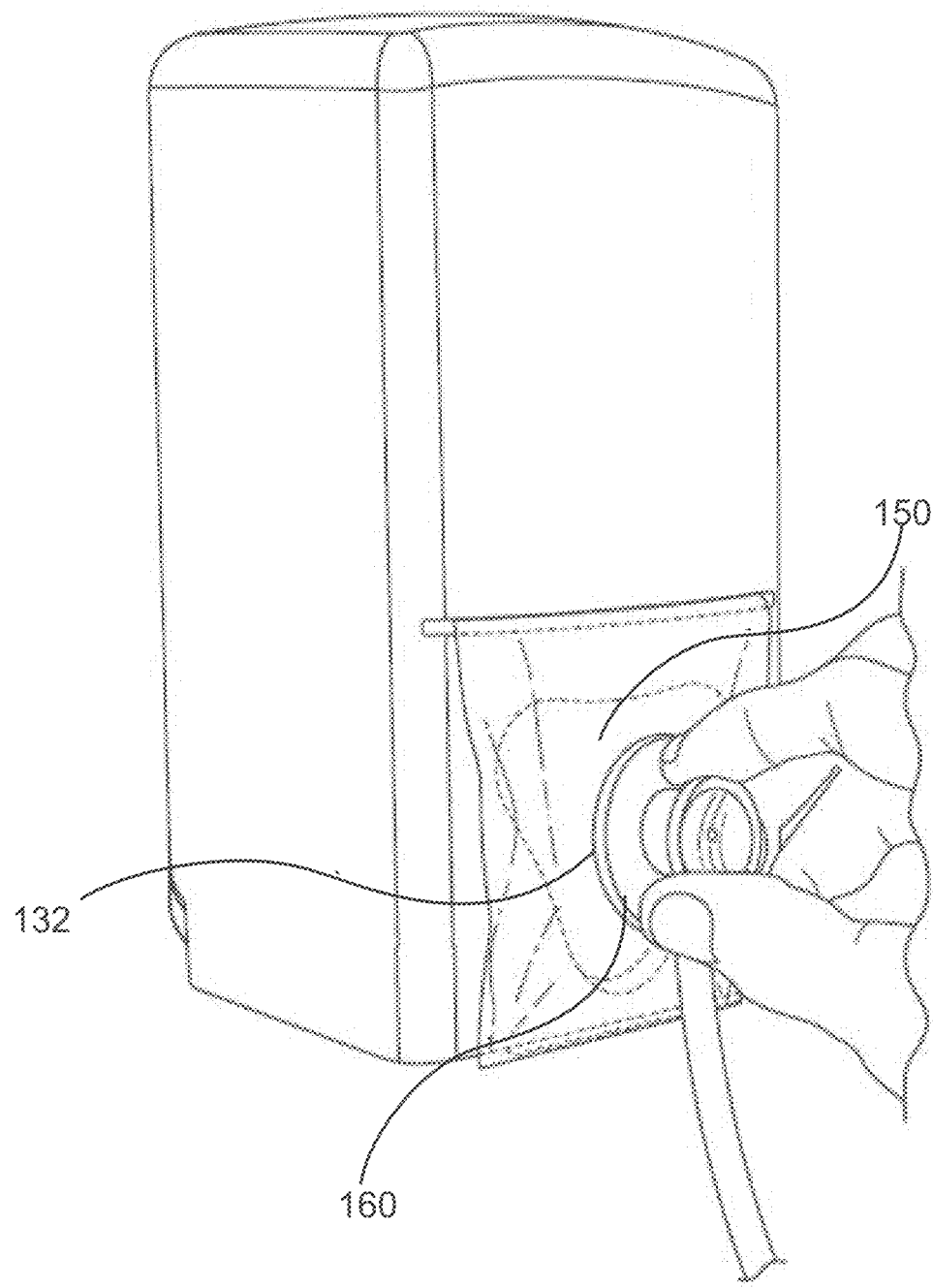

As shown in FIG. 10, a user may place a stethoscope head 160 onto the portion of the film 150 in front of the recess 130. The stethoscope head may be placed, for example substantially at or near a center 132-0 of the recess shown in FIG. 8A. Next, the user may push the stethoscope head with the film into the recess, with the film located in-between the stethoscope head and the recess. The film may be applied onto a distal surface of the stethoscope head when the user pushes the stethoscope head against the bottom surface of the recess. The film may easily attach to the stethoscope head such that light compression of the film causes the film to stick to the stethoscope head. The user may dispose of any hanging material before using, and pull an unexposed barrier or shield or membrane or film before use.

Figure 8A:
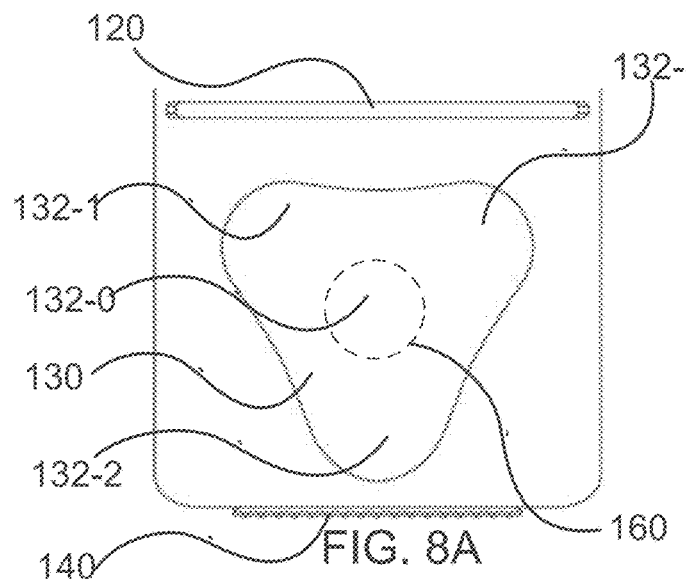
FIGS. 8A through 8F illustrate an exemplary method of moving a stethoscope head within a recess to apply a barrier to the stethoscope head, in accordance with an embodiment.
Figure 8B:
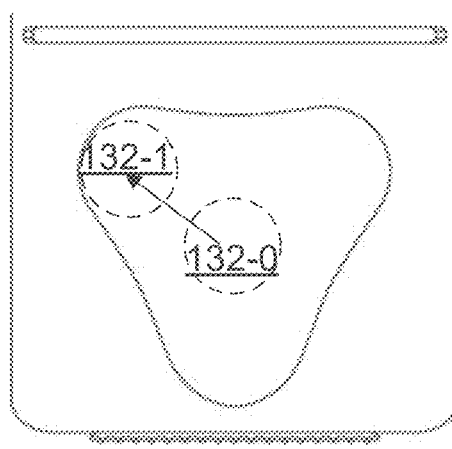
Figure 11:
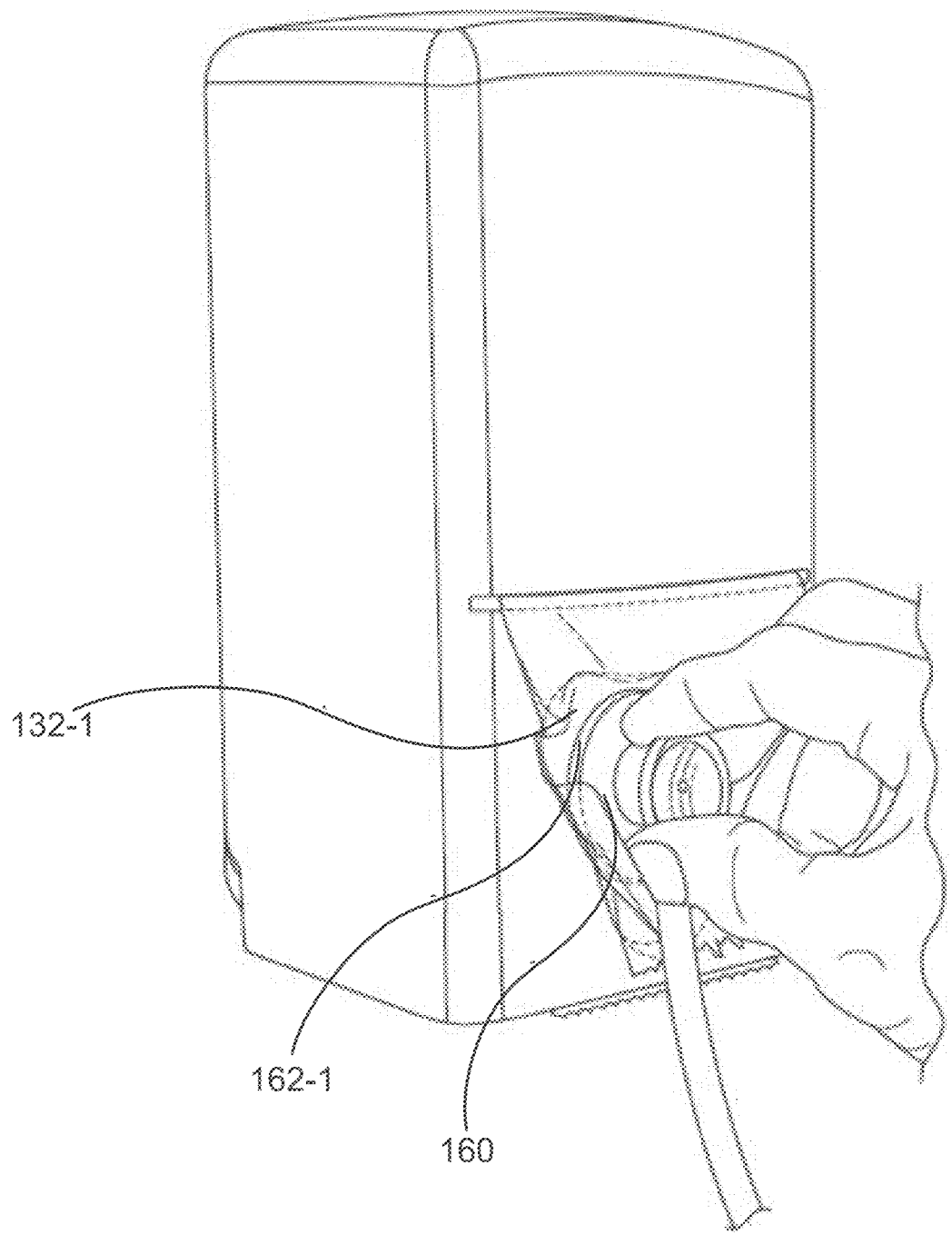

After the stethoscope head has been placed into the recess, the user may move the stethoscope head around, for example by translating and/or rotating the stethoscope head within the recess. The user may move the stethoscope head with the film inside the recess in a clockwise or counterclockwise manner. Referring to FIGS. 11 and 8B, the user may slide the stethoscope head with the film from the center 132-0 to the first lobe 132-1 located at the top left corner of the recess. When the user pushes the stethoscope head against the first lobe, a first portion of the film is pressed onto a first edge portion 162-1 of the stethoscope head. The radius of the first lobe may be configured to increase the contact area between the film and the first edge portion of the stethoscope head.

Figure 8C:
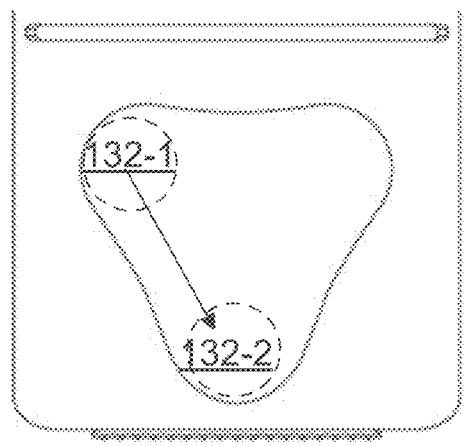
Figure 12:
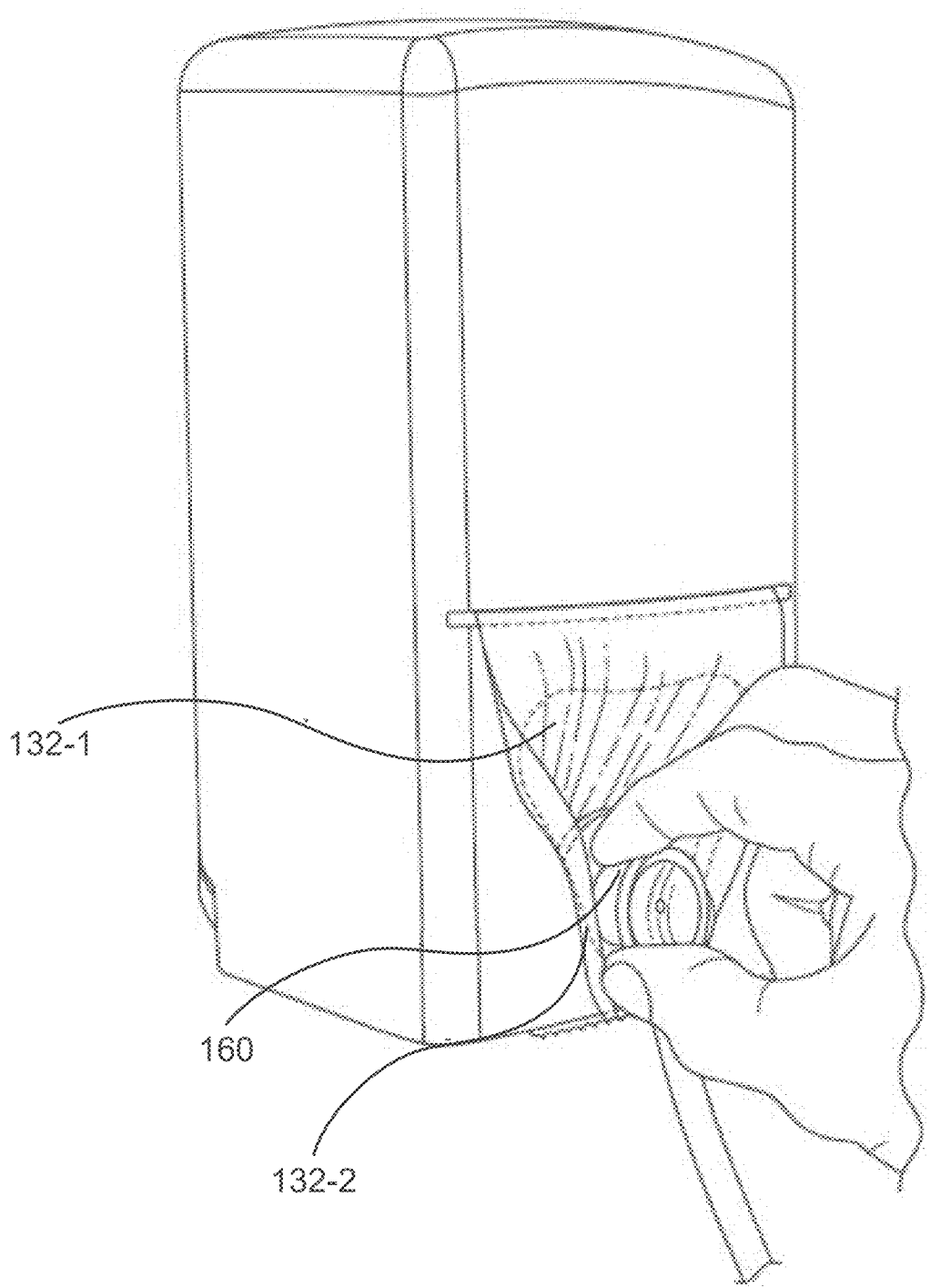

Next, referring to FIGS. 12 and 8C, the user may slide the stethoscope head with the film from the first lobe 132-1 to the second lobe 132-2 located at the bottom corner of the recess. When the user pushes the stethoscope head against the second lobe, a second portion of the film is pressed onto a second edge portion (not shown) of the stethoscope head. The second edge portion is located radially on a different portion of the stethoscope head. The radius of the second lobe may be configured to increase the contact area between the film and the second edge portion of the stethoscope head.

Figure 8D:
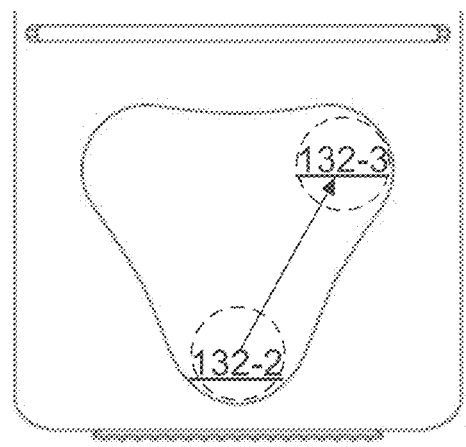
Figure 13:
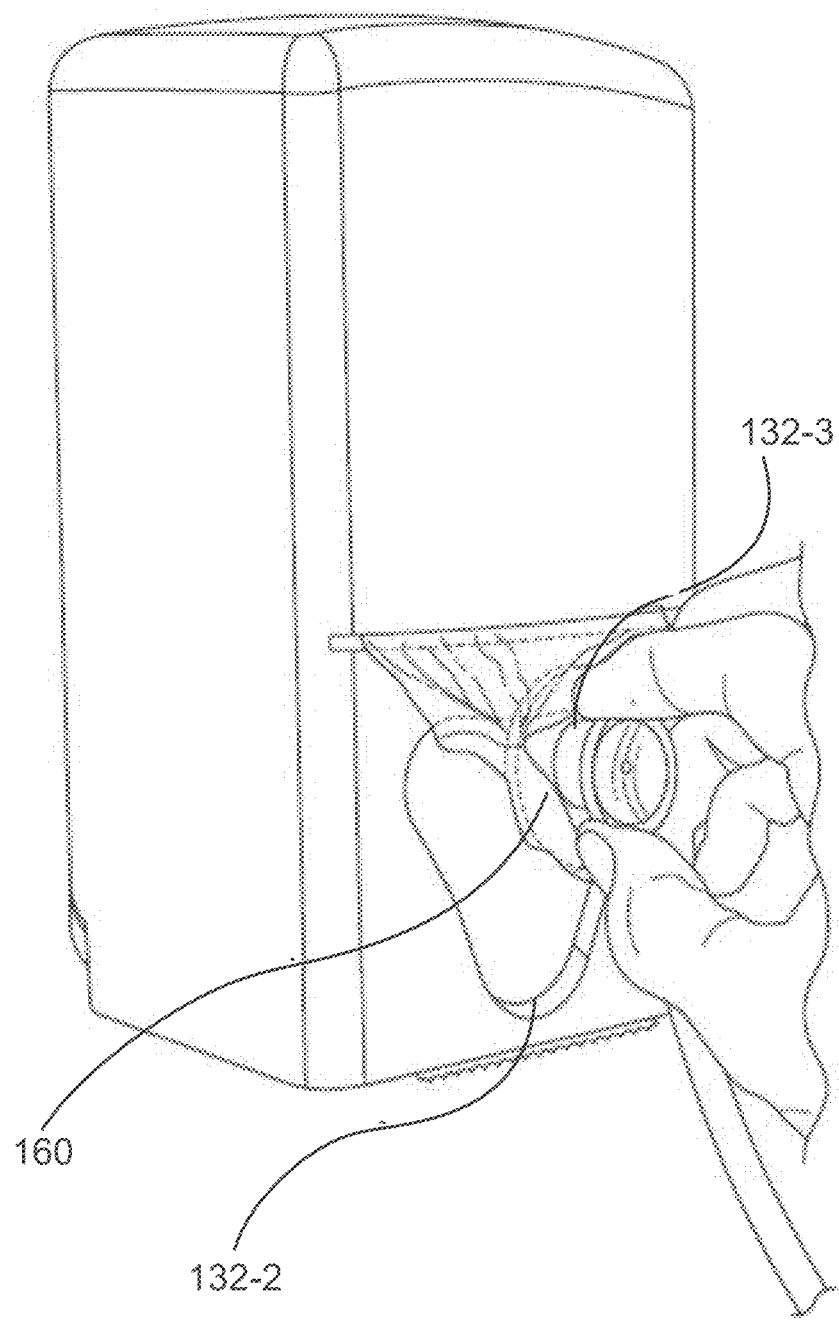

Next, referring to FIGS. 13 and 8D, the user may slide the stethoscope head with the film from the second lobe 132-2 to the third lobe 132-3 located at the top right corner of the recess. When the user pushes the stethoscope head against the third lobe, a third portion of the film is pressed onto a third edge portion (not shown) of the stethoscope head. The radius of the third lobe may be configured to increase the contact area between the film and the third edge portion of the stethoscope head. As shown in FIG. 13, the film is lifted up and moves with the stethoscope head when the stethoscope head is moved from the second lobe to the third lobe, and a portion of the recess may be exposed.

Figure 8E:
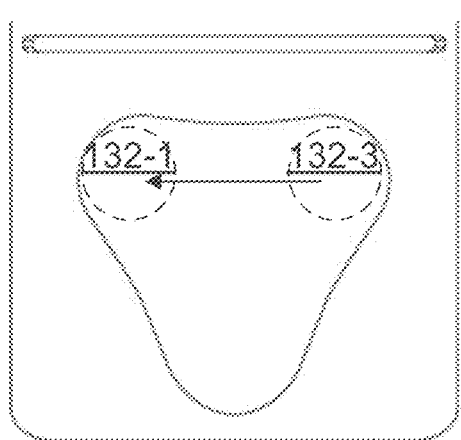
Figure 8F:
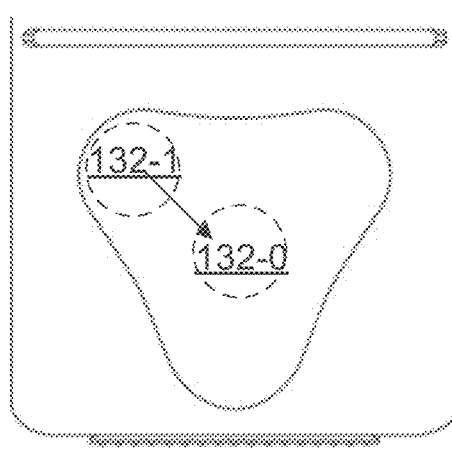
Figure 14:
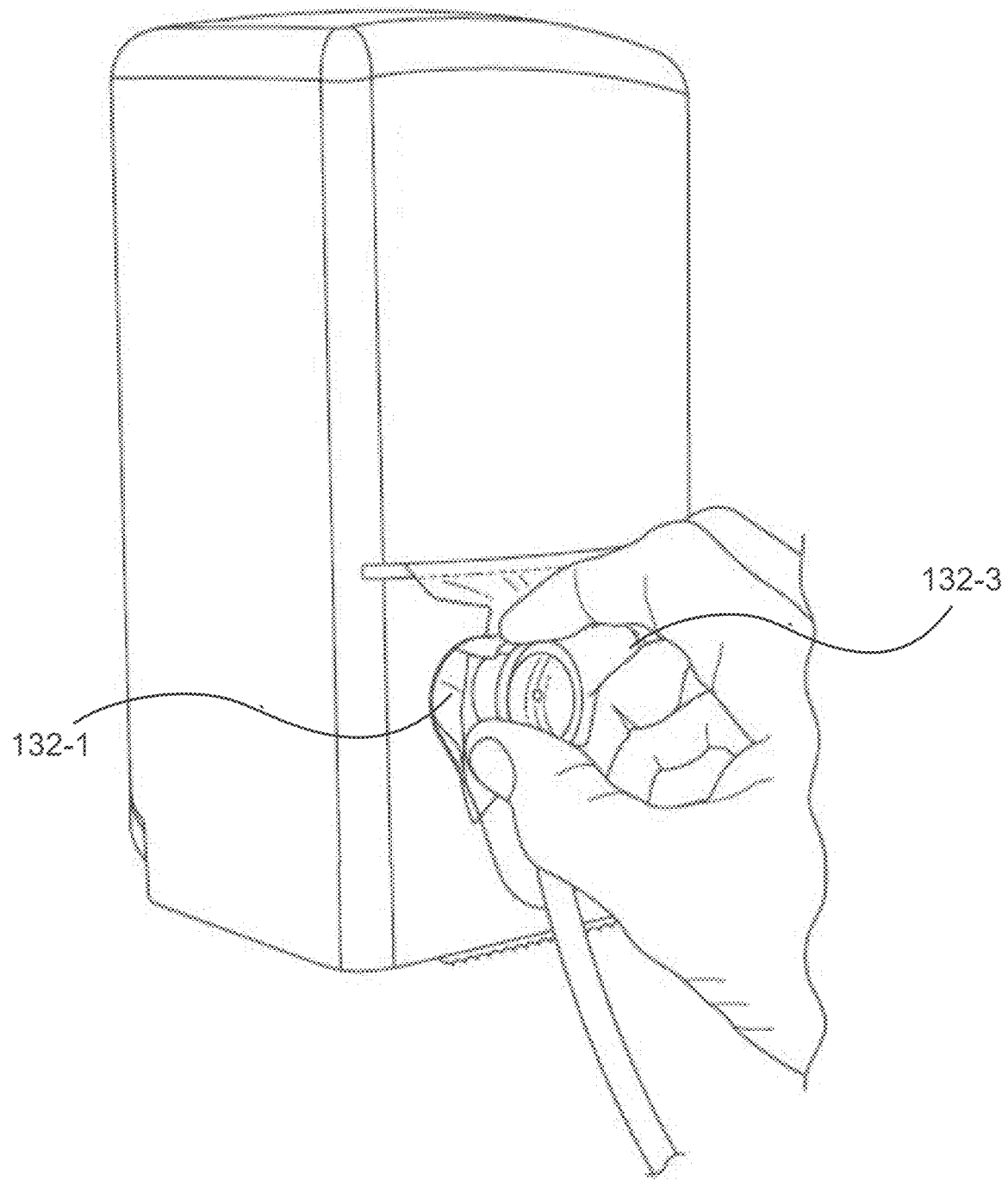

Next, referring to FIGS. 14 and 8E, the user may slide the stethoscope head with the film from the third lobe 132-3 back to the first lobe 132-1 located at the top left corner of the recess. Accordingly, the stethoscope head has moved (translated and/or rotated) in 360-degree counterclockwise within the recess between the lobes. This movement of the stethoscope head between the different lobes causes the film to wrap around different edge portions of the stethoscope head, thereby securing the film to the stethoscope head to form a barrier 152. An operator may slide the stethoscope along all or any portion of the path described herein.

Figure 15:
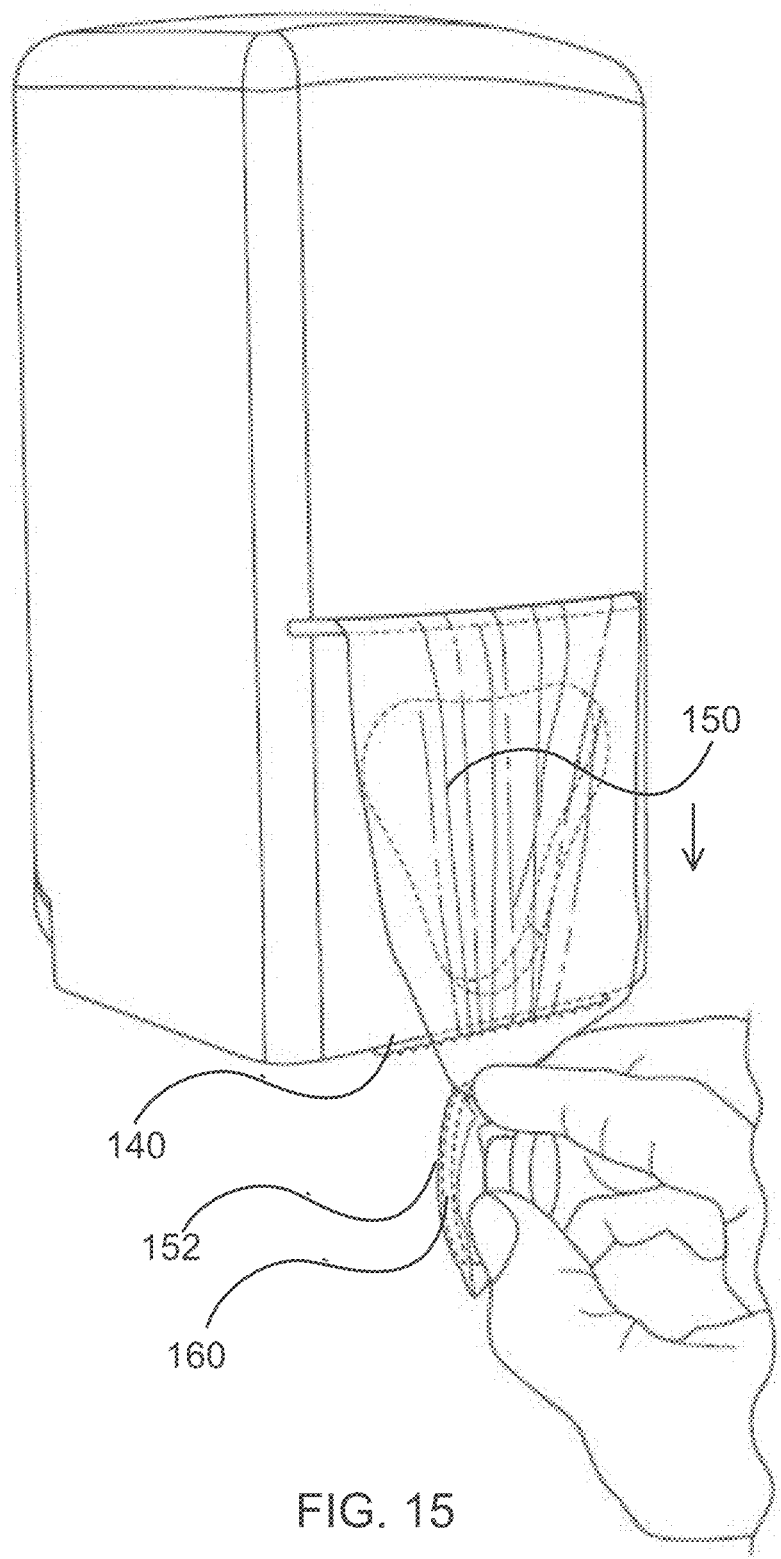
Figure 16A:
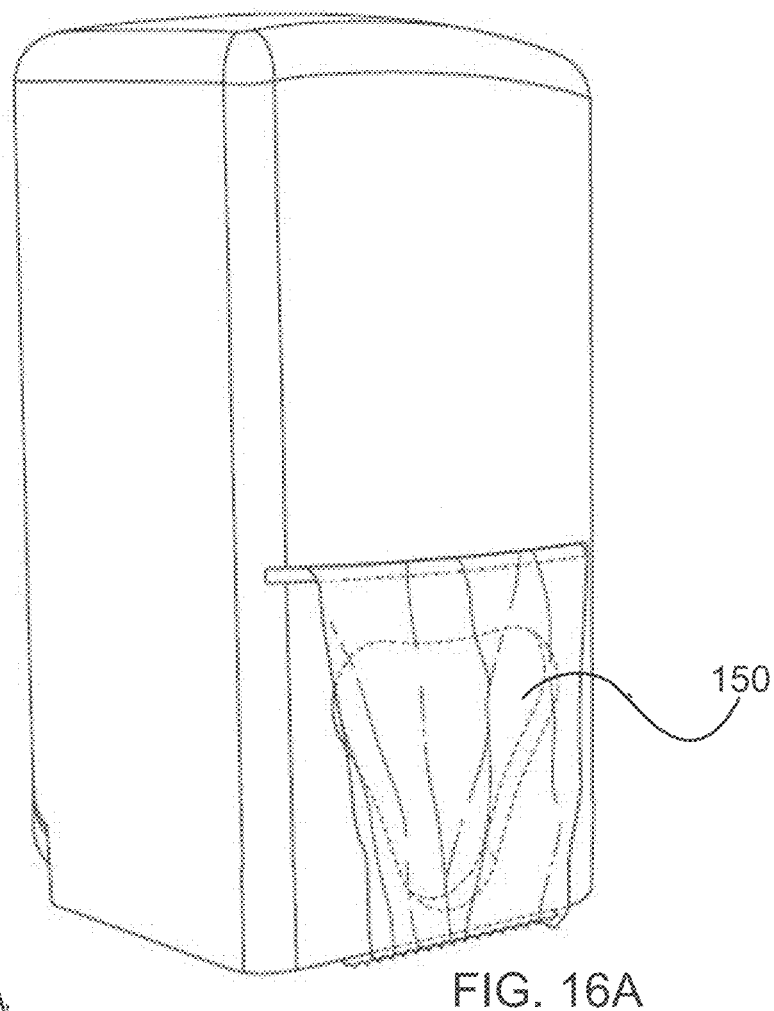
FIG. 16A is a perspective view showing the film after on the dispenser after the stethoscope head and the barrier have been released.
Figure 16B:
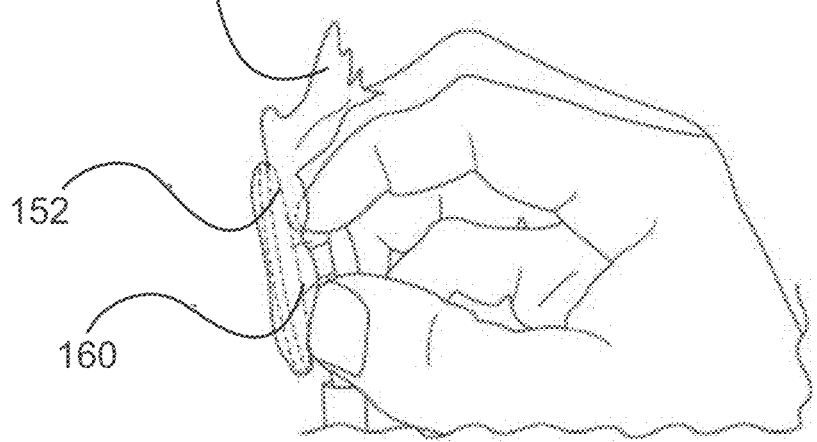
FIG. 16B is a perspective view showing the barrier being applied to the stethoscope head.
Figure 17:
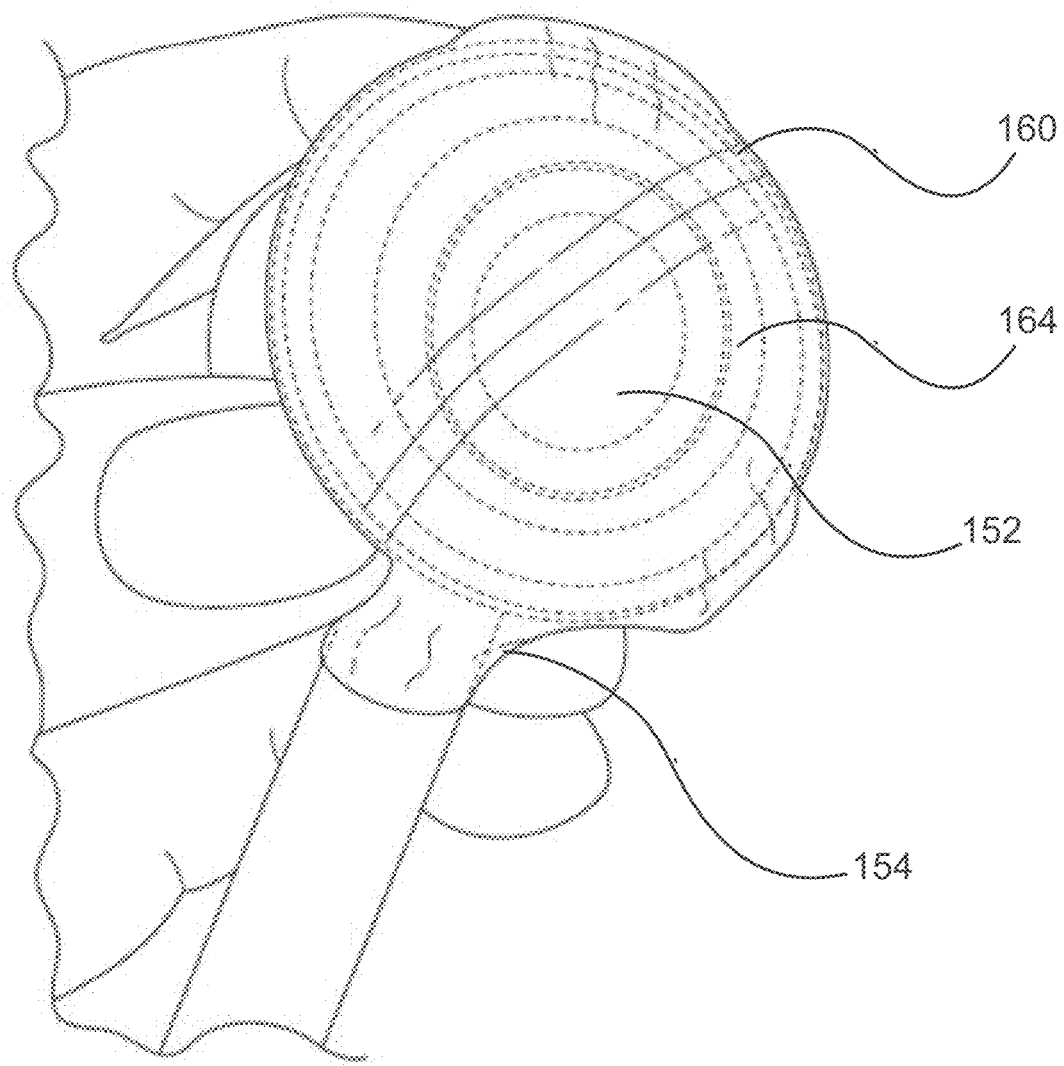
Figure 18:
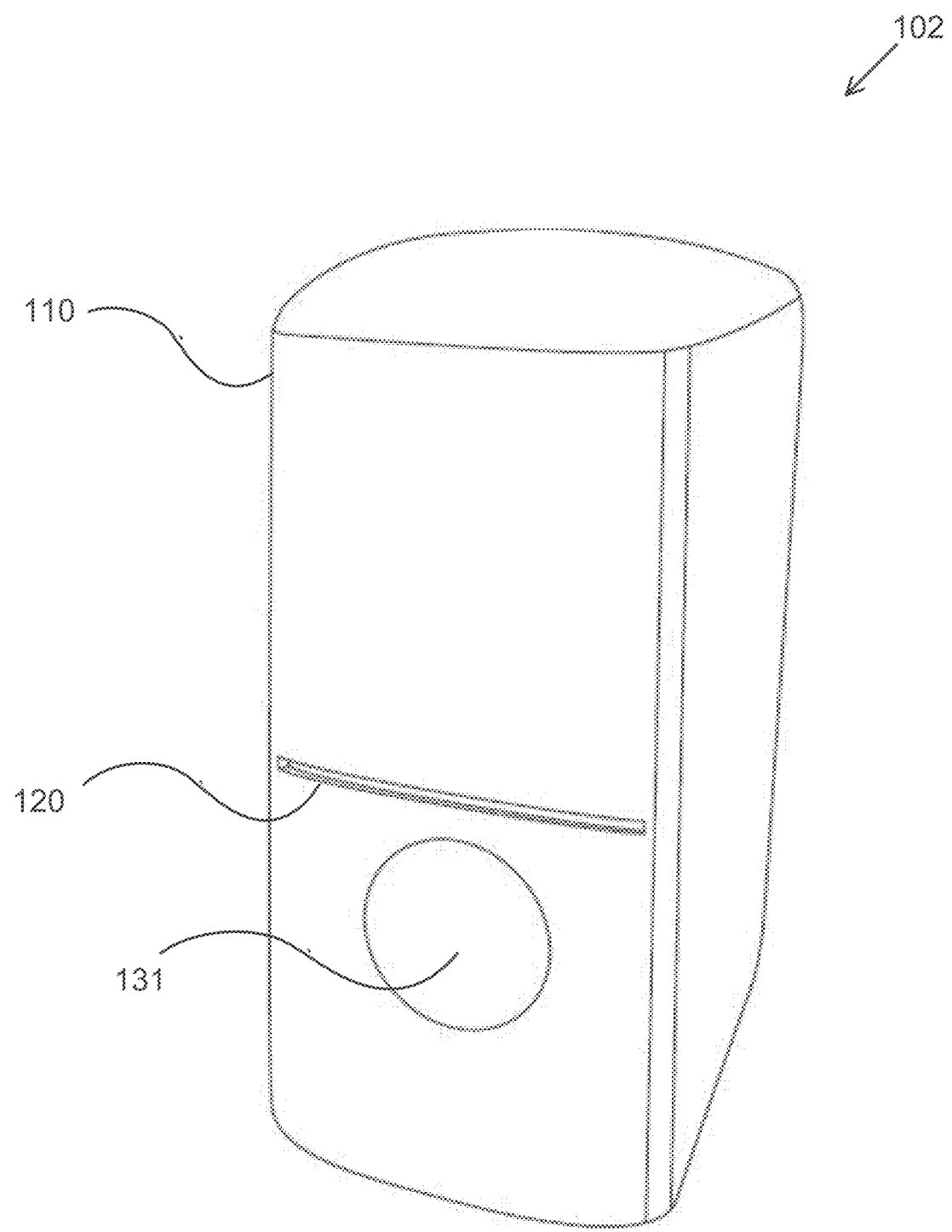
FIG. 18 is a front view of a barrier dispenser in accordance with another embodiment.

Next, the user may slide the stethoscope head with the film from the first lobe 132-1 to the center 132-0 of the recess (see FIG. 8F), and remove the stethoscope head from the recess with the film wrapped around the stethoscope head with a hand (or gloved hand) using their fingertips (e.g., thumb, index finger, middle finger). The dispenser may be configured to be used by any user, independent of whether the user is right or left-handed. The user may then pull the stethoscope head and the film downwards until the stethoscope head is below the cutting edge 140, as shown in FIG. 15. Once there is sufficient clearance, the user may cut the film with the cutting edge or by tearing perforations in the film, to release the wrapped stethoscope head, as shown in FIGS. 16A and 16B. In some cases, any excess film or loose hanging flaps 154 of the film can be tucked by the user and wrapped around an upper portion of the stethoscope head prior to use. The film that is wrapped around the stethoscope head constitutes as a protective barrier 152 as described elsewhere herein. FIG. 17 shows the barrier 152 as applied to the stethoscope head, with the excess film 154 tucked in by the user's fingers. The barrier may be formed as a smooth layer covering a distal surface 164 of the stethoscope head 160. The barrier may be formed with few or no creases (airgaps) between the film and the distal surface of the stethoscope head. The barrier may be formed without the user contacting the distal surface of the stethoscope head. The barrier may also be formed without the user contacting any part of the film/barrier that is applied to the distal surface of the stethoscope head. This can help to reduce contamination and risk of infection to both the user (e.g., healthcare personnel) and the patients. The barrier may be disposable and configured for a single use or patient encounter. FIG. 18 is a front view of a barrier dispenser in accordance with another embodiment. The dispenser 102 is similar to the dispenser 100 described elsewhere herein except for the following differences. In FIG. 18, a recess 131 of the dispenser 102 may have a substantially circular shape instead of a triangular shape. The recess 131 may be sized to receive a variety of types of stethoscope heads. For example, a dimension (e.g., diameter) of the recess may be at least 5%, 10%, 15%, 20%, 25%, 30%, 35%, 40%, 45%, or 50% greater than a dimension (e.g., diameter) of a stethoscope head. As shown in FIG. 18, the cutting edge may be optionally omitted, for example when the source of film is provided as separate sheets, individual sheets, or when the source of film includes perforations that allow sheets of film to be easily and manually separated by the user by hand.

Figure 19:
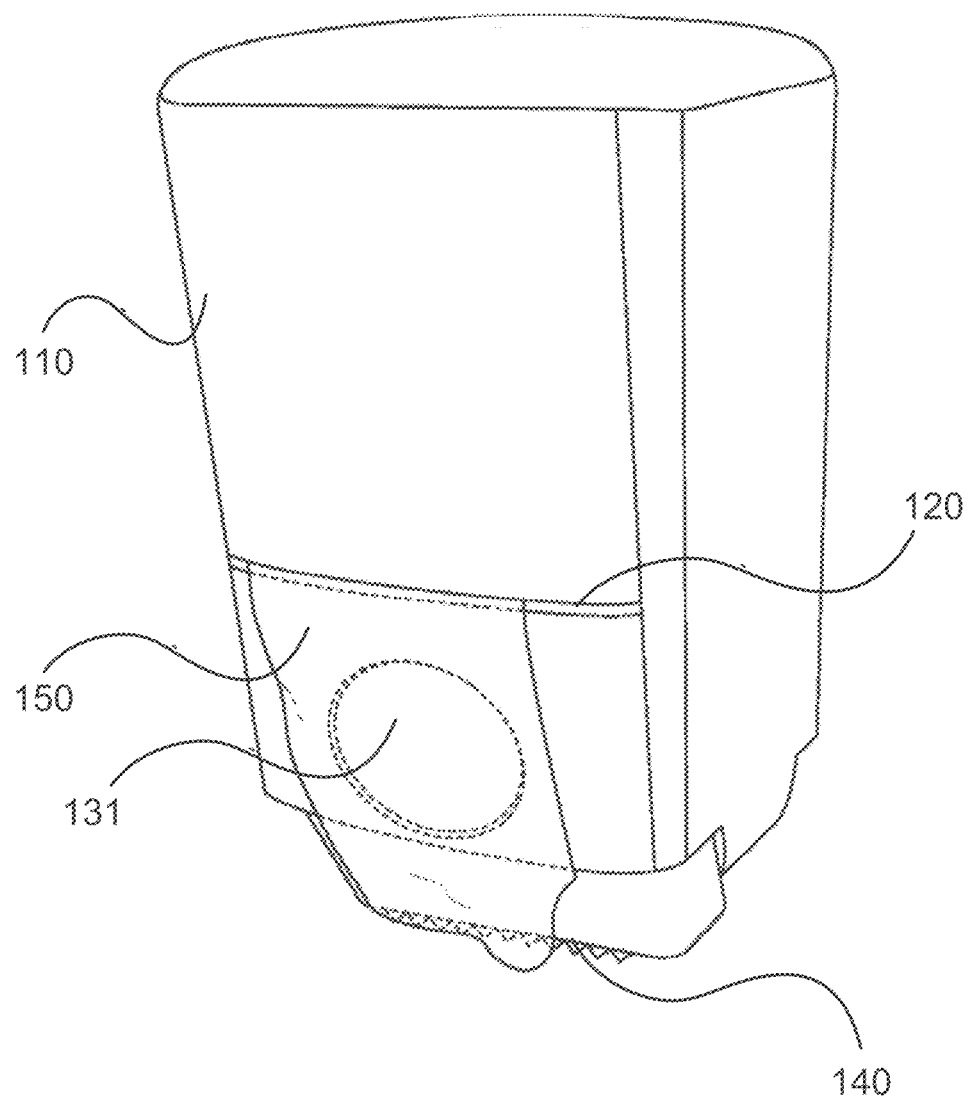
FIG. 19 is a front view of a barrier dispenser showing a film hanging in proximity to a substantially circular-shaped recess.

FIG. 19 is a front view of a barrier dispenser showing a film hanging in proximity to a substantially circular-shaped recess. The film 150 may be dispensed from the opening 120 such that it hangs or drapes over the recess 131. The extended portion of the film may completely cover the recess. In some cases, the film need not completely cover the recess, and may leave one or more portions of the recess exposed. A width of the film may be greater than, equal to, or less than the diameter of the recess. For example, in FIG. 19, the width of the film may be greater than the diameter of the recess although the invention is not limited thereto. In some cases, the width of the film may be equal or less than the diameter of the recess. In the example of FIG. 19, a cutting edge 140 may be optionally included with the dispenser. In some cases, a cutting edge may not or need not be required. In such cases, the film may also be perforated and may comprise a continuous set of films, end to end, each being perforated to separate one from the next.

Figure 20:
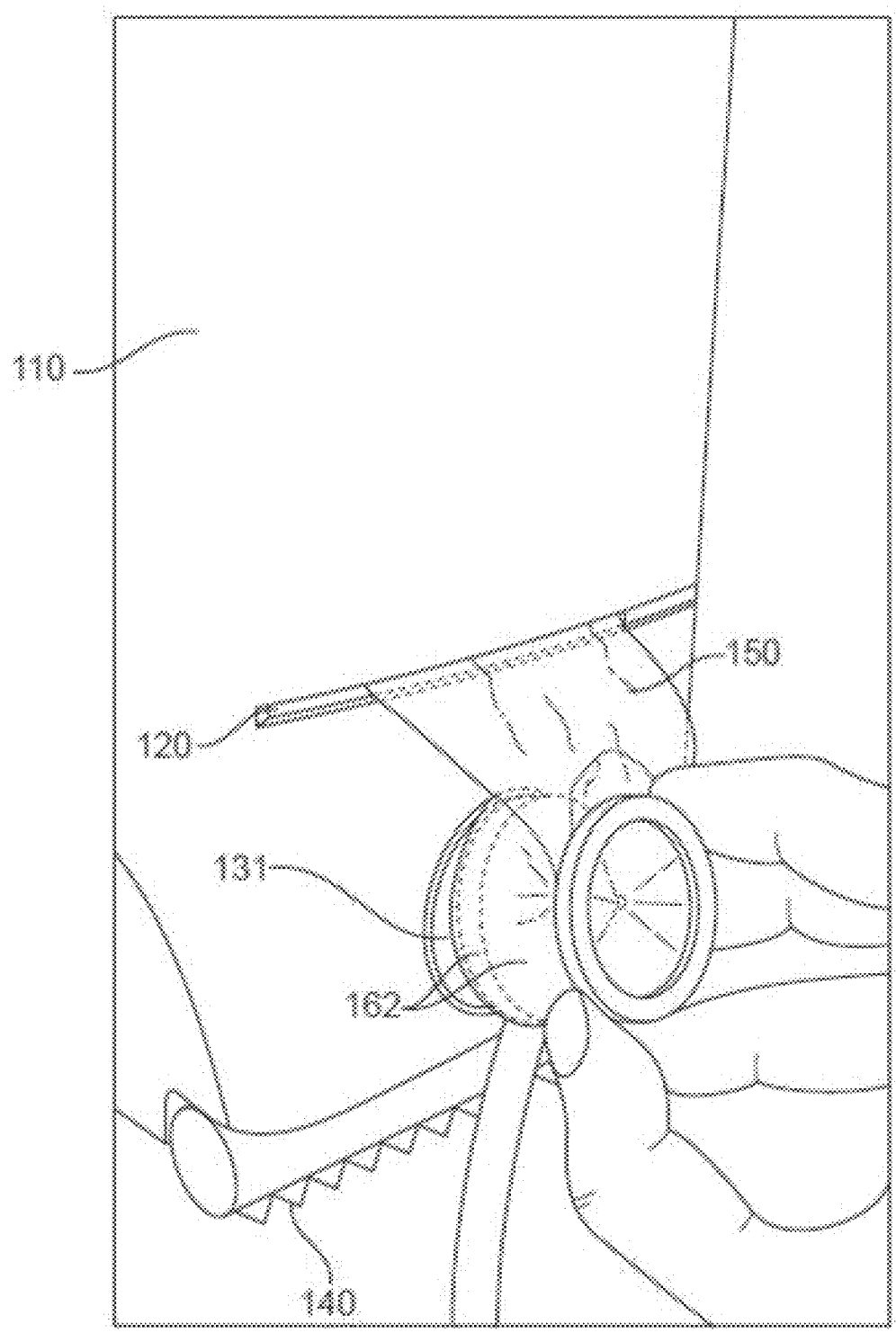
FIG. 20 is a perspective view showing a barrier being applied to a stethoscope head using the dispenser of FIG. 19.

FIG. 20 is a perspective view showing a barrier being applied to a stethoscope head using the dispenser of FIG. 19. A user may place the stethoscope head 160 onto a portion of the film 150 in front of the recess 131. Next, the user may push the stethoscope head with the film into the recess, with the film located in-between the stethoscope head and the recess. The stethoscope head may be placed, for example at or near the center of the recess. The film may be applied onto a distal surface of the stethoscope head when the user pushes the stethoscope head against the bottom surface of the recess. The film may easily attach to the stethoscope head such that light compression of the film causes the film to stick to the stethoscope head. The user may move the stethoscope head with the film within the recess, for example by rotating in a clockwise or counterclockwise manner in order to wrap the film around an edge portion 162 of the stethoscope head in one continuous sweeping motion, or with multiple smaller clockwise or counter clockwise sweeping directions. The stethoscope head with the film may be rotated by an angle within the recess ranging from about 10 degrees to about 360 degrees. In some cases, the user may simply push the stethoscope head with the film into the recess, and tuck any excess film around an upper portion of the stethoscope head, without any rotation of the stethoscope head in the recess.

After the film is wrapped around the stethoscope head to form a barrier, using the fingertips of the hand, the user may remove the stethoscope head with the film from the recess. The user may then pull the stethoscope head and the film downwards until the stethoscope head is below the cutting edge 140, for example as previously described with reference to FIG. 15. Once there is sufficient clearance, the user may cut the film to release the stethoscope head with the applied barrier, as previously described reference to FIGS. 16A and 16B. In some cases, any excess film or loose hanging flaps of the film can be tucked by the user and wrapped around an upper portion of the stethoscope head prior to use. The film that is wrapped around the stethoscope head constitutes as a protective barrier as described elsewhere herein. As previously described, no cutter or cutting may be necessary if the film comprises perforated film, or if interleaved stacked sheets or a cassette is used instead of a roll of film.

Figure 21:
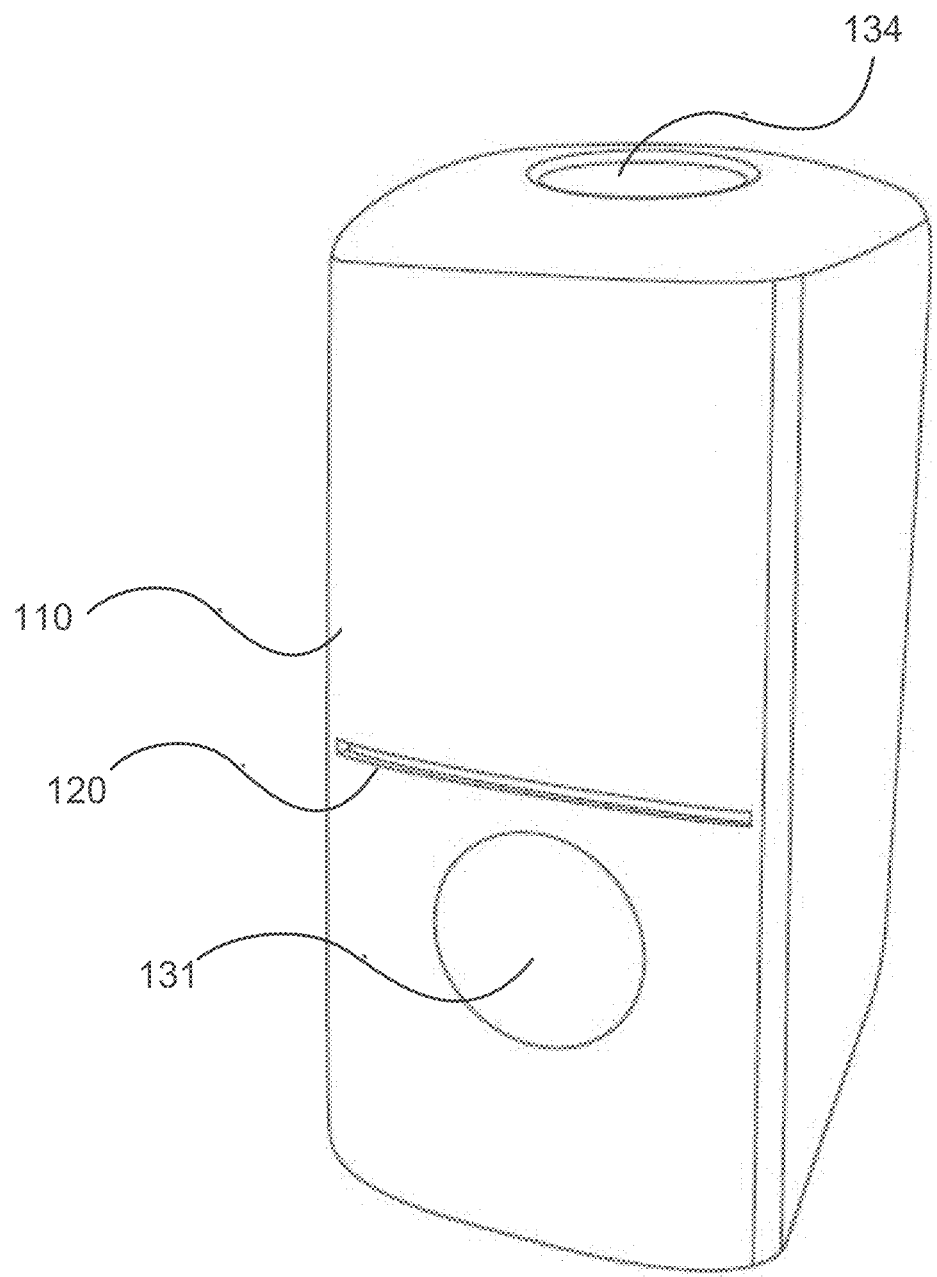
FIGS. 21 and 22 are perspective views showing a recess for flattening or smoothing the film after it has been applied to the stethoscope head.
Figure 22:
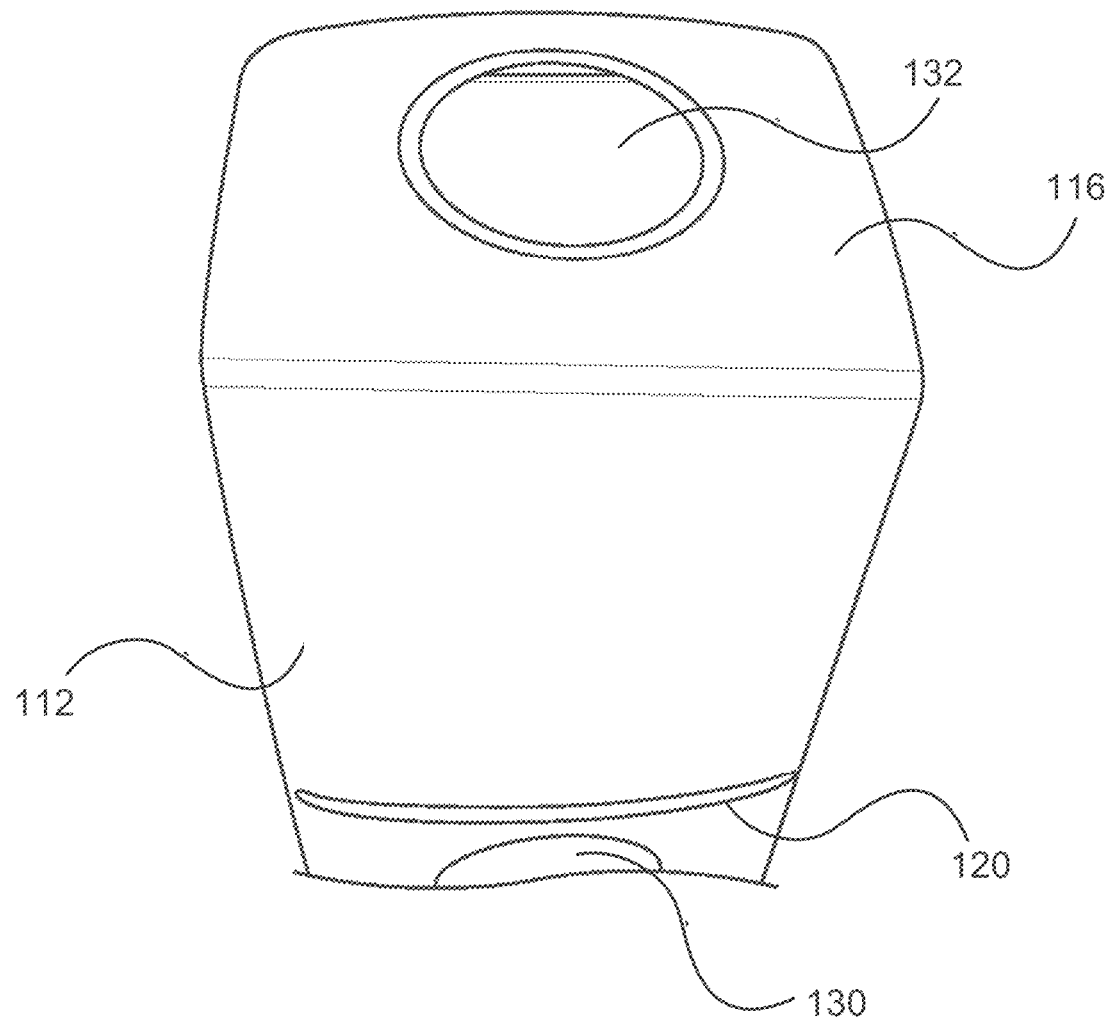

Optionally in any of the embodiments disclosed herein, the dispenser may further include one or more areas for flattening or smoothing the film after it has been applied to the stethoscope head. For example, referring to FIGS. 21 and 22, a recess 134 may be provided on a top portion of the housing 110, in addition to the recess 131 (or recess 130) on the front portion of the housing. The recess 130/131 can be used for applying the film to the stethoscope head to form a barrier as described elsewhere herein and may be employed in any of the dispensers described herein. The recess 134 can be used for flattening or smoothing the film/barrier after it has been applied to the stethoscope head. Optionally in any of the embodiments disclosed herein, the recess 134 may include an anti-microbial material for disinfecting or sterilizing the stethoscope head before and/or after patient use. The anti-microbial material may be a liquid or gel-like material that is coated onto the barrier. Optionally in any of the embodiments disclosed herein, an energy source (e.g., an ultraviolet illumination source) for reducing the amount of microorganisms, disease, virus, cellular, or bacteria on the stethoscope head and the barrier may be provided in the recess 134. Additional details about the energy source are described elsewhere herein, for example with reference to FIG. 24.

Figure 23A:
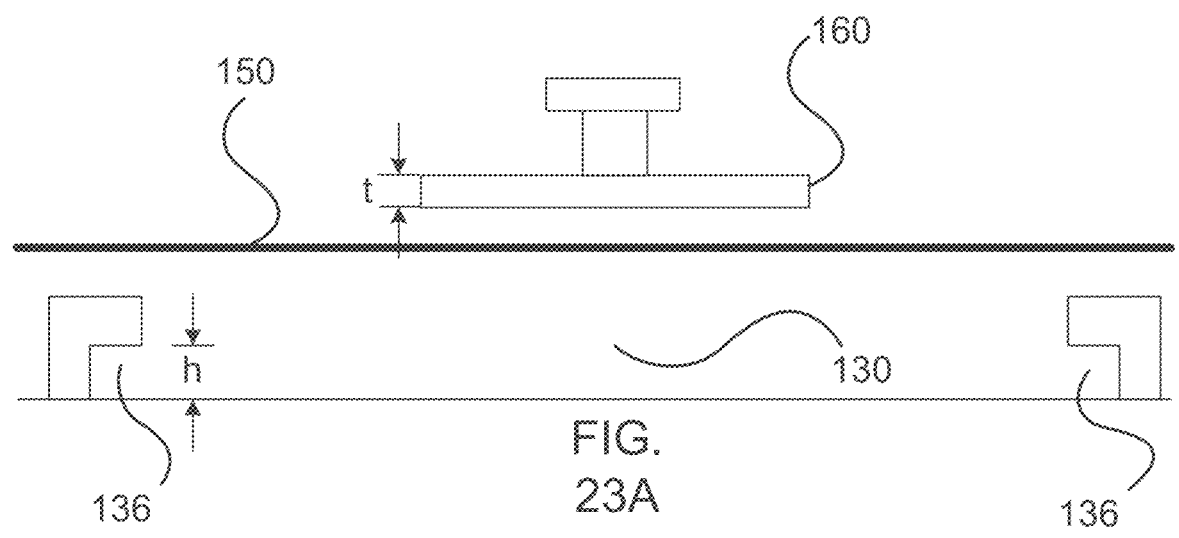
FIGS. 23A through 23C are schematic cross-sectional views showing a recess comprising an undercut region, and an exemplary method of applying the film to the stethoscope head with aid of the undercut regions to form the barrier.
Figure 23B:
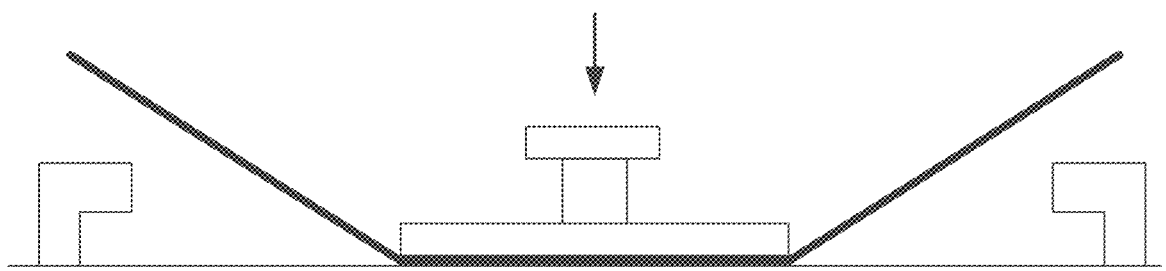
Figure 23C:
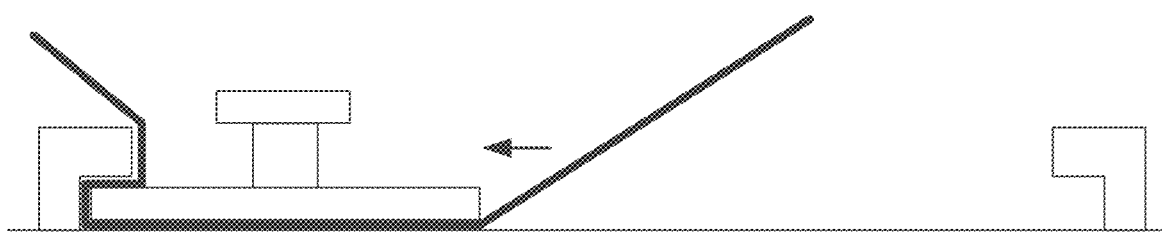

Optionally in any of the embodiments of dispensers disclosed herein, the dispenser may include a recess comprising an undercut region. The undercut region may extend along a periphery of the recess. In some cases, the undercut region may be provided at the corners of the recess (e.g., at the rounded concave lobes). FIG. 23A is a schematic cross-sectional view of a recess 130 comprising one or more undercut regions 136 in accordance with any of the embodiments disclosed herein. FIGS. 23A through 23C additionally show a stethoscope head 160 and film 150 being placed into the recess and moved to an undercut region, thereby causing the film to wrap partially around an edge portion of the stethoscope head to form a barrier. A height h of the undercut region may be configured based on a thickness profile of the stethoscope head. A distal portion of the stethoscope head may have a thickness t. The distal portion of the stethoscope head may be substantially planar. In some cases (not shown), the distal portion of the stethoscope head may have a slight curvature (e.g., slight convex). The height h of the undercut region may be greater than the thickness t of the stethoscope head in order to provide a gap when an edge portion of the stethoscope head is moved into the undercut region. The height h may be greater than the thickness t by at least about 5%, 10%, 15%, or 20%. The gap may be sized based on a thickness of the film to be applied to the stethoscope head. The film may abut against the surface of the undercut region and the stethoscope head when the edge portion of the stethoscope head is moved to the undercut region. As shown in FIG. 23C, translating the edge portion of the stethoscope head into the undercut region within the recess can cause the film to wrap around the edge portion of the stethoscope head. This is advantageous in improving adhesion of the film to the stethoscope head since the film can be wrapped around different edge portions of the stethoscope head, for example by moving the stethoscope head in a sequential manner between the undercut regions of rounded concave lobes.

Figure 24:
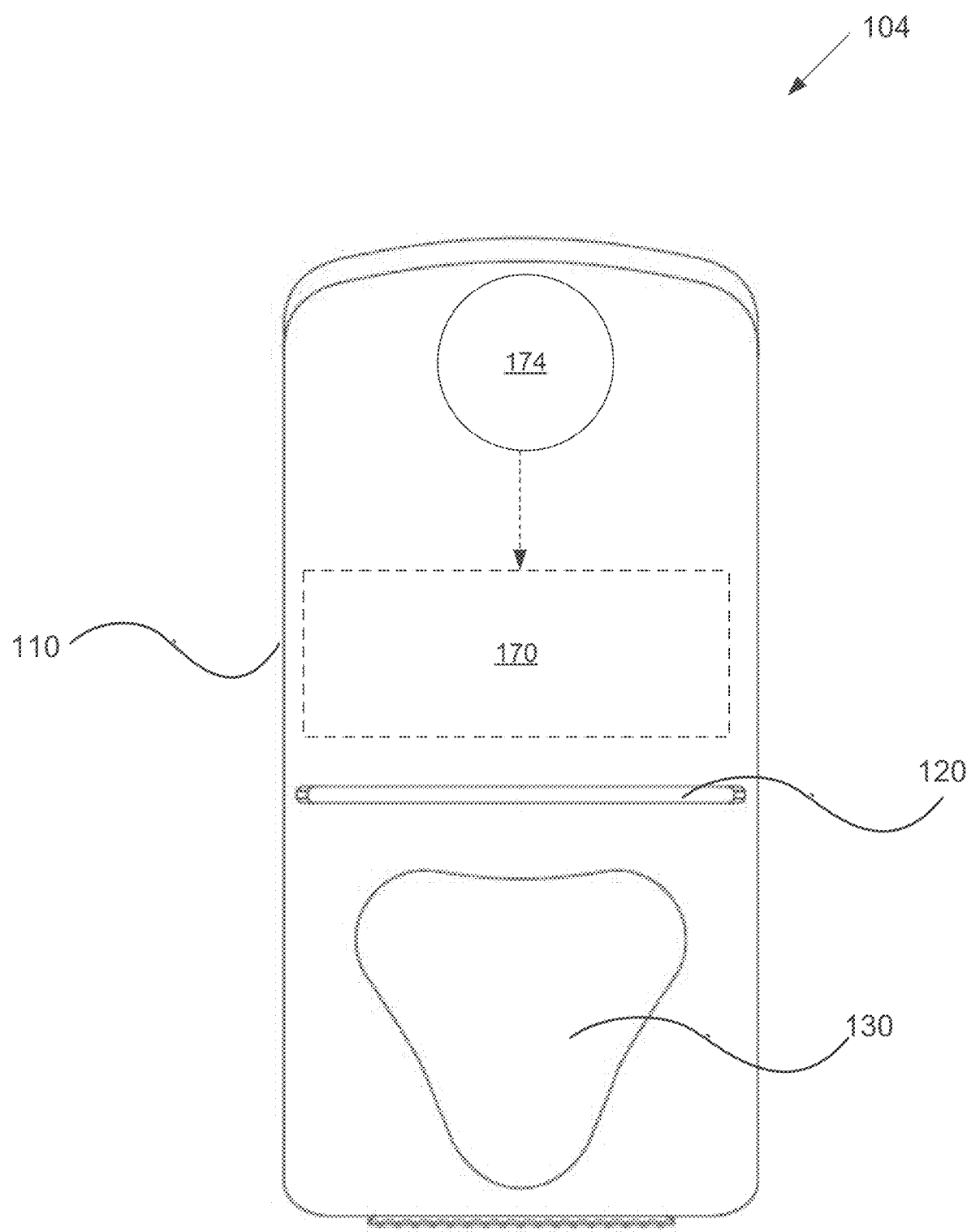
FIG. 24 is a perspective view of a barrier dispenser comprising an energy source, in accordance with an embodiment.

FIG. 24 is a perspective view of a barrier dispenser comprising an energy source, in accordance with any of the embodiments disclosed herein. The dispenser 104 may include an energy source 170. The energy source can be disposed within the chamber of the housing as described in one or more embodiments elsewhere herein. The energy source 170 may be powered by a power supply 174. FIG. 24 shows the power supply located onboard the dispenser although the invention is not limited thereto. In any of the embodiments disclosed herein, the power supply may be located remotely to the dispenser.

The energy source 170 can be configured to illuminate the stethoscope head for disinfecting or sterilizing the stethoscope head, that can apply to any of the embodiments disclosed herein. The energy source may be configured to emit one or more wavelengths of light that can kill microorganisms, disease, virus, cellular, or bacteria on the stethoscope head. The energy source may include, for example an antimicrobial ultraviolet (UV/UV-C/regular light) light source. The energy source may include, for example one or more UV light/regular light emitting diodes (LEDs). The energy source may include a germicidal lamp. The illumination by the energy source can be used to help control the level of microorganisms, disease, virus, cellular, or bacteria on the stethoscope head present on and around the stethoscope head and film/barrier. Most common microorganisms, disease, virus, cellular, or bacteria organisms that can cause sickness and disease in humans can be killed with moderate doses of ultraviolet light having a wavelength between about 260 nm and about 280 nm. Accordingly, the energy source may be configured to emit ultraviolet light having a wavelength between about 260 nm and about 280 nm, up to 350 nm. The UV light may be pulsed or continuous. Depending upon the formulation of the film, oxygen may be generated from the film upon exposure to light or UV light.

The energy source 170 may be powered by the power supply 174. The power supply may include external power, one or more batteries, solar power means, light power means, capacitors or any other energy storage device. In any of the embodiments described herein, the energy source 170 may comprise a UV light source or other light source comprising one or more UV-LEDs or regular LEDs. The power supply 174 may comprise a solar panel configured to power the UV light source. The solar panel may comprise one or more solar energy cells. The solar panel can be mounted on the dispenser, for example on a front, side or top portion of the housing 110. The solar panel can be mounted to for optimal exposure to sunlight or other forms of electromagnetic radiation. The solar panel may include monocrystalline silicon or any other semiconductor materials for harnessing solar energy. In some cases, the solar panel may be configured to output power, for example 0.2 W or lower or higher. The solar panel can be configured to provide any power output, depending on the size of the chamber, the amount or thickness of the barrier material to be irradiated, the type of barrier material, etc. The solar panel may be formed having any shape, size and/or design to match the housing, and can be located on a portion of the housing that does not interfere with the barrier dispensing operation of the dispenser or the operation of the solar panel.

The energy source may be activated by a switch, automatically triggered when film is advanced, or continuously exposing the barrier supply to UV/UV-C or other light source. For example, a user may turn on the switch to power on the energy source to disinfect the stethoscope head and the film/barrier, or automatically triggered when film is advanced. Alternatively, the energy source may be configured to automatically power on when the stethoscope head and the film/barrier are brought into proximity to the energy source. The energy source may also remain on all the time, or periodically through use or by timer.

Optionally in any of the embodiments disclosed herein, the energy source may be mounted to an outer surface of the housing 110 such that the energy source can illuminate ultraviolet light onto the stethoscope head and the film/barrier, after the film has been dispensed from the dispenser and applied to the stethoscope head. This configuration may permit the stethoscope head and the applied barrier to be treated with the ultraviolet light immediately prior to use with a patient.

Optionally in any of the embodiments disclosed herein, the housing 110 may include a cavity configured to support the energy source therein. An opening (for example, any of recesses 130, 131 and 134) may be provided, through which the stethoscope head and the applied barrier can be inserted into the cavity to help control the level of microorganisms, disease, virus, cellular, or bacteria on the stethoscope head present on and around the stethoscope head and film/barrier using the energy source.

Optionally in any of the embodiments disclosed herein, the stethoscope head and the film/barrier may be made of substantially ultraviolet light-resistant materials, to prevent degradation of the stethoscope head and the film as a result of the UV/UV-C illumination or other light source. Examples of UV/UV-C and/or other light source light-resistant materials can include glasses, metals, silicones, and ultraviolet light resistant polymers.

Optionally in any of the embodiments disclosed herein, the energy source may be configured to emit one or more wavelengths of light for curing the film after the film has been applied to the stethoscope head to form the barrier. The curing of the film can help to improve the adhesion of the film to the stethoscope head, and prevent the film from peeling off during use. The one or more wavelengths may include infrared light, for example that provides heat to cure the film.

Figure 25:
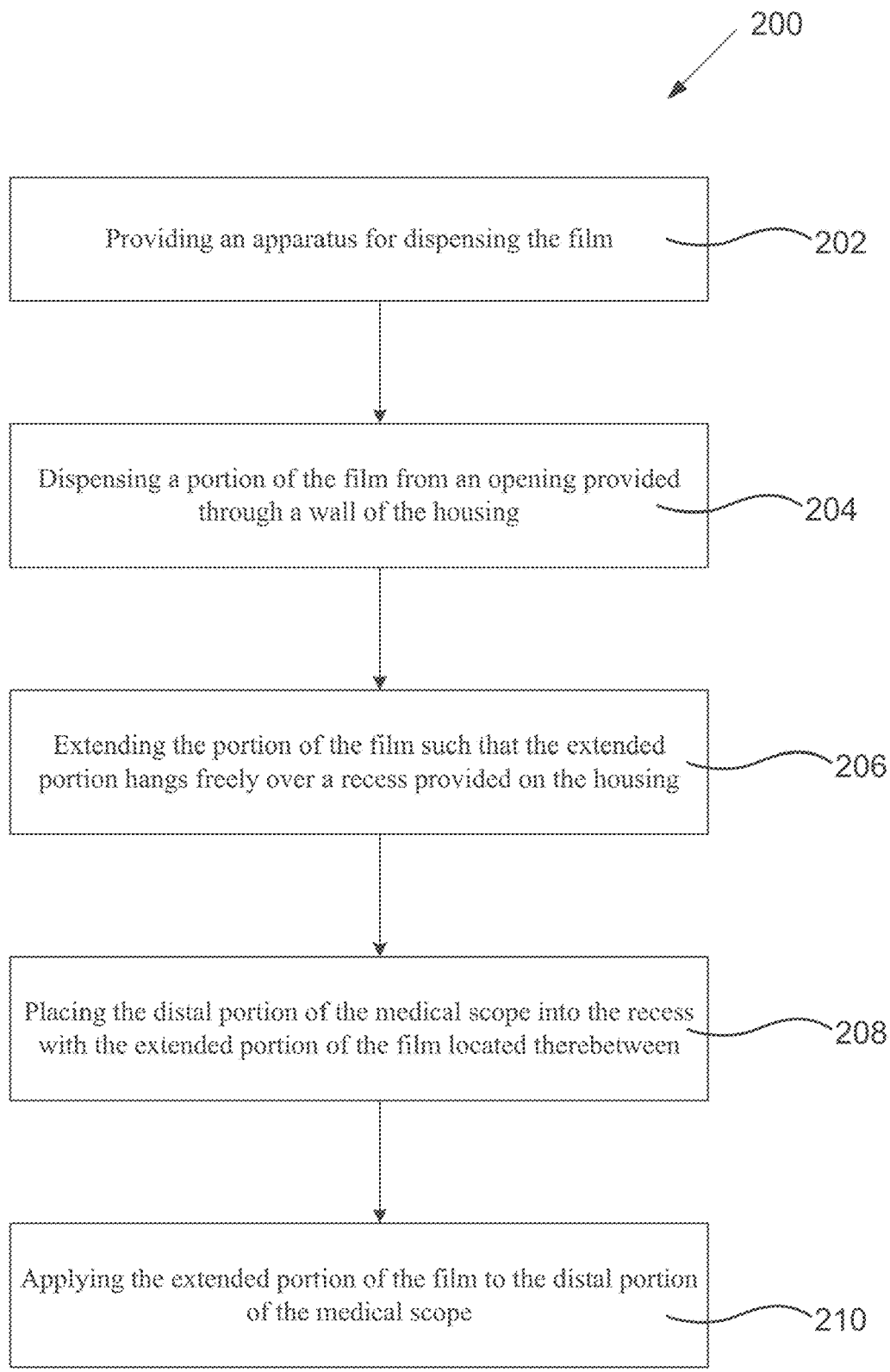
FIG. 25 is a flowchart illustrating a method of dispensing a film for use with a medical scope, in accordance with an embodiment.
Figure 26A:
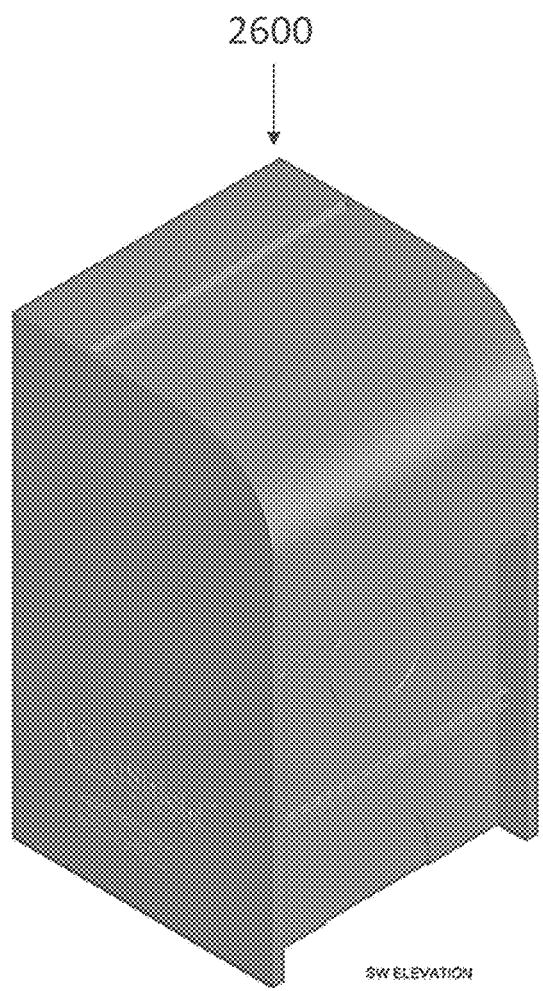
Figure 26B:
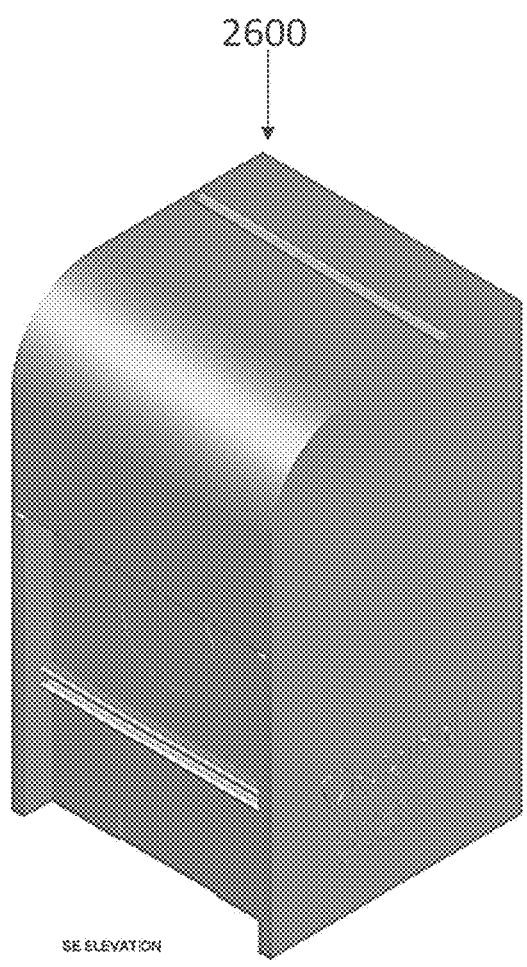

FIG. 25 is a flowchart illustrating a method 200 for dispensing a film for use with a medical scope, that may apply to any of the embodiments disclosed herein. The method may be performed by one or more users, for example healthcare personnel in one or more medical environments as described elsewhere herein. The method can be used to apply a film onto a medical scope to form a protective barrier. An apparatus may include a chamber configured to receive and support therein a source of film. The method may include providing 202 an apparatus for dispensing the film; dispensing 204 a portion of the film from an opening provided through a wall of the housing; extending 206 the portion of the film such that the extended portion hangs freely over a recess provided on the housing, wherein the recess is sized to receive a distal portion of the medical scope; placing 208 the distal portion of the medical scope into the recess with the extended portion of the film located therebetween; and applying 210 the extended portion of the film to the distal portion of the medical scope.

Applying the extended portion of the film may comprise moving the distal portion of the medical scope in a translational and/or rotational manner within the recess thereby engaging the extended portion of the film with the medical scope. For example, the distal portion of the medical scope may be translated and/or rotated along a periphery of the recess. Applying the extended portion of the film may also comprise conforming or wrapping the extended portion of the film around the distal portion of the medical scope.

Optionally in any of the embodiments disclosed herein, the recess may be in the shape of a polygon. The polygon may comprise a triangle such that the recess has a substantially triangular shape. Each corner of the recess may have a radius and/or comprise a rounded concave lobe. Applying the extended portion of the film may comprise moving the distal portion of the medical scope within the recess between the corners and/or the rounded concave lobes, so as to cause the extended portion of the film to conform or wrap around the distal portion of the medical scope. For example, the aforementioned step may comprise sliding the distal portion of the medical scope in a smooth manner between the corners and/or the rounded concave lobes within the recess. The aforementioned step may also comprise sliding the distal portion of the medical scope sequentially between the corners and/or the rounded concave lobes within the recess in a clockwise or counterclockwise direction. Applying the extended portion of the film may comprise pressing the distal portion of the medical scope against the extended portion of the film onto a bottom of the recess. Optionally in any of the embodiments disclosed herein, the distal portion of the medical scope may be moved collectively with the extended portion of the film within the recess, so as to wrap the extended portion of the film around the distal portion of the medical scope.

Optionally in any of the embodiments disclosed herein, the method 200 may further include cutting and releasing the extended portion of the film after applying the extended portion of the film to the distal portion of the medical scope. The extended portion of the film can be cut and released using a cutting edge on the housing.

Optionally in any of the embodiments disclosed herein, the step of cutting and releasing the film can be omitted. For example, a roll comprising the film may be segmented into a plurality of pieces coupled together by perforations. The perforations may allow each piece to be manually separated from the rest of the roll for a single use with the medical scope. Accordingly, the method 200 may further include manually separating each piece along the perforations after applying the portion of the film to the distal portion of the medical scope.

Optionally in any of the embodiments disclosed herein, applying the extended portion of the film may further comprise flattening or smoothing the extended portion of the film using one or more areas of the housing.

Optionally in any of the embodiments disclosed herein, the method 200 may further comprise disinfecting or sterilizing the distal portion of the medical scope using antimicrobial, antiviral, antipathogenic, or antibacterial material provided in the film. The antimicrobial, antiviral, antipathogenic, or antibacterial material may also be provided on one or more portions of the housing, for example in one or more recesses of the housing.

Optionally in any of the embodiments disclosed herein, the method 200 may further comprise illuminating the distal portion of the medical scope with an energy source thereby disinfecting the distal portion of the medical scope. The energy source may be configured to emit ultraviolet (UV/UV-C) light or other light using other light sources as described elsewhere herein.

Optionally in any of the embodiments disclosed herein, the method 200 may further comprise curing the extended portion of film using an energy source after applying the extended portion of the film to the distal portion of the medical scope, so as to improve an adhesion strength of the film.

One or more of the previously-described embodiments, for example application of the barrier to the stethoscope head (see, e.g., FIGS. 10-17 and 20), can be easily performed using gloved hands (partial or fully gloved) or bare hands, while ensuring that a protective barrier can be properly applied to the stethoscope head. As previously described, the barrier can be used to reduce or eliminate contamination to a stethoscope head or drum. The barrier can be used to reduce the risk of microbial, bacterial, viral, disease, or pathogenic transmissions between patients and/or users. The barrier can be an antimicrobial, antiviral, antipathogenic, or antibacterial barrier. The barrier can serve as an antimicrobial, antiviral, antipathogenic, or antibacterial barrier for the stethoscope head. The barrier may include an antimicrobial, antiviral, antipathogenic, or antibacterial substance that can neutralize or destroy microbes, organic matter, contain disinfectants, metals, or a combination of both. The barrier can help to reduce or eliminate contamination of the stethoscope head when the stethoscope is being used on multiple patients. The risk of hospital-acquired infections (HAIs) to patients and users (e.g., healthcare personnel) can be significantly reduced, through use of the protective barrier applied using the apparatus and methods described herein.

In another aspect, the present disclosure provides a barrier dispenser comprising a housing with a left side panel, right side panel, and top panel, each of which may comprise a slot. The barrier dispenser may comprise a front panel that is insertable into the slots of the left and right-side panels. The front panel may comprise one or more recessed regions configured to receive a portion of a medical instrument. A source of a barrier material may be supported by the left and right-side panels. The barrier dispenser may comprise a lid cover comprising a roller portion that is insertable into a slot of the top panel. The lid cover may pivot relative to the housing when the roller portion is inserted into the slot of the top panel. The lid cover and the front panel may form a gap through which a portion of the barrier material may extend when the barrier material is dispensed.

The barrier dispenser disclosed herein may provide several advantages over other conventional systems that are commercially available. For instance, the barrier dispensers of the present disclosure may permit a user to quickly and efficiently dispense and cut a desired amount of a barrier material. The barrier dispenser may permit a barrier material to be easily dispensed, applied to a medical tool or instrument, removed from the medical tool or instrument, and disposed of after use, and can provide a cost-effective solution for effectively minimizing the spread of Hospital Acquired Infections. Further, the barrier dispenser may allow a user to easily open the barrier dispenser to replace the barrier material without having to disassemble any portion of the barrier dispenser. The barrier dispensers disclosed herein may also be installed and assembled without the use of additional fasteners or tools, which can reduce the amount of time and effort needed to assemble, disassemble, move, and re-install the barrier dispensers in various different locations. Compared to conventional systems, the barrier dispenser may also provide several key benefits, such as the ability to dispense barrier materials (also referred to herein as "shields" or "films") that are capable of covering an entire head of a scope (as opposed to only a front surface of the scope). This can help to further decrease or potentially eliminate any exposure of the head of the scope to bacteria or pathogens from a patient or a doctor or physician handling the scope. The form factor (i.e., size and/or shape) and material properties of the shield or barrier material may permit a doctor or physician to fully cover a variety of different types of scopes or other instruments having different sizes and/or shapes with the shield or barrier material, thereby providing additional flexibility and enhanced compatibility with different models or brands of scopes. Further, the barrier dispensers may be configured to dispense shields or barrier materials without requiring the use of a separate energy source (e.g., electrical energy from an electrical outlet or one or more batteries), thereby providing a cost-effective solution that improves reliability of dispensing and requires less maintenance compared to other commercially available barrier applicators.

Figure 30:
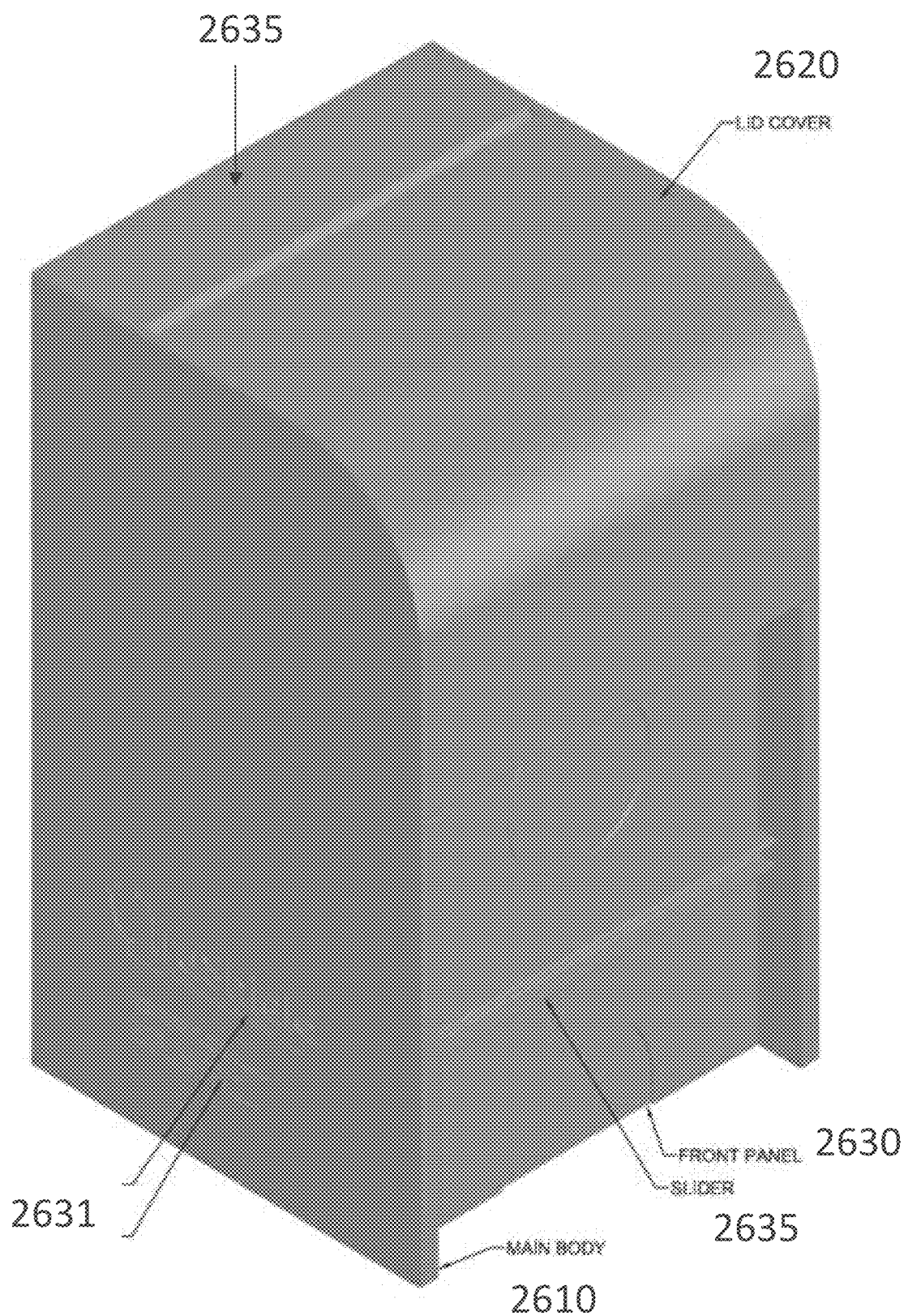
FIGS. 30 and 31 schematically illustrate various features of a main body of a barrier dispenser, in accordance with an embodiment.
Figure 31:
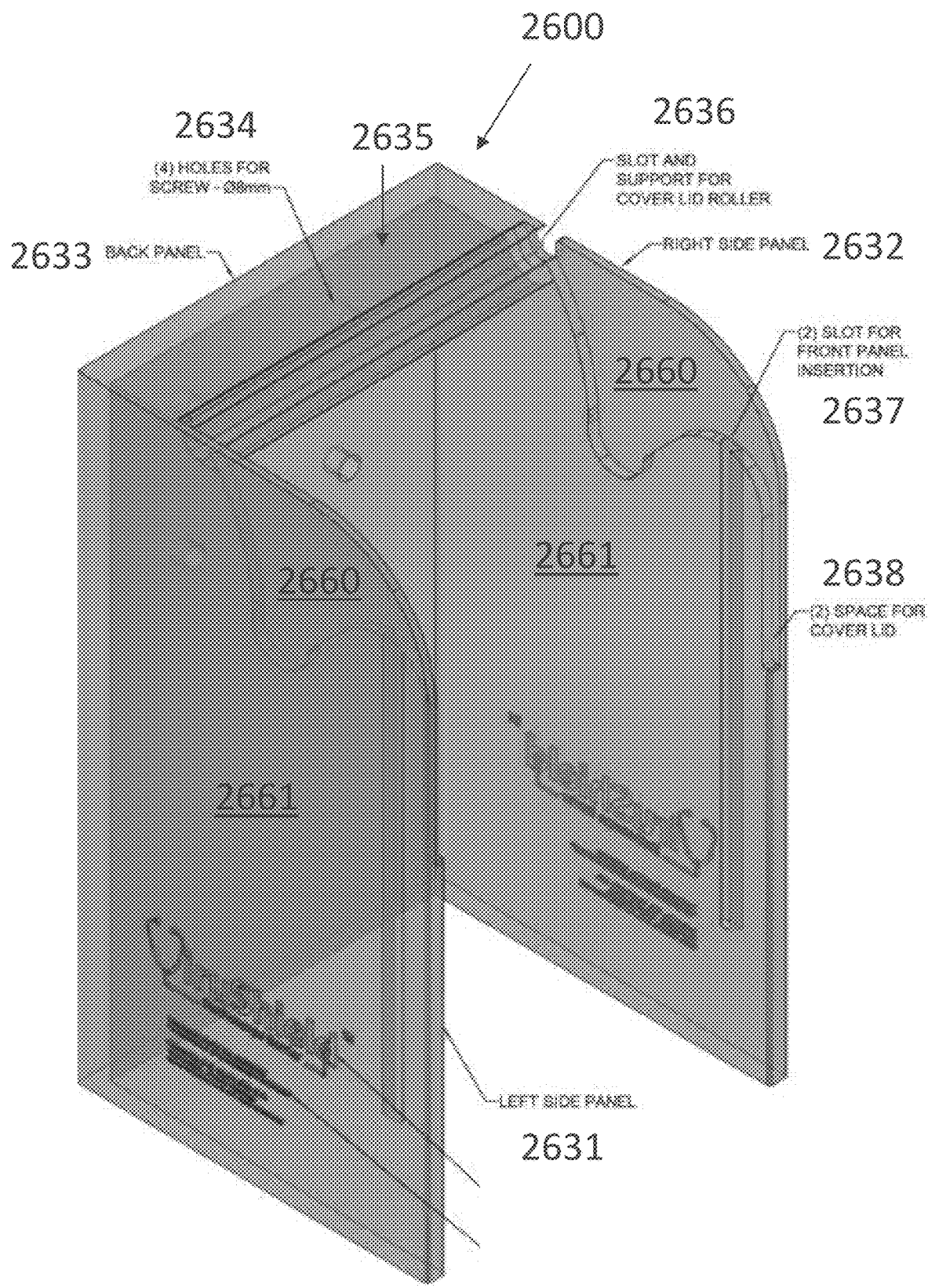
Figure 34A:
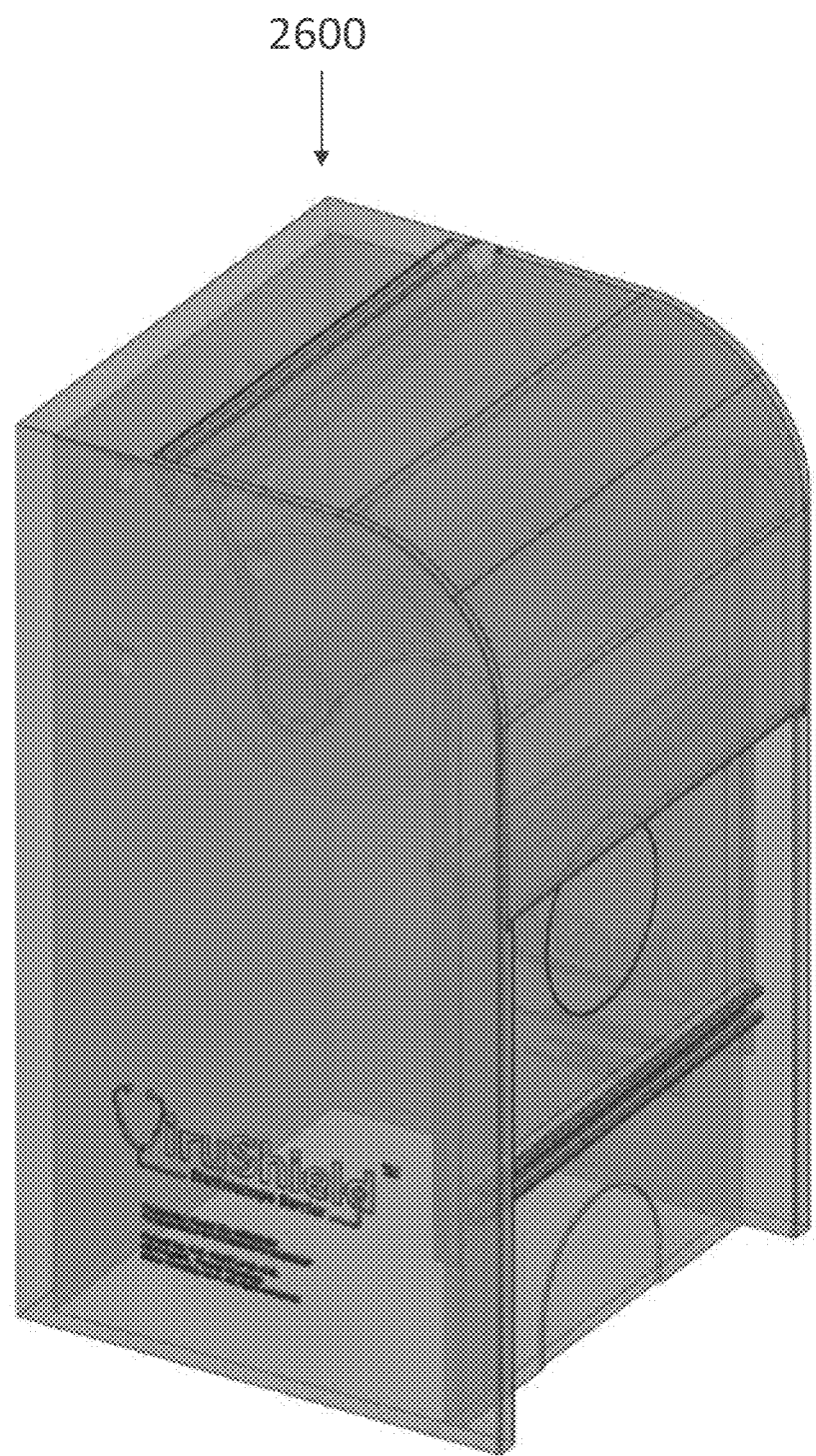
FIGS. 34A-34C schematically illustrate various views of a barrier dispenser, in accordance with an embodiment.
Figure 34B:
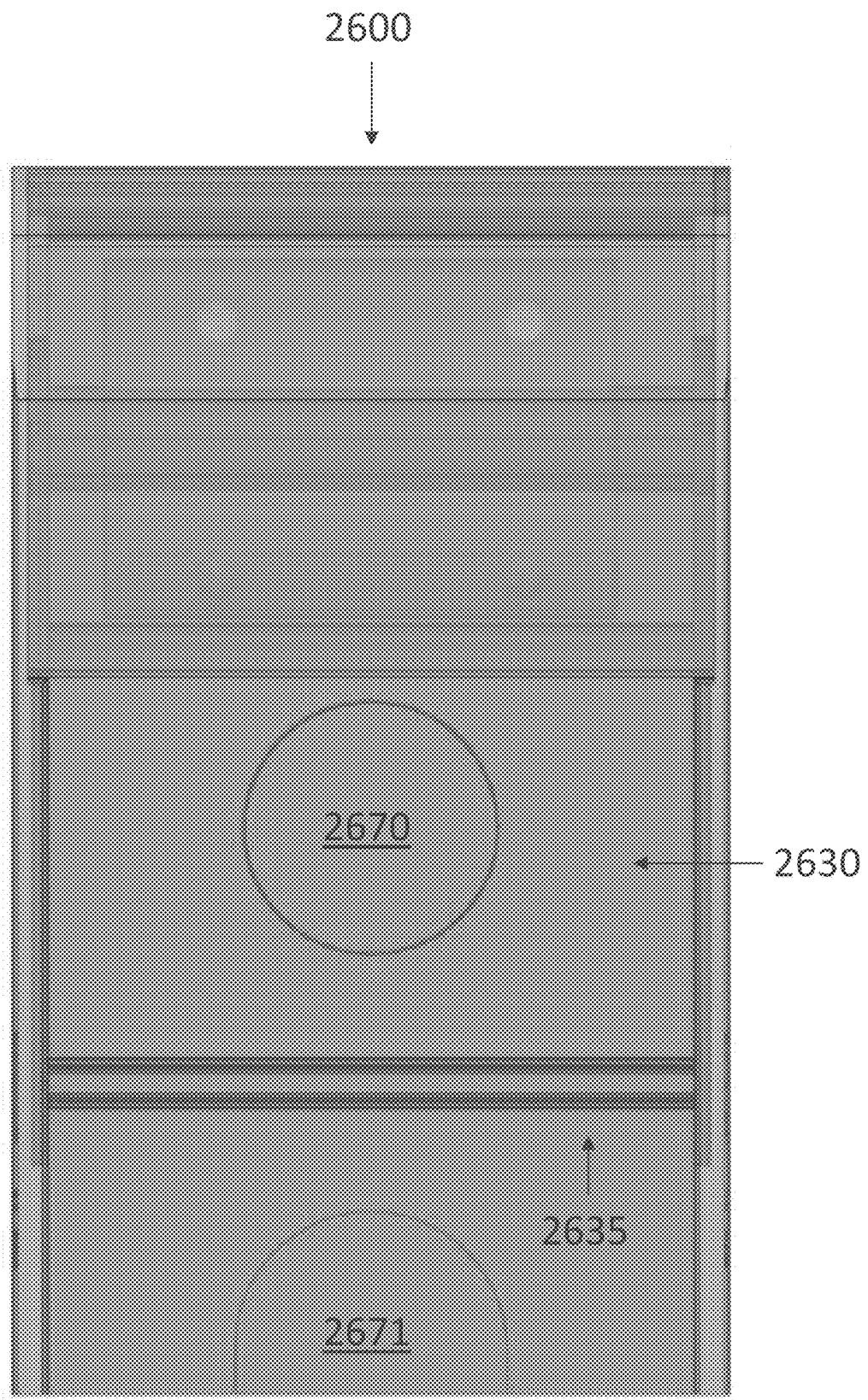
Figure 34C:
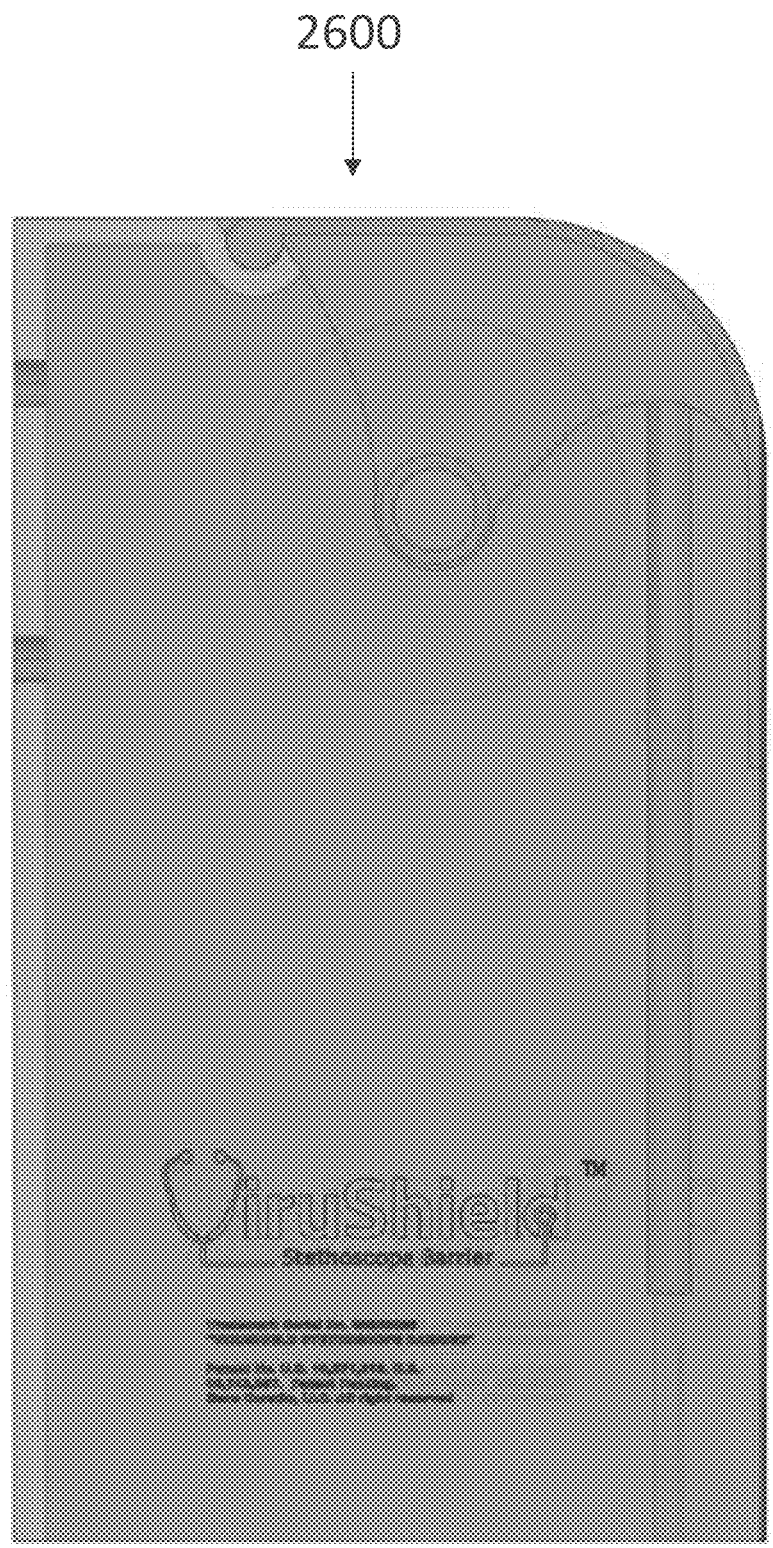

FIGS. 26A-26B, 27A-27B, 28A-28B, and 29A-29B schematically illustrate various views of a barrier dispenser 2600. FIGS. 34A-34C schematically illustrate various transparency views of a barrier dispenser 2600. As shown in FIGS. 30 and 31, the barrier dispenser 2600 may comprise a main body 2610 for housing one or more barrier materials. The barrier dispenser 2600 may further comprise a lid cover 2620 and a front panel 2630. The front panel 2630 may comprise a slider 2635 for cutting a barrier material. Alternatively, the front panel may not or need not comprise a slider for cutting a barrier material. In such cases, the dispensed material may be pre-cut, tear off roll, roll, single sheet, stacked/interleafed single sheet, or stacked like finger cots. As shown in FIGS. 29B, 32A-32B, and 33A-33B, the barrier dispenser 2600 may further comprise a roller 2650 disposed within the main body 2610 of the barrier dispenser 2600. A barrier material 2655 may be dispensed from the barrier dispenser 2600 using the roller 2650. The barrier material 2655 may be wrapped around the roller 2650.

As shown in FIGS. 30 and 31, the main body 2610 of the barrier dispenser 2600 may comprise a left-side panel 2631, a right-side panel 2632, and a back panel 2633. In some cases, the main body 2610 may comprise a single integrated structure. In other cases, the main body 2610 may comprise a plurality of separate components fastened together. In some cases, the left side panel 2631, right side panel 2632, and back panel 2633 may be formed as a single integrated structure. Alternatively, the left side panel 2631, right side panel 2632, and back panel 2633 may comprise separate components or parts that can be joined together using one or more fasteners or adhesive materials. In some case, the components of the barrier dispenser may be coupled together using various snap-fits without requiring separate fasteners or tools, which can make the barrier dispenser easier to assemble and disassemble. In some embodiments, the left-side panel 2631 and the right-side panel 2632 may comprise one or more curved edges.

In some embodiments, the main body 2610 of the barrier dispenser 2600 may comprise a rectangular shape or profile with one or more rounded corners or edges. The main body 2610 may be configured to support a source of a barrier material (e.g., a roll of film, a cassette of film, interleafed, stacked, individually wrapped films, or individual sheets of film). The main body 2610 may be configured for mounting on any surface such as, for example, a wall of a room, one or more cabinets, a medical cart, etc. In some cases, the main body 2610 may be affixed to a surface using, for example, a bracket, one or more fasteners, or an adhesive material. In some cases, the back panel 2633 of the main body 2610 may comprise one or more holes 2634, as shown in FIGS. 27B and 31. The one or more holes 2634 may be used to secure a bracket to the main body 2610, which bracket may be used to secure the main body 2610 of the barrier dispenser 2600 to any surface. In some cases, one or more fasteners may be used to secure the main body 2610 to a surface. In such cases, the one or more fasteners may be routed through the one or more holes 2634 to anchor the main body 2610 to the surface. The one or more fasteners may comprise, for example, screws or bolts. In some embodiments, a combination of fasteners and one or more brackets may be used to attach the main body 2610 of the barrier dispenser 2600 to the surface.

Figure 32A:
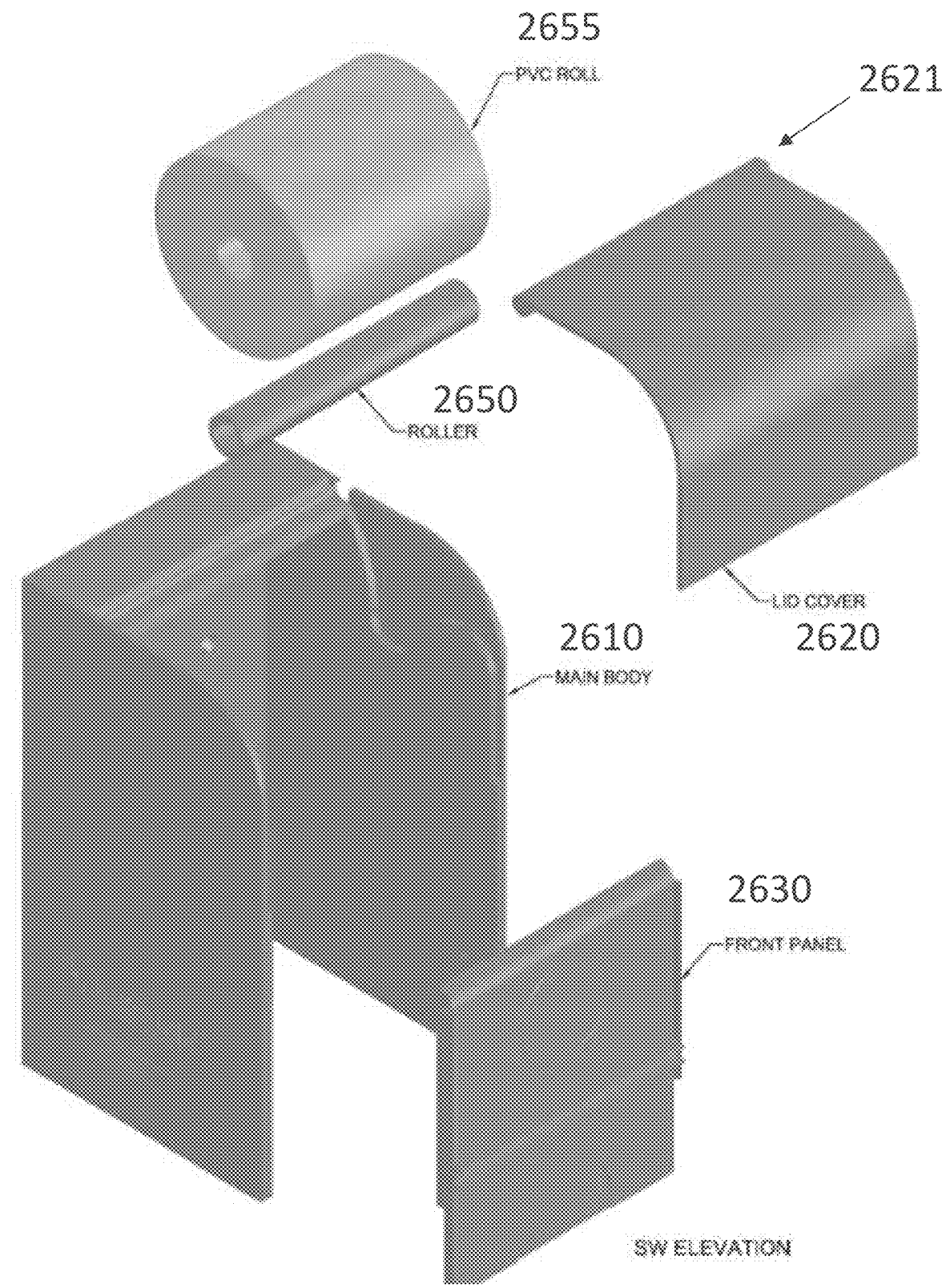
FIGS. 32A-32B schematically illustrate an exploded view of a barrier dispenser, in accordance with an embodiment.
Figure 32B:
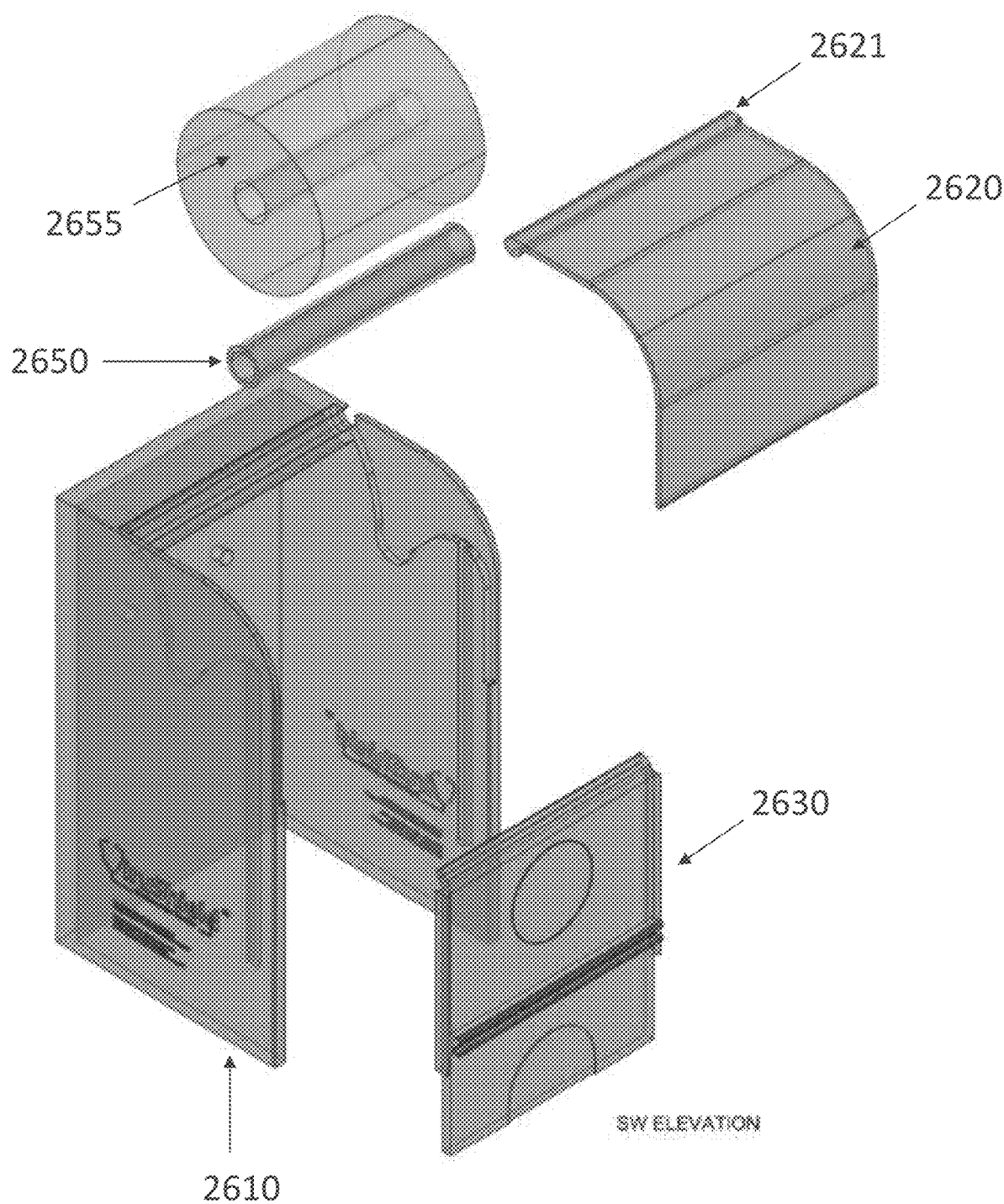
Figure 33A:
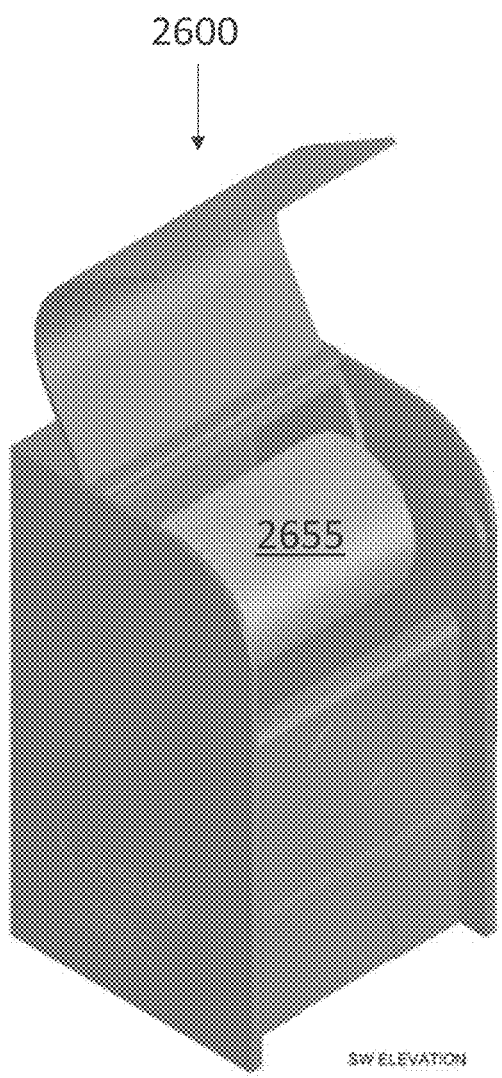
FIGS. 33A-33B schematically illustrate a barrier dispenser in an open configuration, in accordance with an embodiment.
Figure 33B:
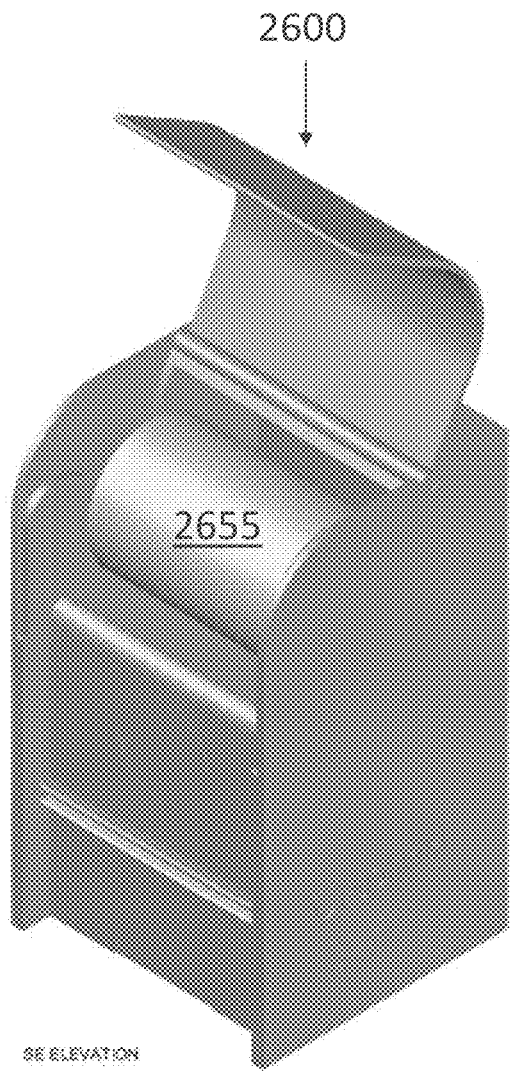

In some cases, the main body 2610 may comprise a top panel 2635 connecting the left side panel 2631 and the right-side panel 2632. The top panel 2635 may be connected to at least a portion of the left side panel 2631 and the right-side panel 2632. The top panel 2635 may be connected to an upper portion of the back panel 2633. The top panel 2635 may comprise a slot 2636 extending along a width of the top panel 2635. The slot 2636 may extend from the left side panel 2631 to the right-side panel 2632. The slot 2636 may be closed at one end such that the slot opening does not extend through, for example, the left side panel 2631. The slot 2636 may be open on another end such that the slot opening extends, for example, through the right-side panel 2632. The right-side panel 2632 may comprise an opening through which a portion of a lid cover 2620 may be inserted. The slot 2636 may be configured to support the lid cover 2620 when the lid cover 2620 is inserted into the slot 2636. The lid cover 2620 may comprise a curved panel that conforms to a shape of an upper portion of the barrier dispenser 2600. The curved panel may comprise a curvature that conforms to the curvature of the left side panel 2631 and the right-side panel 2632. As shown in FIGS. 32A-32B, the curved panel may comprise a protrusion 2621 that is sized and shaped to engage with the slot 2636 in the top panel 2635. The curved panel may be configured to at least partially enclose a top portion of the barrier dispenser when the protrusion 2621 is placed within the slot 2636 of the top panel 2635. When the protrusion 2621 of the curved panel is inserted into the slot 2636 of the top panel 2635, the lid cover 2620 may be configured to pivot relative to the slot 2636 of the top panel 2635. The lid cover 2620 may be configured to pivot or rotate along an axis corresponding to the slot 2636 of the top panel 2635. This may allow a user to open or close the barrier dispenser 2600 by moving the lid cover 2620 up or down. The protrusion 2621 on the lid cover 2620 and the slot 2636 of the top panel 2635 may comprise a similar shape or profile to allow the protrusion 2621 to engage with the slot 2636 and permit a movement of the lid cover 2620 relative to the main body 2610 of the barrier dispenser 2600. As used herein, opening the barrier dispenser 2600 may refer to moving the lid cover 2620 relative to the main body 2610 of the barrier dispenser 2600 to at least partially expose an interior region of the barrier dispenser 2600 (e.g., to access a barrier material or to exchange a roll of barrier material with another roll of barrier material). As used herein, closing the barrier dispenser 2600 may refer to moving the lid cover 2620 relative to the main body 2610 of the barrier dispenser 2600 to at least partially enclose an interior region or volume of the barrier dispenser 2600.

As shown in FIG. 31, the left side panel 2631 and the right-side panel 2632 may each comprise an interior surface facing an inner region or volume of the barrier dispenser 2600. The interior surfaces of the left side panel 2631 and the right-side panel 2632 may comprise one or more recessed regions 2660. The recessed regions 2660 may be configured to support a roll of barrier material 2655. In some cases, the roll of barrier material 2655 may be inserted in the barrier dispenser 2600 such that each side of the roll of barrier material 2655 is supported by the recessed region 2660. Once inserted into the barrier dispenser 2600, the roll of barrier material 2655 may be suspended on each side by an edge portion formed at the interface of the recessed region 2660 and other portions of the interior surfaces that are not recessed 2661. The recessed regions 2660 of the left and right-side panels may have a different thickness compared to the other non-recessed regions 2661 of the left and right-side panels. In some cases, the recessed regions 2660 may have a thickness that is at least about 5%, 10%, 15%, 20%, 25%, 30%, 35%, 40%, 45%, 50%, 55%, 60%, 65%, 70%, 75%, 80%, 85%, 90%, or 95% of a thickness of the non-recessed regions 2661. The left and right-side panels comprising the recessed regions 2660 and the non-recessed regions 2661 may be fabricated using various different processes, including, for example, injection molding, machining, and/or 3D printing.

In some cases, the interface between the recessed regions 2660 and the non-recessed regions 2661 may comprise an edge portion which may support a barrier material or a roll of a barrier material. The edge portion may comprise an indentation or a protrusion that is sized and shaped to receive a roller comprising a barrier material wrapped around the roller. The indentation or protrusion may be configured to secure the roller in place. In some cases, the roller may comprise a counterpart mating feature (e.g., another complementary indentation or protrusion) that allows the roller to lock into place when the roller is placed in or near the edge portion of the interface between the recessed regions 2660 and the non-recessed regions 2661. In some cases, the roller may comprise one or more flattened surfaces or depressions that allow the roller to lock into place. In any case, the roller may still rotate freely relative to the barrier dispenser. In some cases, the roller may be restricted from undergoing a translational motion relative to the barrier dispenser. In some cases, the roller may be secured to the left side panel and/or the right-side panel (e.g., using one or more fasteners). In other cases, the roller may be configured to hang and rotate freely without the use of external fasteners. In some cases, the roller may be secured in place and stationary, while the barrier material is being extended or unraveled by a user. In other cases, the roller and the barrier material may both rotate at the same time as the barrier material is being extended or unraveled by a user of the barrier dispenser.

In some cases, the recessed regions 2660 on the interior surfaces of the left side panel 2631 and the right-side panel 2632 may provide a spacing 2638 for the lid cover 2620 to rest when the lid cover 2620 is closed. The spacing 2638 may be provided near a front edge of the left side panel 2631 and the right-side panel 2632. The spacing 2638 may permit the lid cover 2620 to lie flush with the front edges of the left side panel 2631 and the right-side panel 2632 when the lid cover 2620 is placed in a closed position.

In some embodiments, the left side panel 2631 and the right-side panel 2632 may each comprise a slot 2637. The slot 2637 may be a vertical slot. The slots 2637 on each of the left side panel 2631 and the right-side panel 2632 may be sized and shaped to permit insertion of a front panel 2630 into the slots 2637. The front panel 2630 may be used to enclose at least a portion of the main body 2610 of the barrier dispenser 2600. The front panel 2630 may be configured to slide in and out of the slots 2637 on the left side panel 2631 and the right-side panel 2632. The front panel 2630 may be removed if needed in order to access an interior region or volume of the barrier dispenser 2600. Alternatively, the front panel 2630 may be left in place, and the lid cover 2620 may be moved to enable access to an interior region or volume of the barrier dispenser 2600.

In some cases, the recessed regions 2660 on each of the left side panel 2631 and the right-side panel 2632 may comprise one or more recessed regions 2660 configured to support a first end of a roll of barrier material 2655 and/or a second end of the roll of barrier material 2655. The roll of barrier material 2655 may comprise a barrier material that is provided around a roller 2650. In some cases, the one or more recessed regions 2660 configured to support a first end of the roller 2650 and/or a second end of the roller 2650. The one or more recessed regions 2660 may permit the roller 2650 and/or the barrier material 2655 to rotate relative to the barrier dispenser 2600 to dispense a barrier material 2655 (e.g., by allowing the barrier material 2655 to unroll and extend in response to an external force or a pulling motion provided by a user of the barrier dispenser 2600).

Figure 27A:
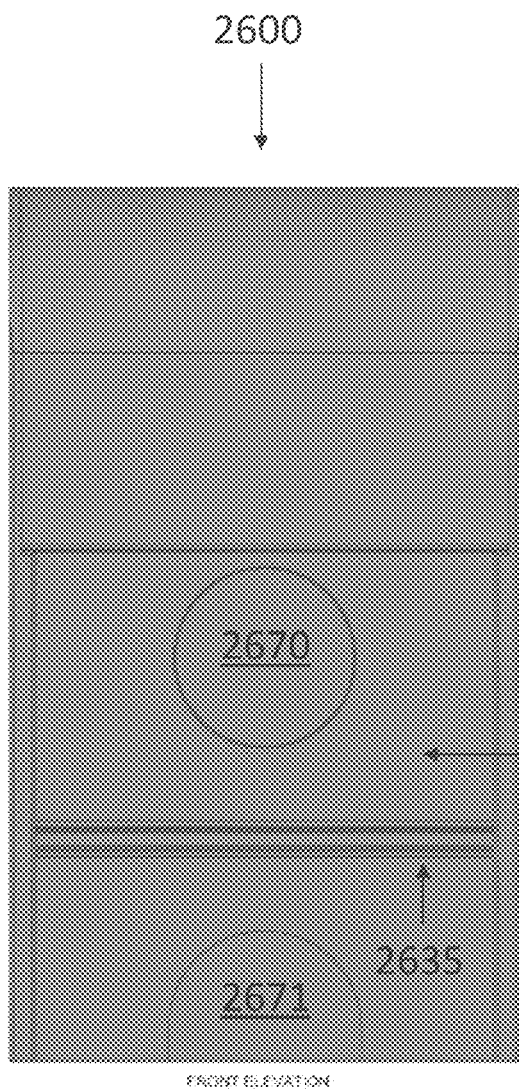
Figure 27B:
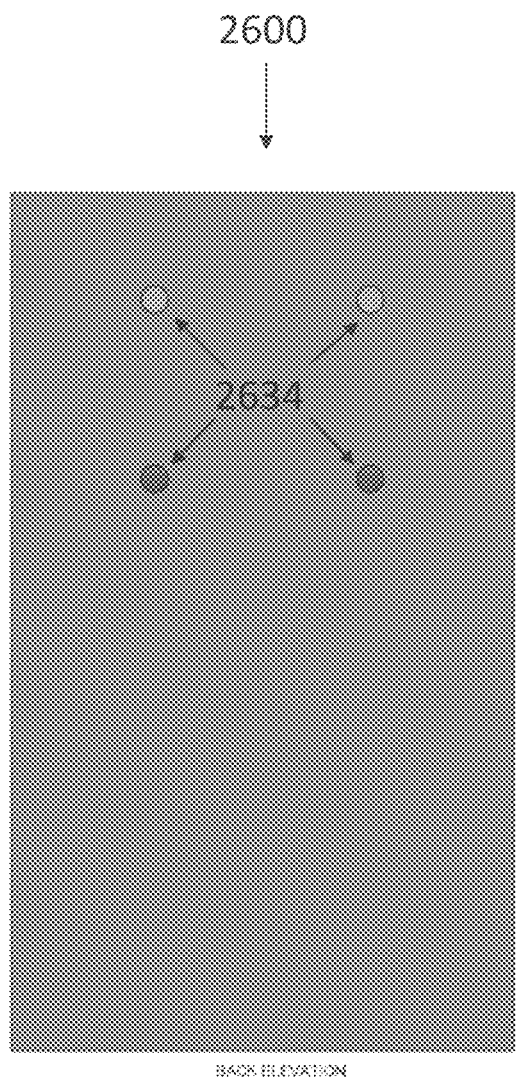
Figure 29A:
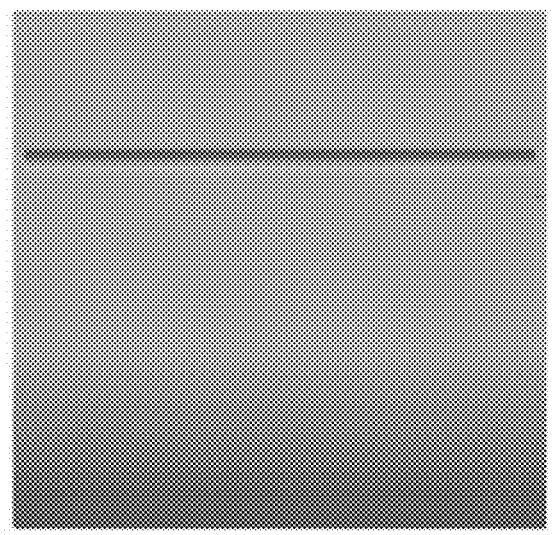
Figure 29B:
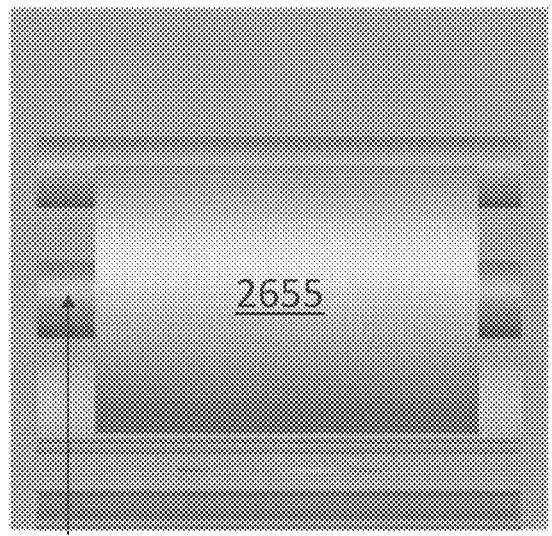

As shown in FIGS. 27A and 34B, the front panel 2630 may comprise a first recessed region 2670 and a second recessed region 2671. The first recessed region 2670 may be located above the slider or cutter 2635. The second recessed region 2671 may be located below the slider or cutter 2635. An object (e.g., a scope) may be placed in or near the first recessed region 2670. The object may be at least partially wrapped with a barrier material 2655. Afterwards, the barrier material 2655 and the object that is at least partially wrapped with the barrier material 2655 may be pulled downwards past the slider or cutter 2635. In some cases, the object that is at least partially wrapped with the barrier material 2655 may be repositioned in or near the second recessed region 2671. Afterwards, the barrier material 2655 may be cut using the slider or cutter 2635, and the remaining portions of the object may be wrapped using the cut barrier material 2655.

Figure 35:
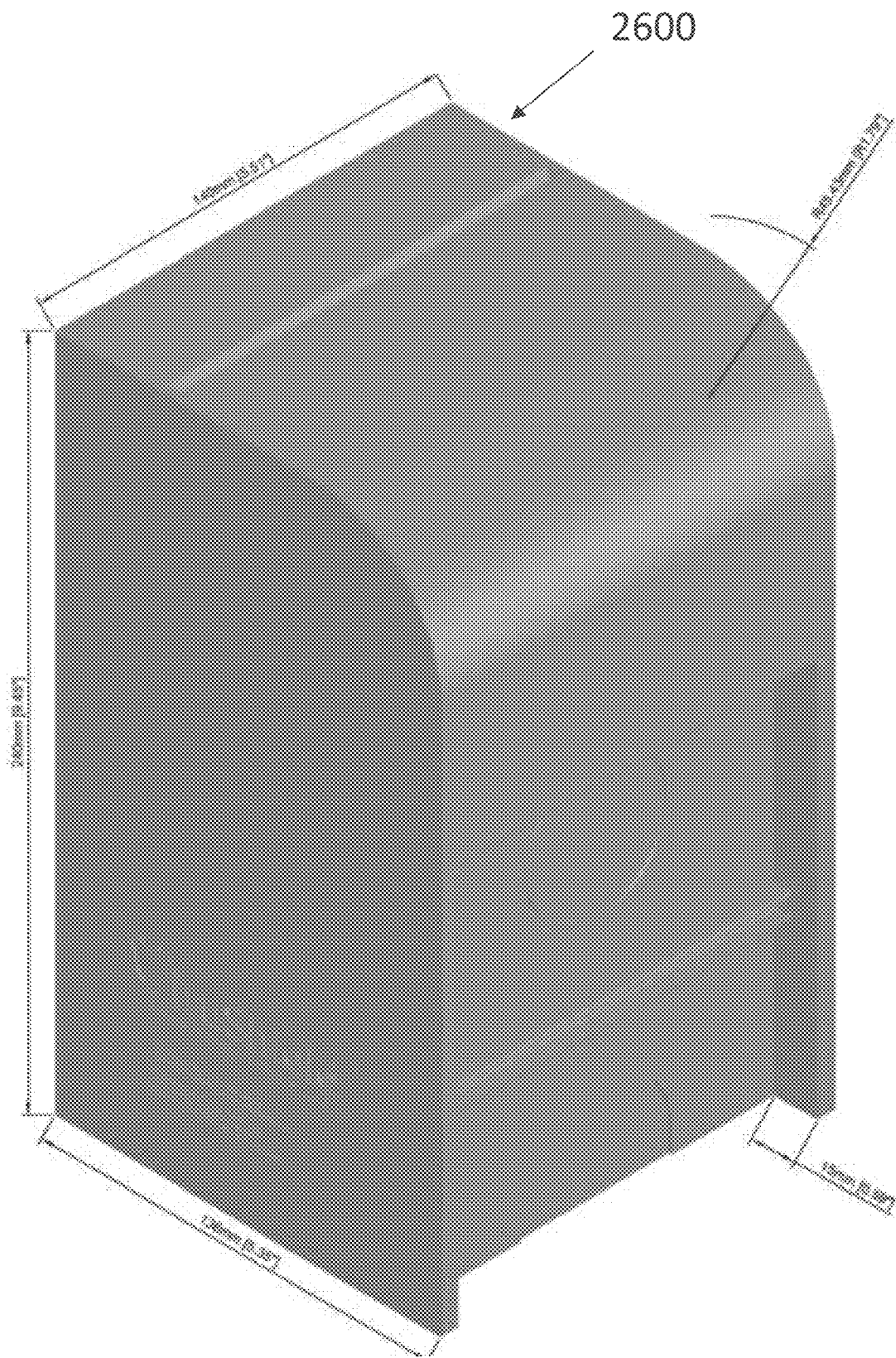
FIG. 35 schematically illustrates exemplary dimensions for a barrier dispenser, in accordance with an embodiment.

FIG. 35 schematically illustrates various exemplary dimensions for a barrier dispenser 2600 as disclosed elsewhere herein. In some cases, the barrier dispenser 2600 may have a depth of about 136 millimeters or about 5.35 inches. In some cases, the barrier dispenser 2600 may have a height of about 240 millimeters or about 9.45 inches. In some cases, the barrier dispenser 2600 may have a width of about 140 millimeters or about 5.5 inches. In some embodiments, the barrier dispenser 2600 may have a depth ranging from about 100 millimeters to about 150 millimeters. In some embodiments, the barrier dispenser 2600 may have a height ranging from about 200 millimeters to about 300 millimeters. In some embodiments, the barrier dispenser 2600 may have a width ranging from about 100 millimeters to about 200 millimeters.

Figure 36:
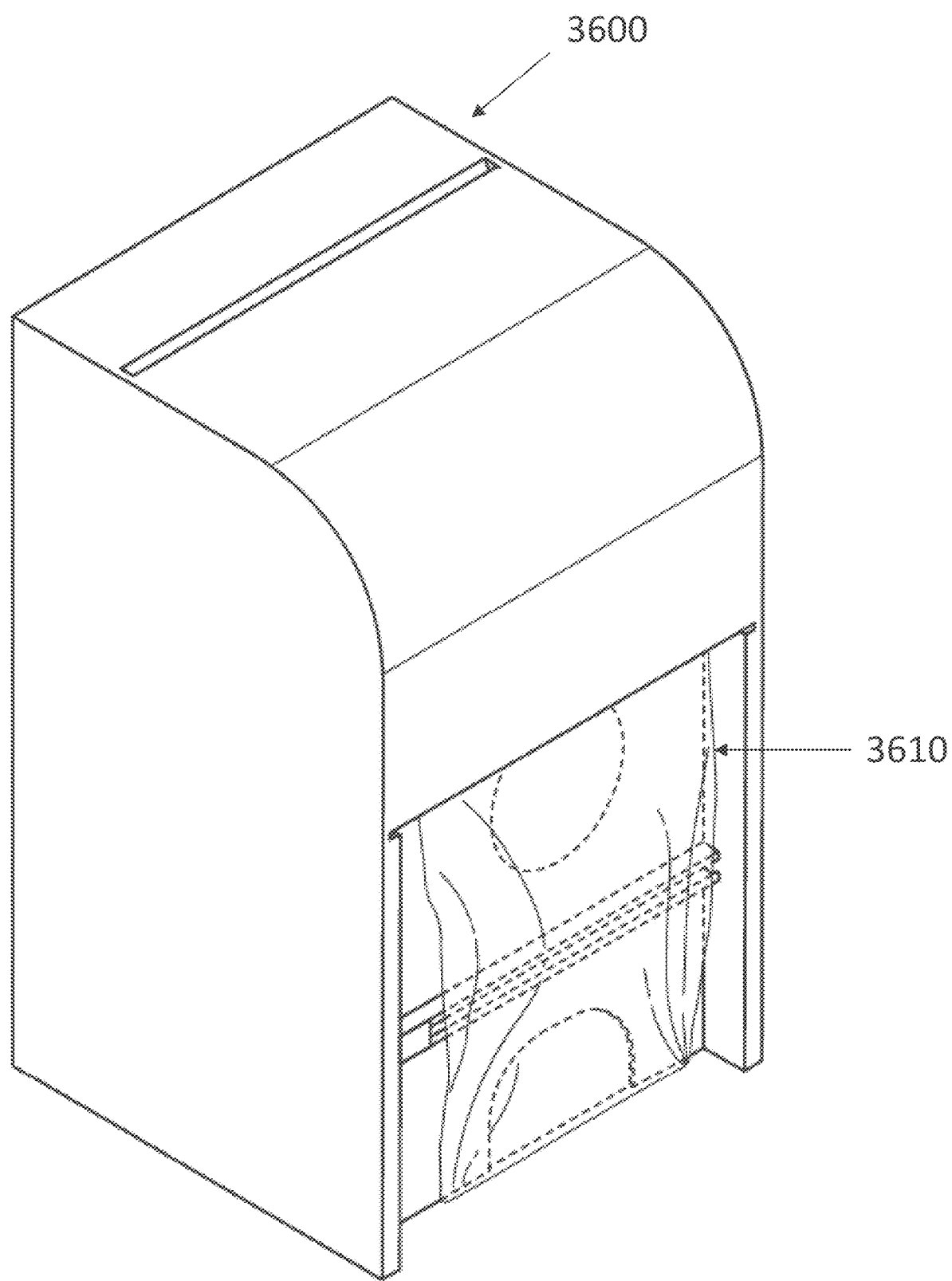
FIGS. 36-44 schematically illustrate an exemplary method for using a barrier dispenser, in accordance with an embodiment.

FIGS. 36-44 schematically illustrate an exemplary method for using a barrier dispenser, in accordance with various embodiments of the present disclosure. Referring to FIG. 36, a barrier dispenser 3600 may be used to hold a barrier material 3610 within an inner volume of the barrier dispenser 3600. The barrier material 3610 may be extended from the inner volume of the barrier dispenser 3600 and may hang in front of a front panel of the barrier dispenser 3600 to enable quick and convenient access by a user.

Figure 37:
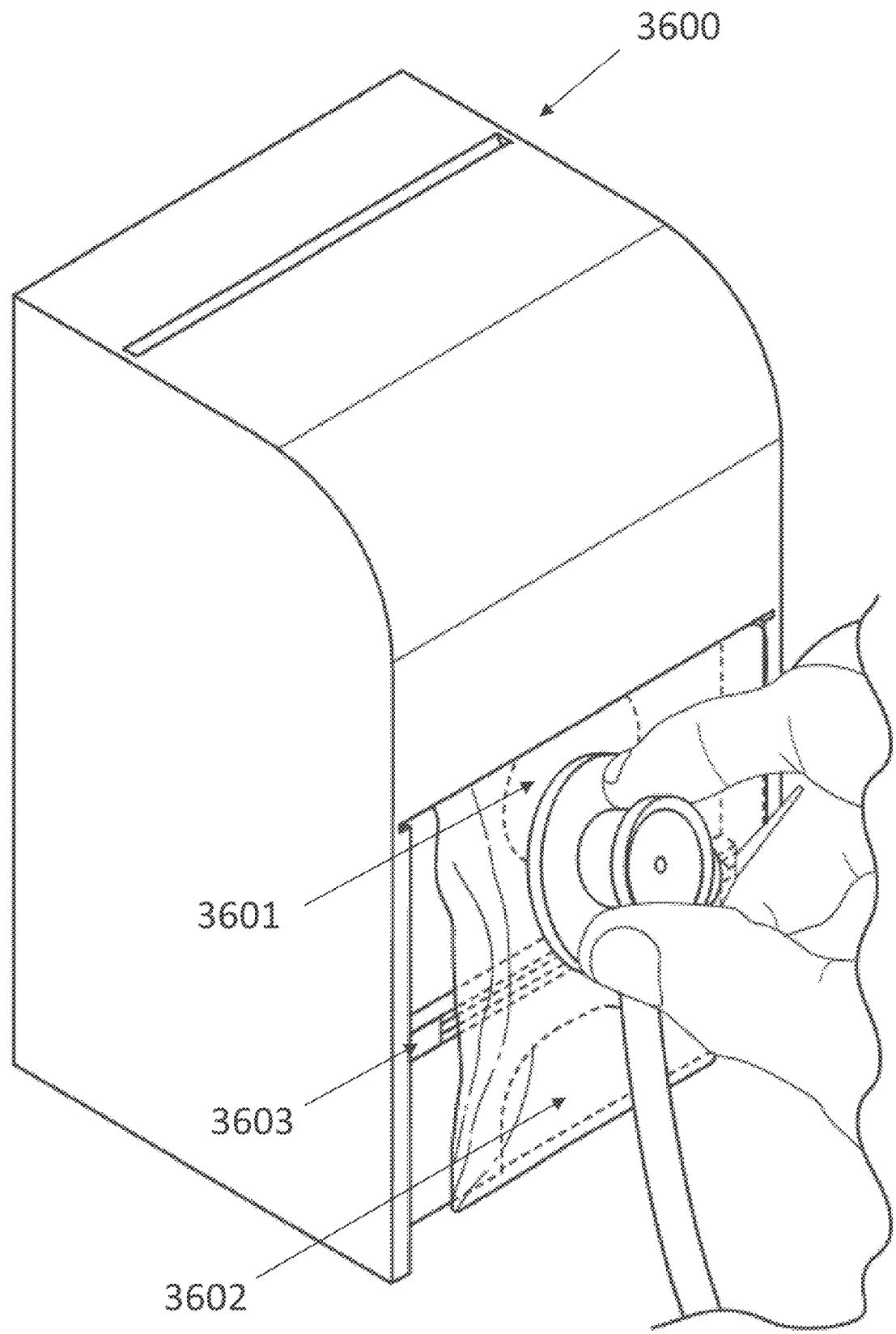

Referring to FIG. 37, a user may move an instrument towards a first region 3601 on the front panel of the barrier dispenser 3600. The first region may be located above a cutter 3603 that can be used to cut the barrier material 3610. In some cases, the front panel of the barrier dispenser 3600 may comprise a second region 3602 located below the cutter 3603. The first region 3601 and the second region 3602 may be used to receive and/or secure the instrument to enable the user to wrap the instrument (or a portion thereof) with the barrier material 3610. In some cases, the first 3601 region and/or the second region 3602 may comprise a recessed region in which an instrument (or a portion thereof) may be placed or secured during a wrapping operation.

Figure 38:
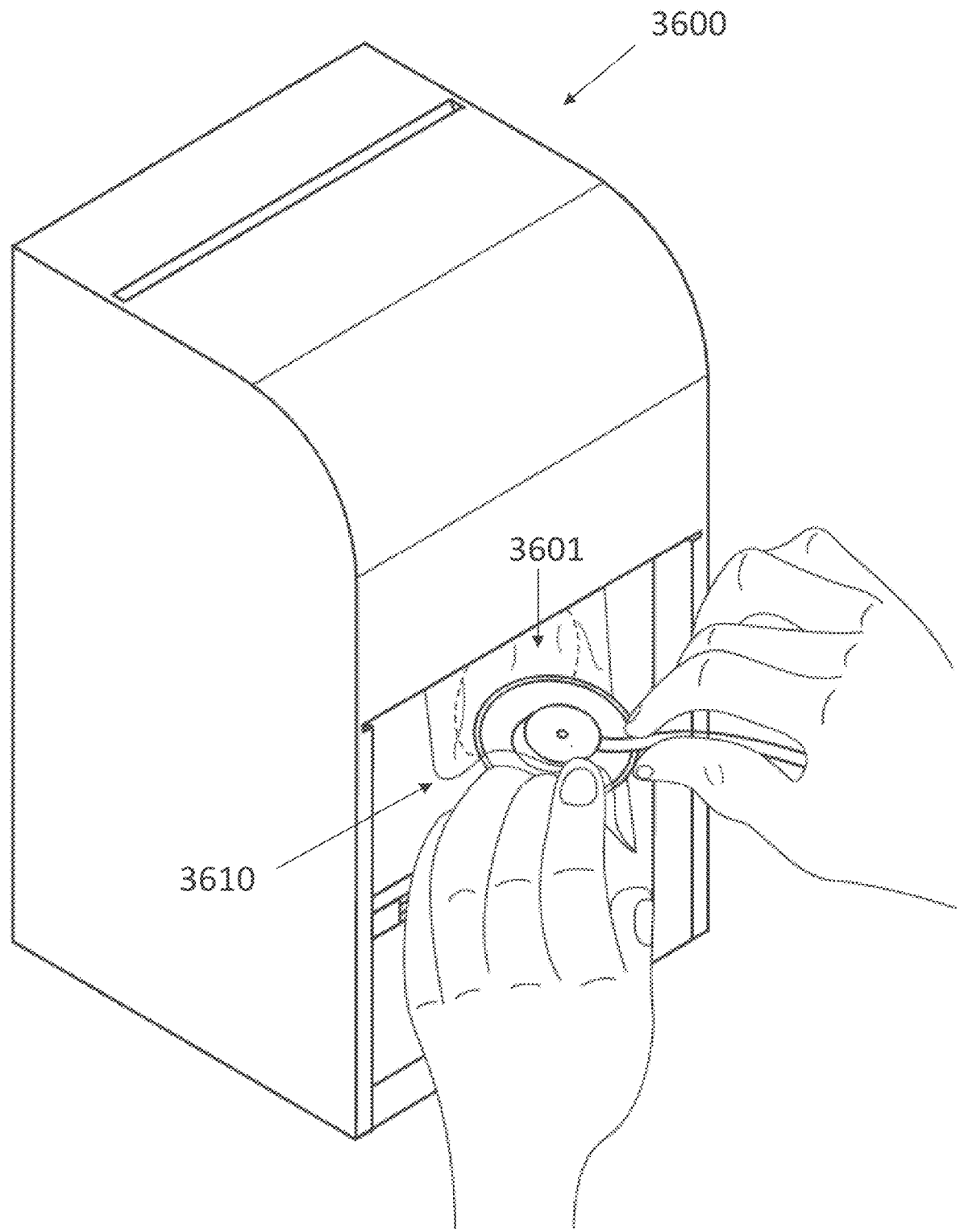
Figure 39:
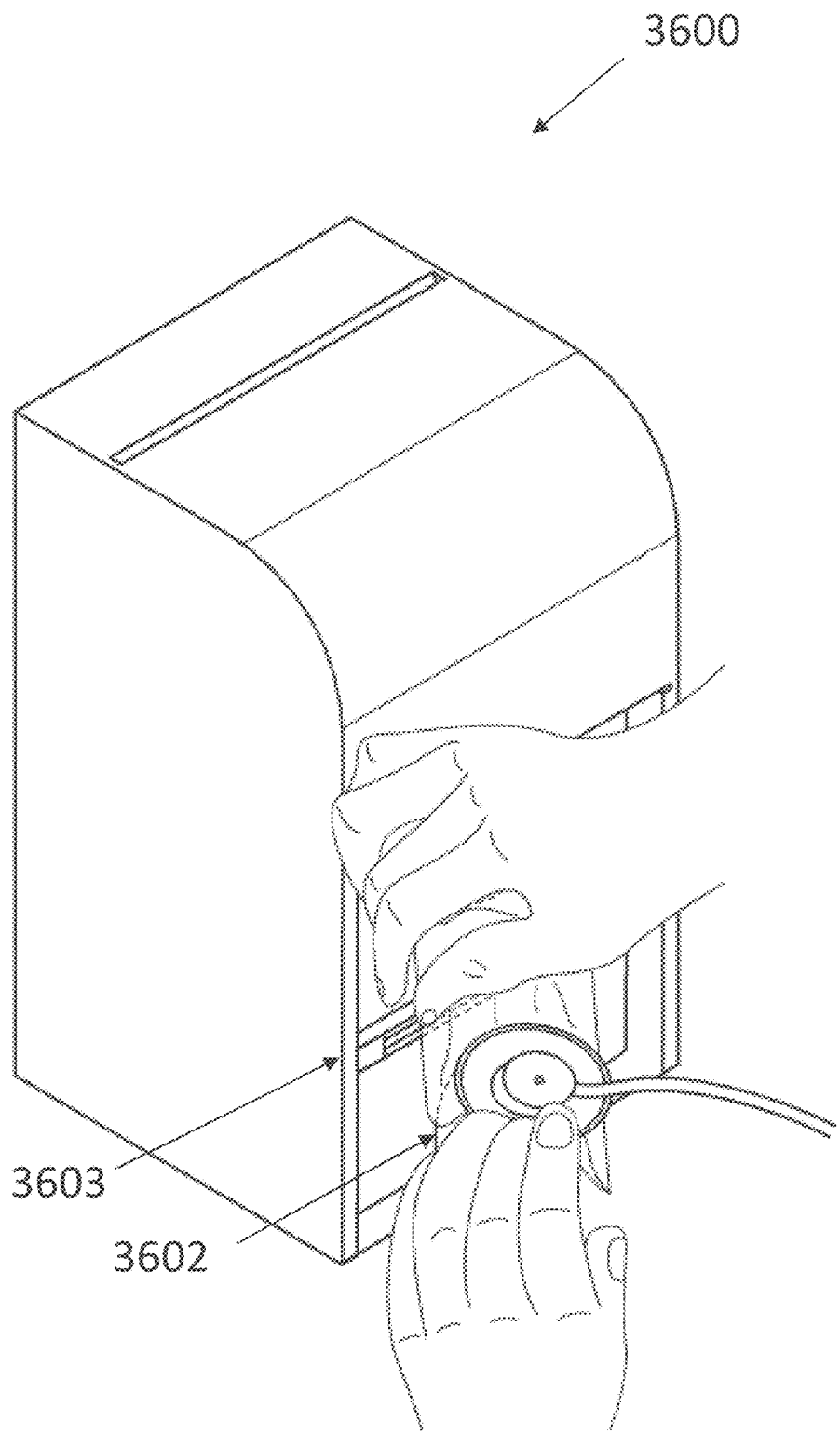
Figure 40:
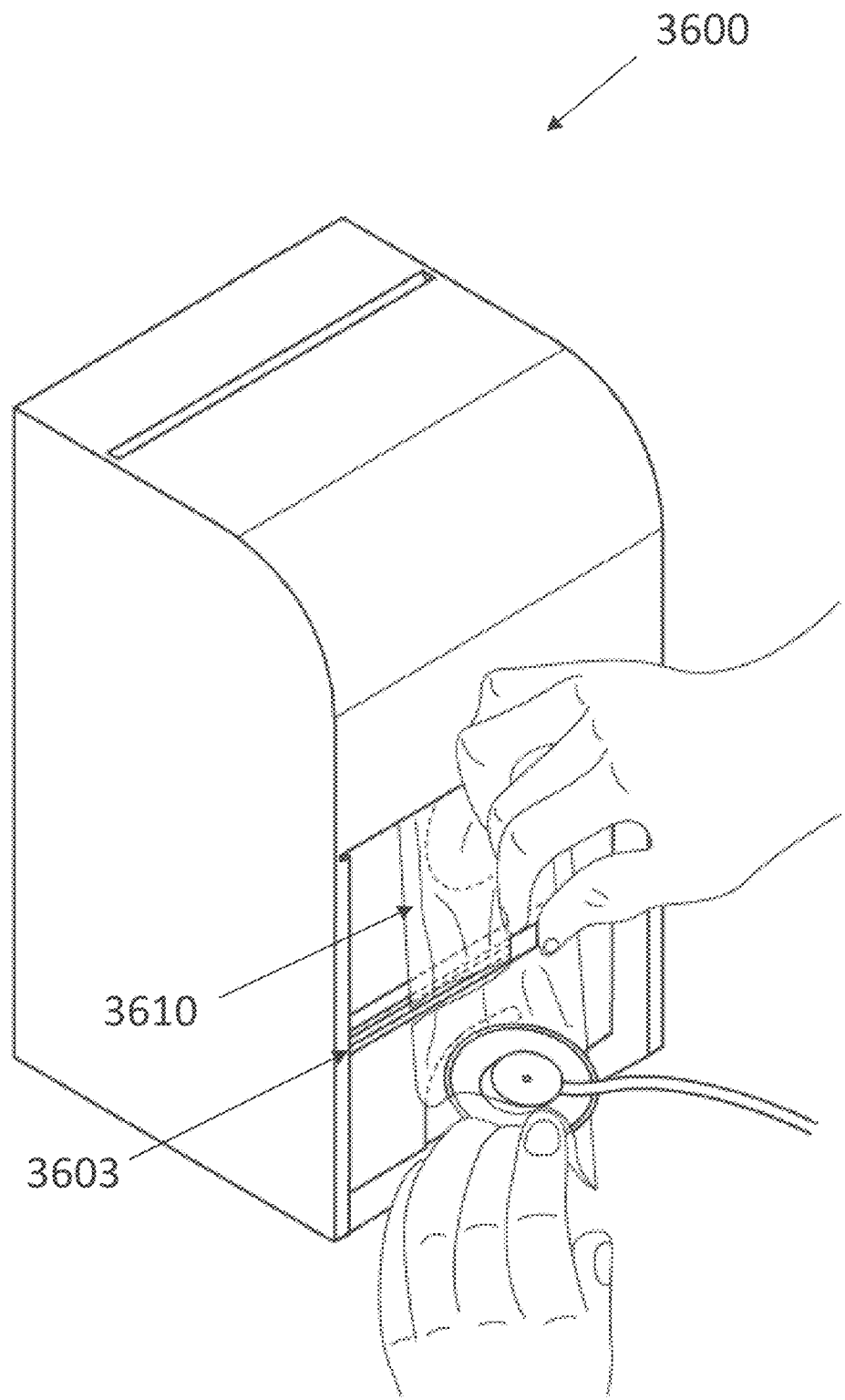
Figure 41:
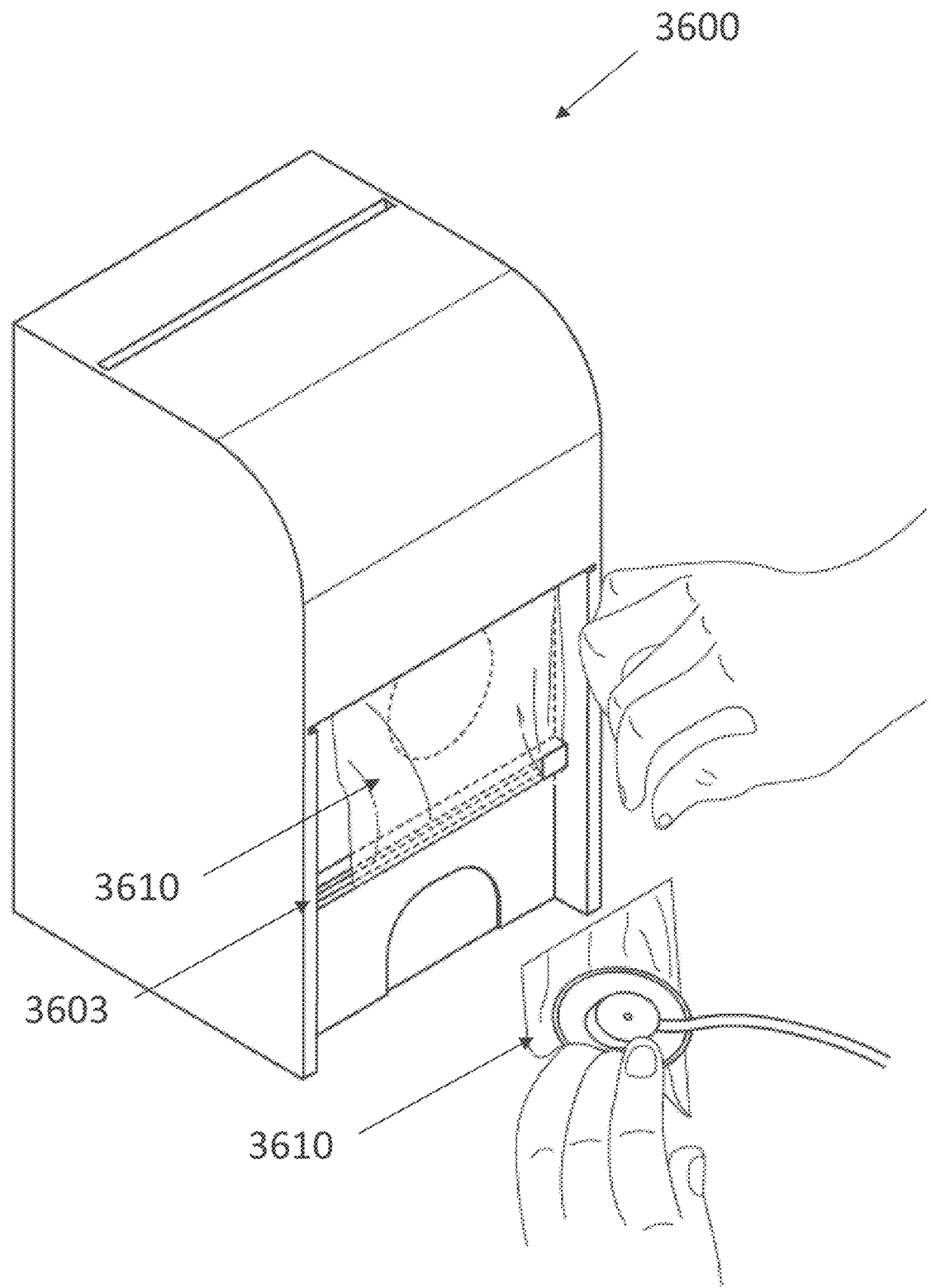
Figure 42:
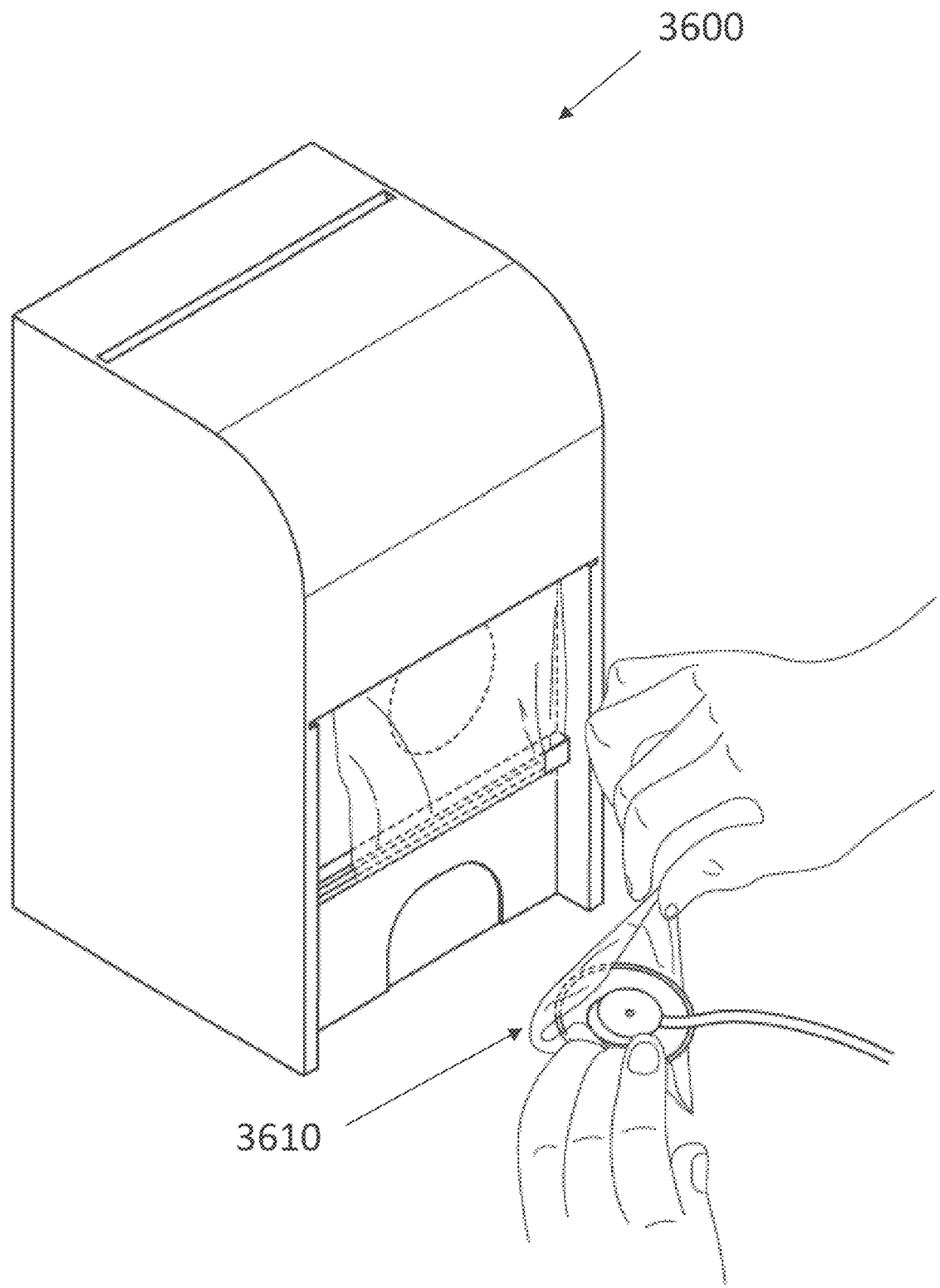
Figure 43:
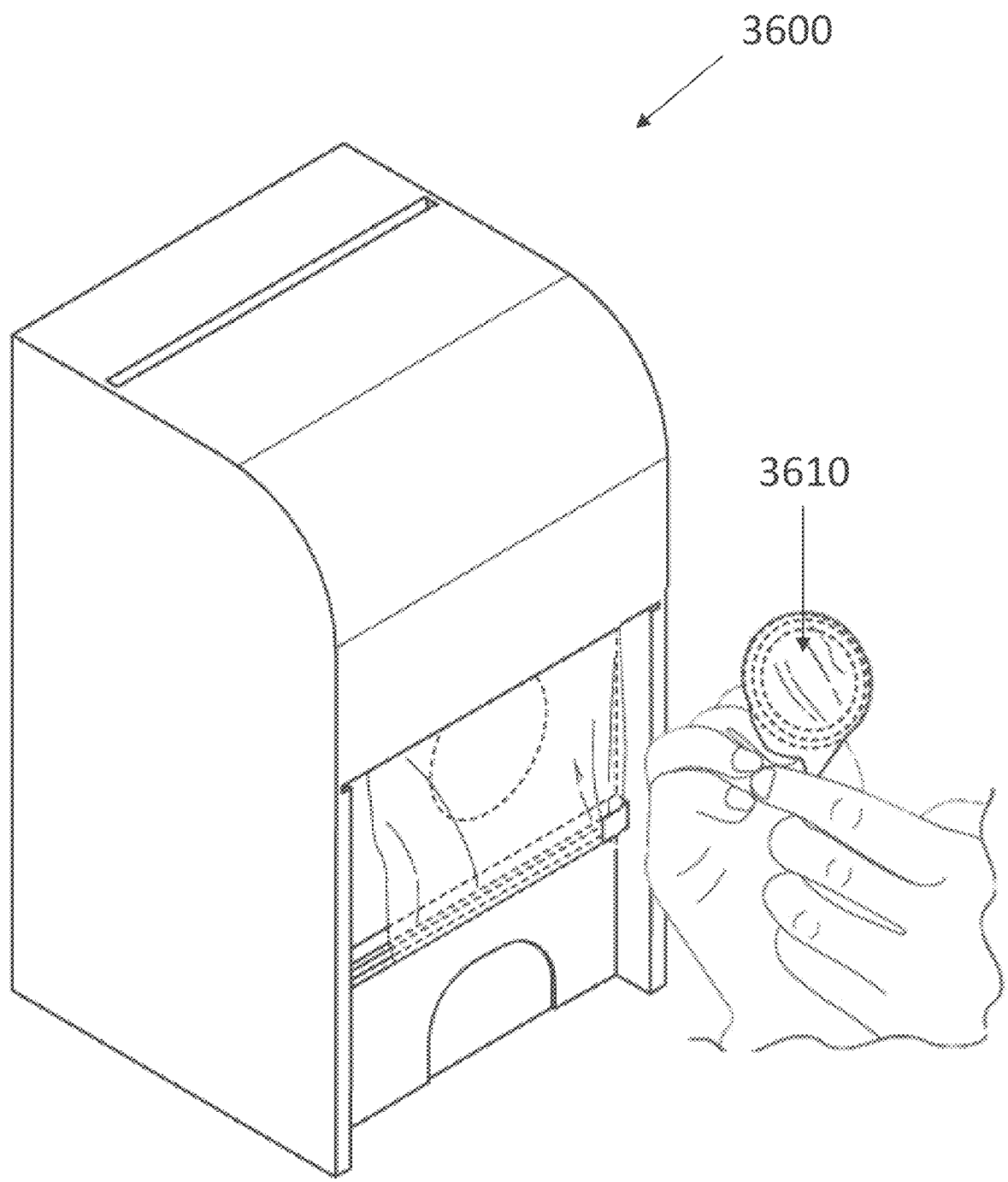
Figure 44:
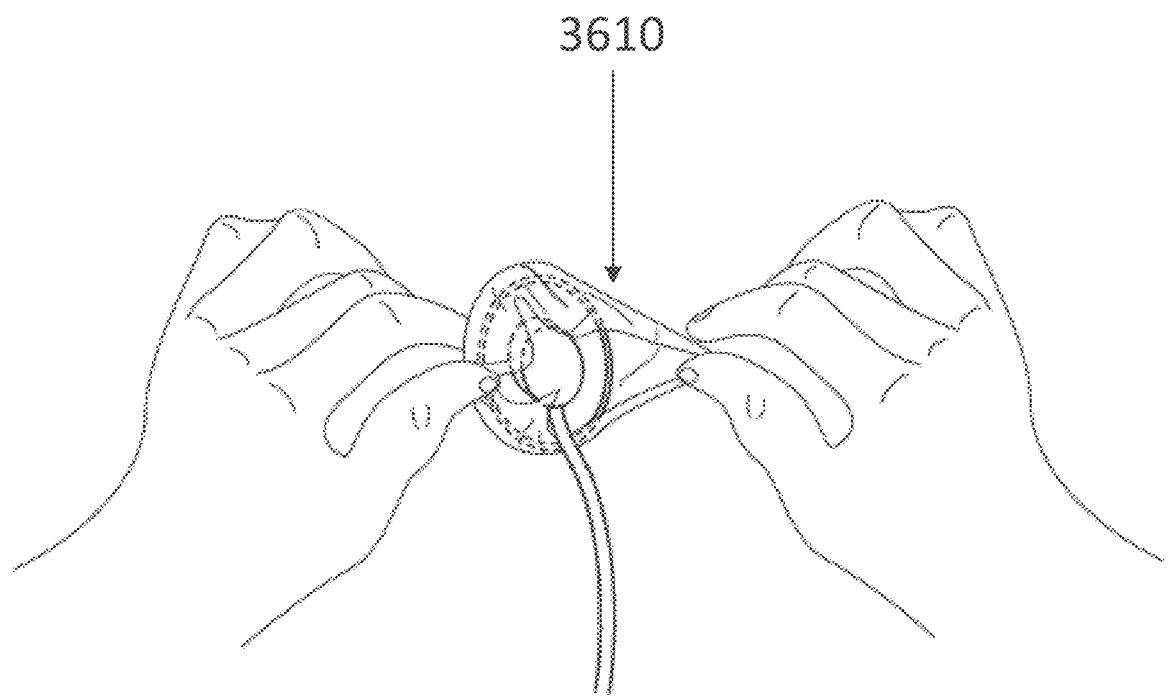

Referring to FIG. 38, a user may place at least a portion of an instrument within the first region 3601 on the front panel of the barrier dispenser 3600 and partially wrap a bottom portion of the instrument with the barrier material 3610. As shown in FIG. 39, the user may then move the partially wrapped instrument downwards below the cutter 3603 and simultaneously pull on the barrier material 3610 such that the barrier material 3610 also extends below the cutter 3603. In some cases, the instrument may be placed in the second region 3602 below the cutter 3603 to secure or hold the instrument in place while the user operates the cutter 3603 to cut the barrier material 3610. As seen in FIG. 40, the user may then operate the cutter 3603 (e.g., by sliding a movable portion of the cutter 3603 relative to the barrier dispenser 3600) to cut the barrier material 3610. FIG. 41 shows the barrier material 3610 after the user cuts the barrier material 3610 using the cutter 3603. As shown in FIG. 42, after the user cuts the barrier material 3610, the user may use the barrier material 3610 to wrap the remaining portions of the instrument that have not been completely wrapped. FIG. 43 shows an example of an instrument completely wrapped by the barrier material 3610. After the instrument has been used, the barrier material 3610 may be unwrapped from the instrument and dispensed. The barrier dispensers of the present disclosure may enable users to apply a barrier material to a tool or an instrument in less time than other conventional systems would allow. For example, the series of steps shown in FIGS. 36-44 for wrapping a tool or instrument with the barrier material using the presently disclosed barrier dispensers may take at most about 10 seconds, 9 seconds, 8 seconds, 7 seconds, 6 seconds, 5 seconds, 4 seconds, 3 seconds, or less.

In some cases, the barrier dispenser may not or need not comprise a latching mechanism to secure the lid cover to a portion of the main body of the dispenser. In other cases, the barrier dispenser may comprise a latching mechanism that is configured to secure the lid cover to a portion of the main body of the barrier dispenser (e.g., when the lid cover is in a closed position). The latching mechanism may comprise, for example, a snap fit or a press fit. The snap fit or press fit may allow a user to secure the lid cover to the main body of the barrier dispenser by applying a force to the lid cover such that a structural portion of the lid cover engages with the snap fit or press fit to restrict a movement of the lid cover relative to the main body of the barrier dispenser. In some cases, the latching mechanism may comprise a magnetic interface to hold the lid cover in a closed position. In other cases, the latching mechanism may comprise a spring-loaded mechanism, a magnet, a gravity fed mechanism, or may utilize another form of stored energy. When a user moves the lid cover towards a closed position, the movement of the lid cover may cause a portion of the lid cover to engage with the spring-loaded mechanism, and the spring-loaded mechanism may provide a spring force feedback to the user. If the user continues to apply a force to close the lid cover that overcomes the spring force feedback, the lid cover may engage with a locking mechanism (which may be indicated by an audible noise such as a click), thereby securing the lid cover in a closed position and restricting the movement of the lid cover. When the lid cover is in the closed position, the user may apply another force (e.g., by pressing the lid cover downwards again to overcome the spring force feedback) to release the locking mechanism so that the lid cover may be opened again.

In some cases, the lid cover may be opened and/or closed manually by a user. In other cases, the lid cover may be opened and/or closed automatically based on an initial physical input provided by the user. The initial physical input may comprise, for example, a press of a button or a movement of a lever. In such cases, the barrier dispenser may comprise a button or a lever that may be physically manipulated to cause the lid cover to move between an open position and a closed position and/or engage with or disengage from a locking mechanism.

As described elsewhere herein, the front panel of the barrier dispenser may comprise a first recessed region that is positioned above a cutter. The barrier dispenser may also comprise a second recessed region that is positioned below the cutter. A user may place a surgical tool or instrument (e.g., a stethoscope) within the first recessed region and/or the second recessed region to facilitate wrapping of at least a portion of the surgical tool or instrument with the barrier material. The first recessed region may comprise, for example, a circular shape. In some cases, the first recessed region may comprise a polygonal shape having three or more sides. In some cases, the first recessed region may comprise a regular or irregular shape comprising one or more linear or non-linear (i.e., curved) sides. The second recessed region may comprise, for example, a circular or semi-circular shape. In some cases, the second recessed region may comprise a polygonal shape having three or more sides. In some cases, the second recessed region may comprise a regular or irregular shape comprising one or more linear or non-linear (i.e., curved) sides. In some embodiments, the first recessed region and the second recessed region may be a same size and/or a same shape. Alternatively, the first recessed region and the second recessed region may have different sizes and/or different shapes. The first recessed region and/or the second recessed region may have a surface area of at least about 0.0001 $m^2$, 0.001 $m^2$, 0.01 $m^2$, 0.1 $m^2$, or more. The first recessed region and/or the second recessed region may have a surface area of at most about 0.1 $m^2$, 0.01 $m^2$, 0.001 $m^2$, 0.0001 $m^2$, or less.

In some embodiments, the first recessed region and/or the second recessed region may be illuminated to aid a user in placing a portion of a tool or instrument within the first recessed region and/or the second recessed region. The first recessed region and/or the second recessed region may be illuminated when the tool or instrument is positioned near the first recessed region and/or the second recessed region. In some embodiments, the first recessed region and/or the second recessed region may comprise a touch-sensitive sensor configured to detect a presence or a proximity of the tool or instrument. The sensor may be operatively coupled to a controller that is configured to control a light source used to provide illumination for the first recessed region and/or the second recessed region, based on one or more sensor readings or measurements obtained using the sensor. The illumination of the first recessed region and/or the second recessed region may aid a user in placing a tool or instrument in the first recessed region and/or the second recessed region when the user is operating in a dark environment.

In some embodiments, the first recessed region and/or the second recessed region may comprise markings or instructional graphics indicating a suggested series of steps for using the barrier dispenser. The markings or instructional graphics may comprise, for example, numbers and/or arrows showing a user a first region to initially place the tool or instrument, a direction to pull the barrier material after wrapping a portion of the tool or instrument, a second region to place the tool or instrument after pulling the barrier material and the tool or instrument downwards below the cutter, and a direction to move the cutter to cut the barrier material. Such markings and instructional graphics may enhance the workflow for using the barrier dispenser and can provide guidance to a user without the use of separate instructional manuals or videos.

In some embodiments, the barrier dispenser may comprise one or more features or components to monitor an amount of barrier material remaining. This can help a user to determine when a barrier material may need to be replaced. In some cases, the barrier dispenser may comprise one or more optical sensors configured to detect a thickness of the remaining barrier material that is still wrapped around a roller. In some cases, the barrier dispenser may comprise one or more weight sensors for determining an amount of remaining barrier material based on a change in weight of the barrier dispenser or the roll of barrier material over time. In some cases, the barrier dispenser may comprise one or more encoder sensors configured to count a number of times the barrier dispenser has been used or a number of rotations of the roll of barrier material. When the barrier dispenser has less than a predetermined amount of barrier material remaining, the barrier dispenser may provide a signal to a user to replace the barrier material. The signal my comprise, for example, an optical signal (e.g., a light indicator), an audible signal (e.g., a beep), or a haptic signal (e.g., a vibration).

In some embodiments, the barrier dispenser may comprise one or more optically transparent portions or components to allow a user to visually determine an amount of barrier material remaining within the barrier dispenser. The one or more optically transparent portions or components may comprise, for example, a transparent window. The transparent window may constitute a portion of the front panel, a left side panel, a right-side panel, a back panel, or a lid cover of the barrier dispenser.

The barrier dispenser configurations shown in FIGS. 26A-26B, 27A-27B, 28A-28B, 29A-29B, 30, 31, 32A-32B, 33A-33B, 34A-34C, 35, and 36-44 may enable users to quickly and efficiently apply a barrier material to a variety of different types of medical tools or instruments, including, for example, adult care stethoscopes, pediatric stethoscopes, cardiology stethoscopes, electronic stethoscopes, Emergency Medical Technicians (EMT)/Emergency Medical Services (EMS) stethoscopes, anesthesiologist stethoscopes, or any other type of medical scope. As described elsewhere herein, the barrier material may comprise, for example, any type of antimicrobial, antiviral, antipathogenic, or antibacterial material that can provide a sterile barrier between a patient and the tool or instrument to prevent a transmission or exchange of harmful particles or microbes. The barrier dispensers illustrated in FIGS. 26A-26B, 27A-27B, 28A-28B, 29A-29B, 30, 31, 32A-32B, 33A-33B, 34A-34C, 35, and 36-44 may be compatible with or adapted for use with any of the features or subsystems described elsewhere herein, including, for example, UV and/or UV-C lighting to sterilize or disinfect the barrier material.

Shield Designs

In some embodiments, the barrier material (also referred to herein as a "shield" or a "film") may comprise one or more layers. In some cases, the shield may comprise a single layer. In other cases, the shield may comprise two or more layers. In some cases, the shield may be sandwiched between two different layers of barrier material. The two different layers of barrier material may comprise a top layer and a bottom layer, with the shield disposed between the top layer and the bottom layer. In some embodiments, the shield and/or the one or more layers of the shield may comprise any glove or glove-like material, including, for example, polyurethane, vinyl, and/or nitrile. In some cases, the shield design may comprise three layers. In such cases, the shield may comprise a pouch on the front side of the shield and a half pouch on the other side of the shield.

Figure 45:
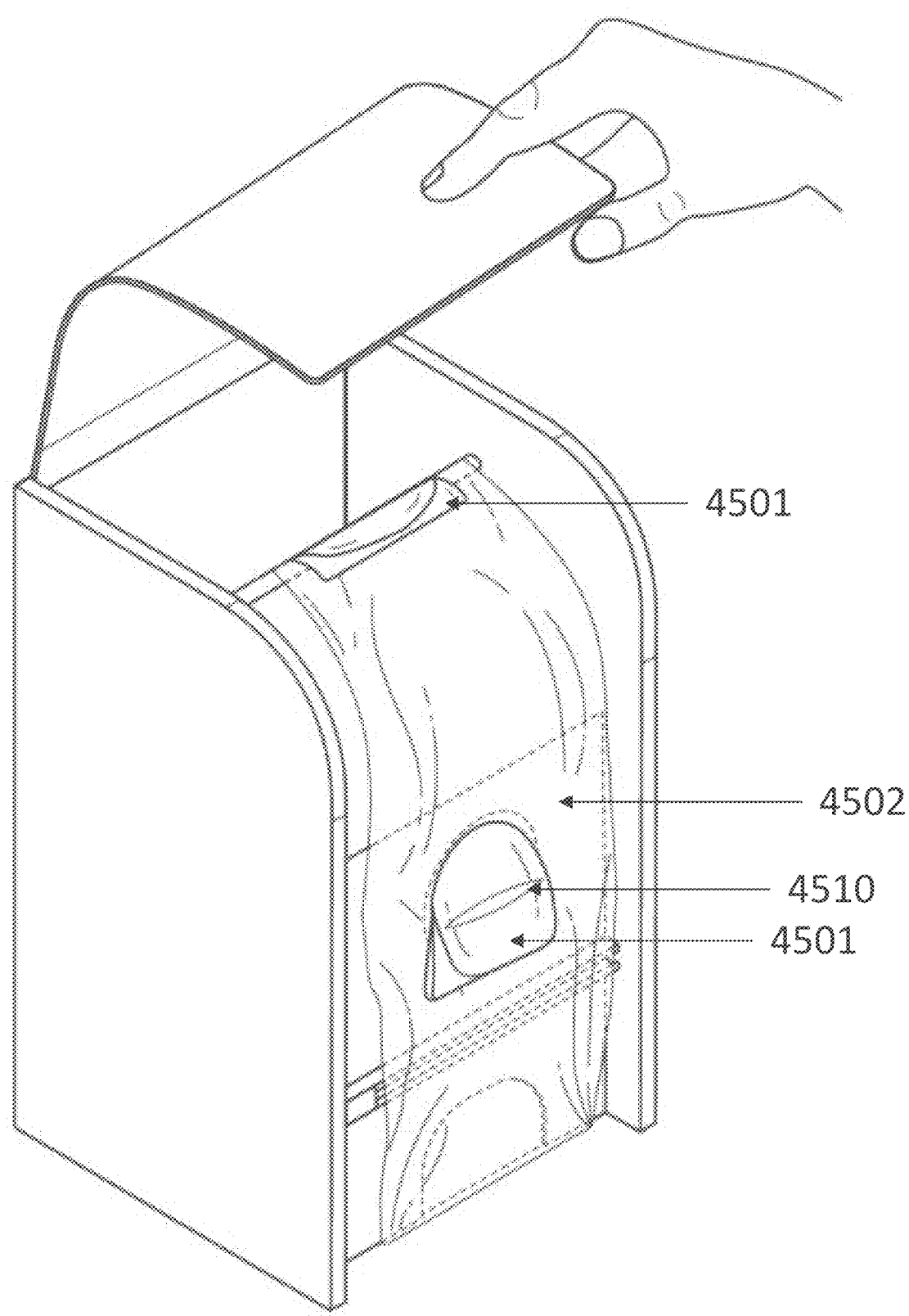
FIGS. 45-46 schematically illustrate an exemplary method for using a barrier dispenser to dispense a barrier material comprising a plurality of layers, in accordance with an embodiment.
Figure 46:
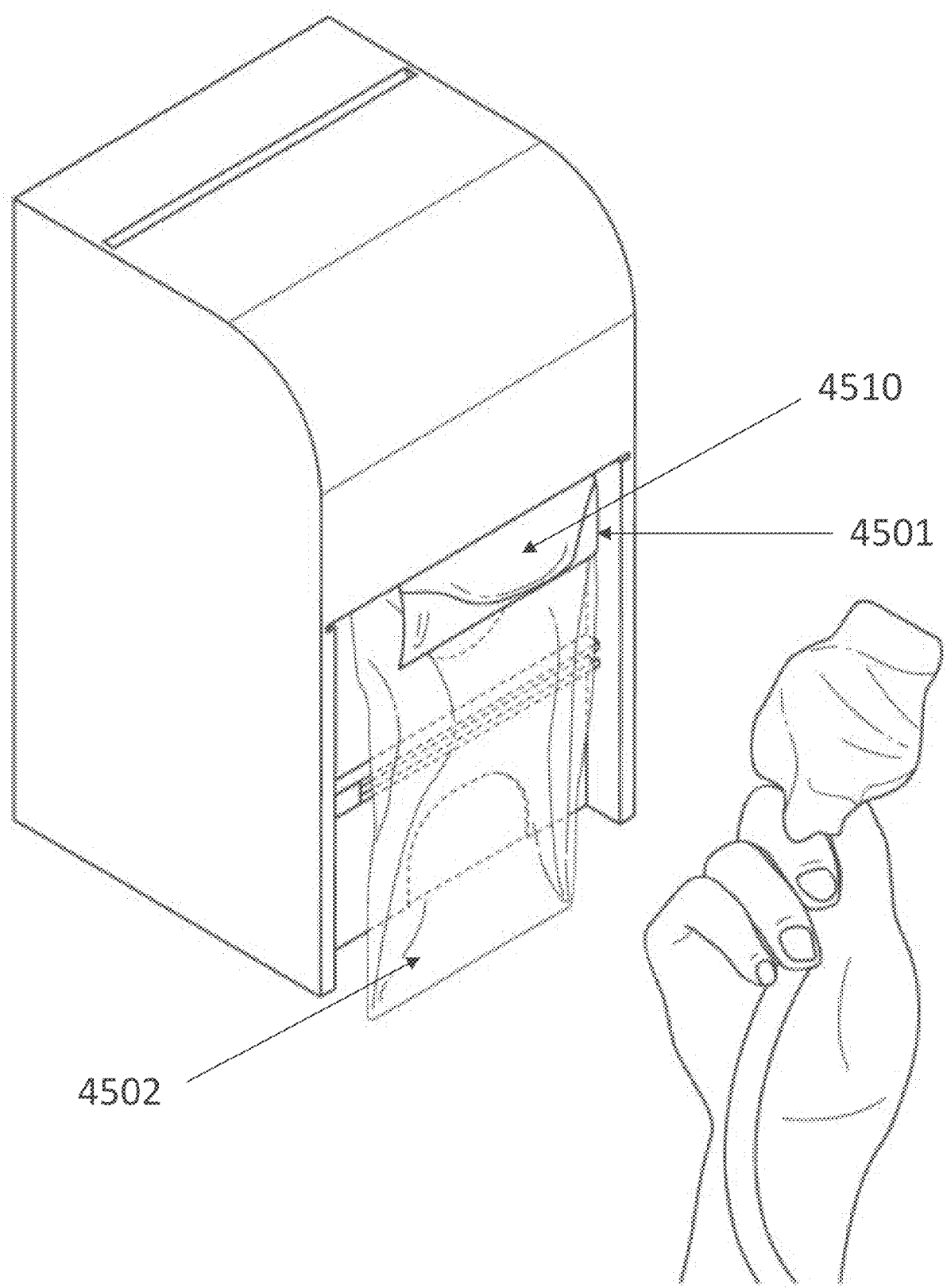

FIGS. 45-46 schematically illustrate dispensing a shield 4501 comprising multiple layers. Once a tool or an instrument (or a portion thereof) is inserted into a front pouch or pocket 4510 of the shield 4501 to cover a portion of the tool or instrument, the shield 4501 may be pulled off a paper material 4502 to which the shield 4501 is adhesively attached, thereby exposing a half pouch or flap on the back of the shield 4501. The half pouch or flap may then be pulled over the remaining portions of the tool or instrument to completely cover the tool or instrument. Once the shield 4501 is dispensed, a second shield 4501 may be pulled down from the barrier dispenser in order to wrap a second tool or instrument. The second shield 4501 may be adhesively attached to the paper material 4502. Pulling the paper material 4502 downwards may sequentially dispense a plurality of shields 4501. The plurality of shields 4501 may each comprise multiple layers. The plurality of shields 4501 may each comprise a front pocket or pouch 4510 configured to receive at least a portion of a tool or instrument. The tool or instrument may be placed within the front pocket or pouch 4510 such that the front pocket or pouch 4510 covers or envelops at least a portion of the tool or instrument. In some embodiments, the shield 4501 may or may not be transparent. In other embodiments, the shield 4501 may or may not be opaque. In some cases, the shield 4501 may be delivered on a transport layer. In some cases, the transport layer may or may not be transparent. In other cases, the transport layer may or may not be opaque. In some cases, the shield 4501 may be delivered in between two transport layers. In some cases, the two transport layers may or may not be transparent. In other cases, the two transport layers may or may not be opaque. The transport material constituting the transport layers may or may not be opaque or transparent.

FIGS. 47-54 illustrate various examples of shield designs that can be used with the barrier dispensers of the present disclosure. In any of the embodiments described herein, the shield may comprise one or more pouches or inner volumes. The one or more pouches or inner volumes may be enclosed or partially enclosed to provide a barrier between (i) a person, an object, or an external environment and (ii) a scope that is inserted into and/or at least partially covered or enveloped by the one or more pouches. The shield may comprise a cross-sectional shape. The cross-sectional shape may comprise, for example, a circle, an oval, an ellipse, a triangle, a square, a rectangle, a pentagon, a hexagon, a heptagon, an octagon, or any polygon comprising three or more sides. The cross-sectional shape may comprise one or more straight edges and/or one or more curved edges. In some cases, the cross-sectional shape may comprise a tear drop shape. In some cases, the cross-sectional shape may comprise a star shape or a heart shape. In other cases, the cross-sectional shape may comprise a repeating feature or pattern that extends periodically around an edge or perimeter of the cross-sectional shape. In some cases, the cross-sectional shape may comprise a cloud shape. In some cases, the cross-sectional shape may comprise a regular shape. In other cases, the cross-sectional shape may comprise an irregular or amorphous shape. In some cases, the shield may comprise one or more pouches having an inner volume in which at least a portion of a scope may be inserted. In some cases, the shield may comprise one or more portions having different sizes and/or shapes. For example, a first region or volume of the shield may comprise a first shape or a first dimension and a second region or volume of the shield may comprise a second shape or a second dimension. The first dimension and the second dimension may correspond to a length, a width, a height, or a thickness. The first dimension may be different than the second dimension. In some cases, the shield may comprise a shoe cover or hair net design. In such cases, the shield may comprise a surface that is sized and shaped to cover or envelope a head of a stethoscope, and an opening in which the head of the scope may be inserted. The opening may comprise an elastic material (e.g., an elastic band or wire) that is configured to tighten around a back portion of the head of the stethoscope to provide a secure and sealed barrier that is not easily removable. In some cases, the shield may comprise a two-dimensional sheet of material. In other cases, the shield may comprise a three-dimensional structure comprising any barrier material as described elsewhere herein. The three-dimensional structure may comprise an inner volume in which a head of a stethoscope is insertable.

Figure 48:
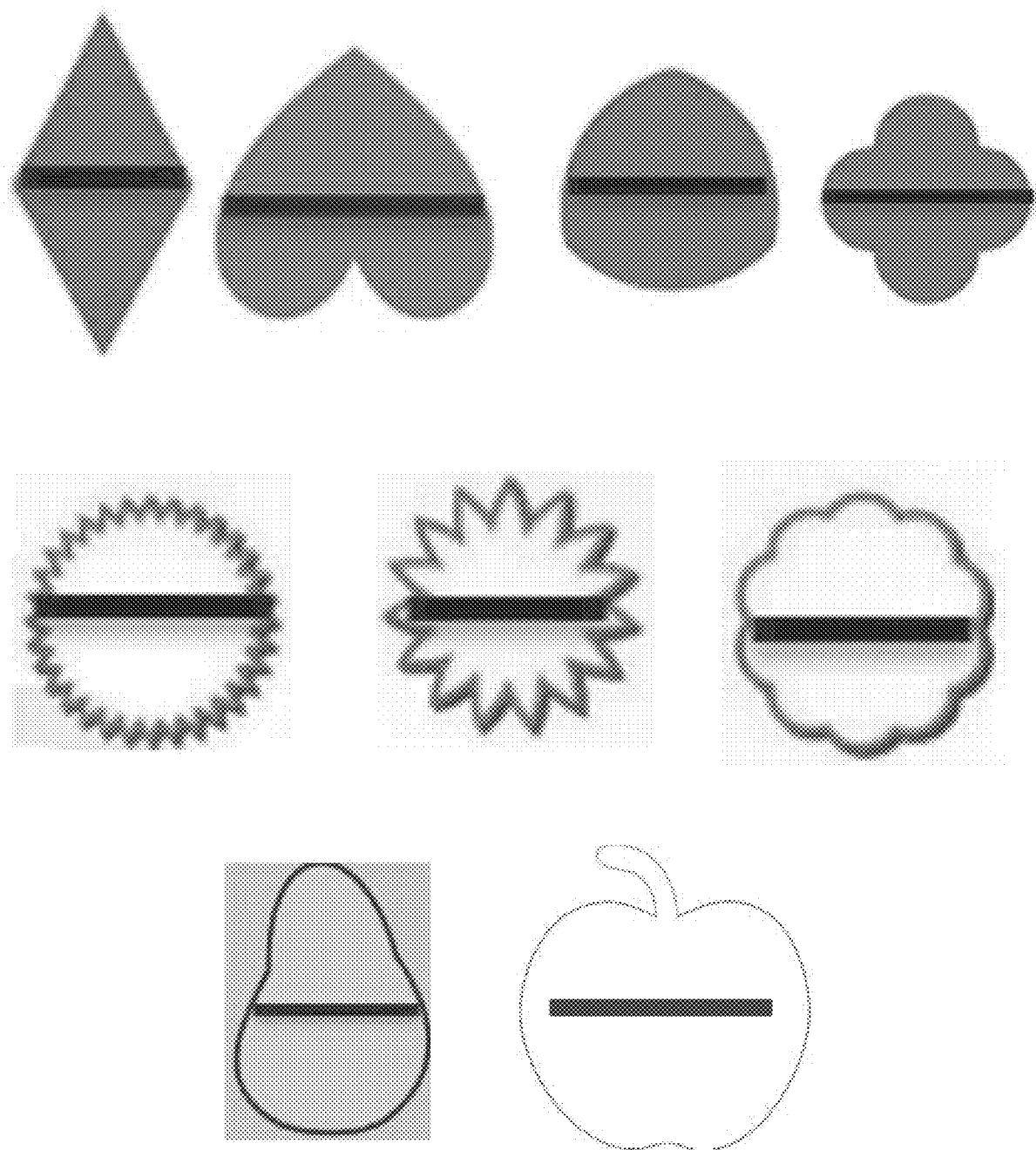
Figure 50:
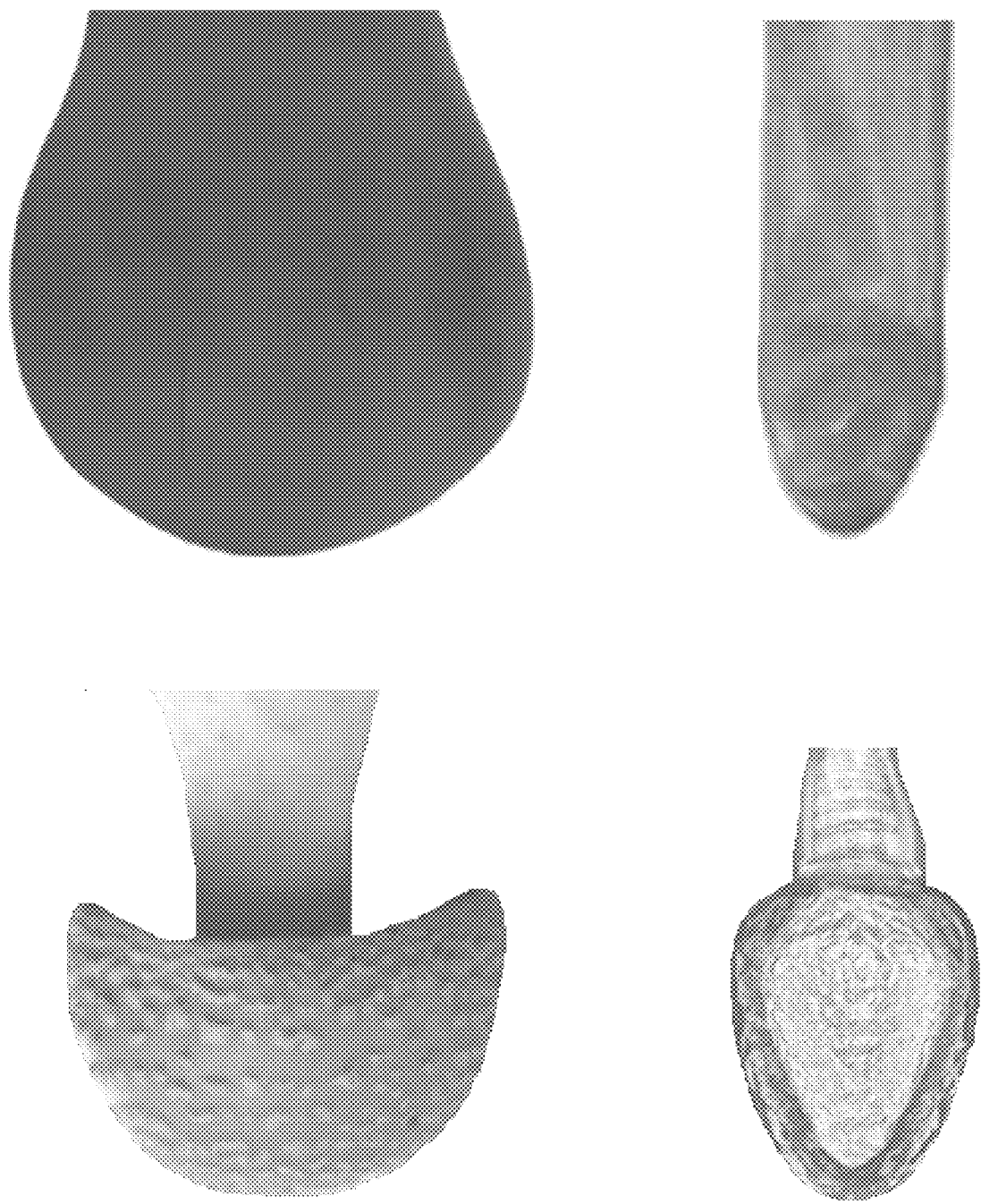

As shown in FIGS. 47-48, the shield may comprise an opening or a slit through which at least a portion of the scope may be inserted. The opening or slit may provide access to an inner volume or region of the shield. As described above, the shield may comprise a horizontal cross-sectional shape that is sized and shaped to receive and cover at least a portion of the scope. In some cases, the shield may comprise a pouch shape or configuration, as illustrated in FIGS. 49-50. The pouch shape or configuration may provide an inner volume or region in which the shield may be placed. The inner volume or region may partially encapsulate the scope or the head of the scope. In some cases, the inner volume or region may completely encapsulate or cover the scope or the head of the scope such that a plurality of surfaces of the scope is covered by the shield. The dimensions of the inner volume or region may be adjustable to cover multiple different types of scopes or other tools or instruments. In some cases, the pouch may comprise a symmetrical shape. In other cases, the pouch may not or need not comprise a symmetrical shape. In some embodiments, the shield may comprise an elongated shape having a length that is greater than a width or a height of the shield. In other embodiments, the shield may comprise a shape having a width or a height that is greater than a length of the shield. In any case, the shield may be sized and shaped to cover different types of instruments or tools having a range of different shapes and sizes.

Figure 51:
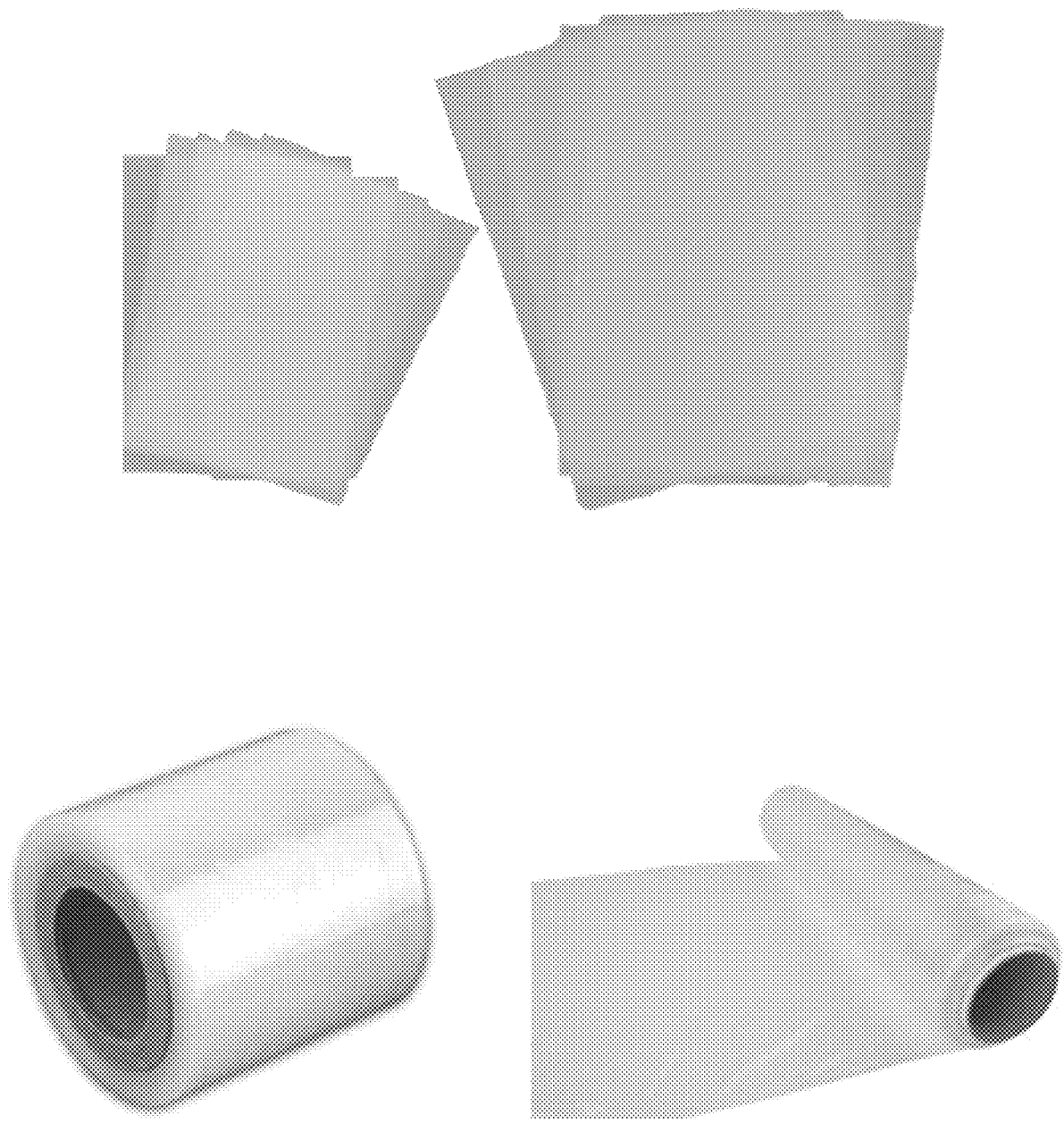

In some cases, the shield may comprise a single layer design. The single layer may comprise a two-dimensional film or barrier material that can be wrapped around a tool or an instrument, similar to a cling wrap off a roll or a sheet of barrier material. FIG. 51 schematically illustrates various examples of such single layer shield designs.

Figure 52:
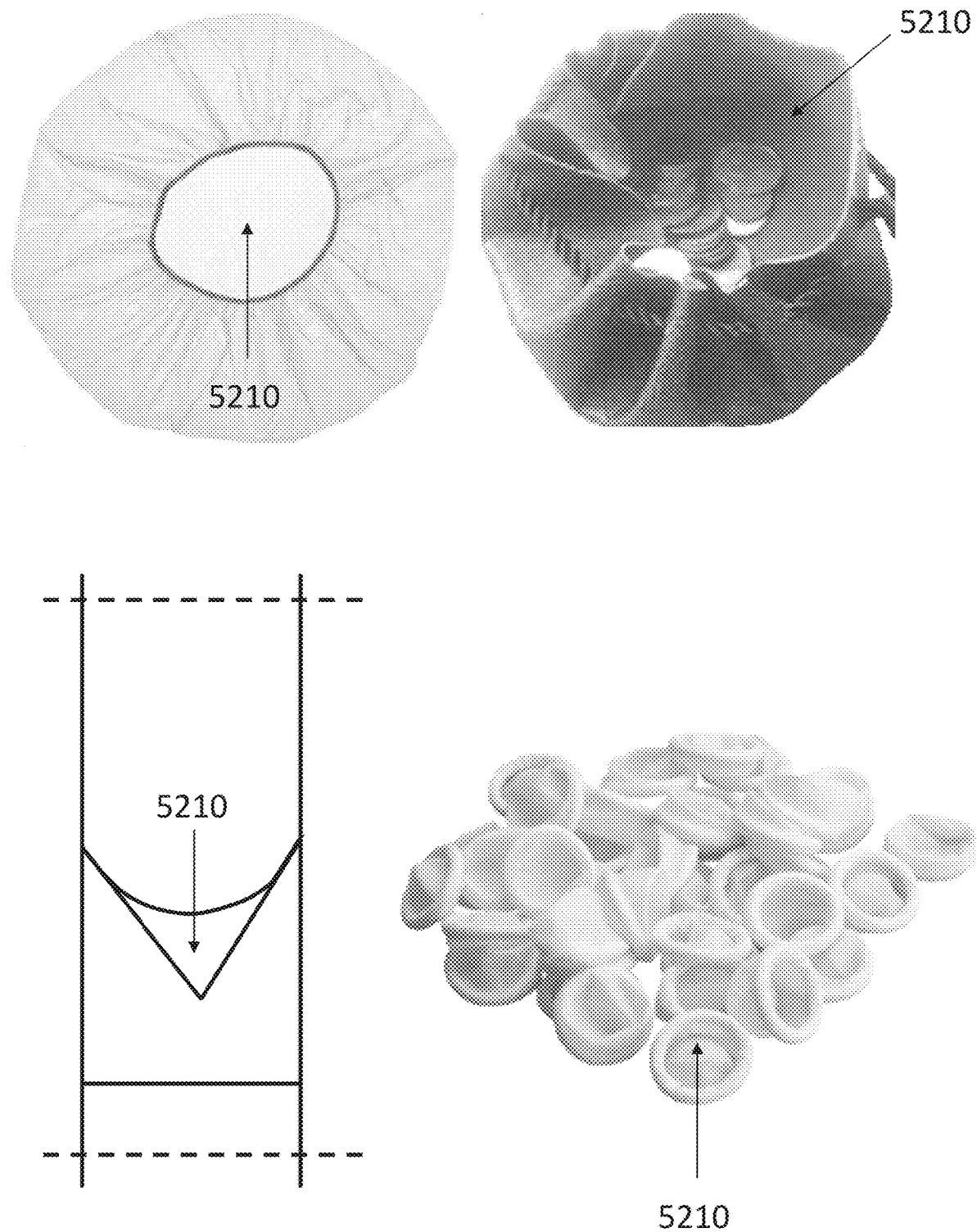
Figure 53:
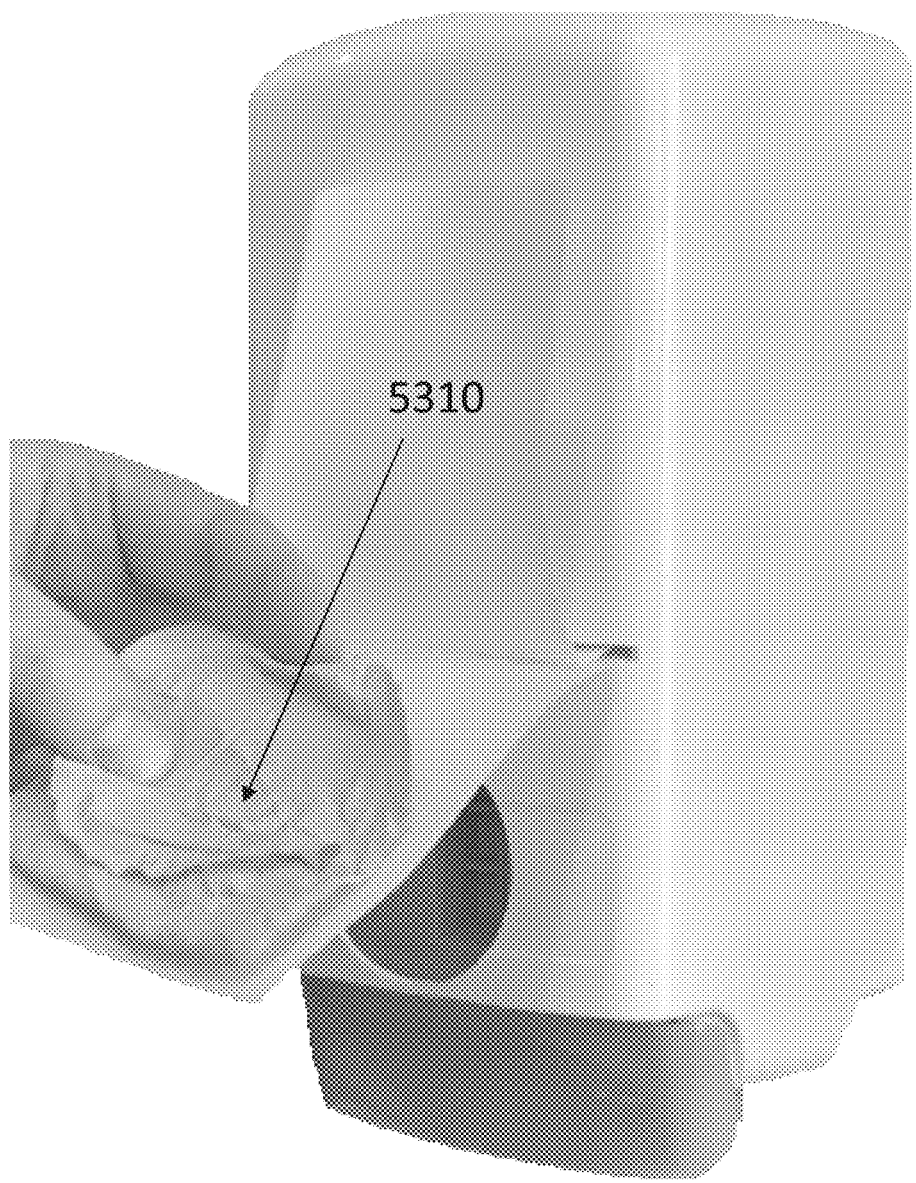

FIGS. 52-53 schematically illustrate various examples of shields comprising a two layer design. The two layer design may comprise a top layer and a bottom layer configured to cover a top portion, a bottom portion, and/or one or more side portions of the tool or instrument. In some cases, the two layer design may comprise a pouch shaped enclosure, similar to a shoe cover or a hair net. In some cases, the two layer design may comprise a rolled solution, similar to a finger cot or a condom. The rolled solution may be rolled over or around a tool or instrument to provide coverage for a top portion and/or a bottom portion of the tool or instrument. The rolled solution may also provide coverage for one or more side portions of the tool or instrument. In some cases, the two layer design may comprise an opening 5210 or a flap that provides access to an inner region or volume of the shield. The opening 5210 or flap may be disposed on any surface or region of the shield. FIG. 53 schematically illustrates another example of a two layer shield design. The shield may comprise a pouch 5310, flap, or pocket configured to receive at least a portion of the tool or instrument. The pouch 5310, flap, or pocket may extend from a lower portion of the shield to an upper portion of the shield. The pouch 5310, flap, or pocket may or may not extend across an entire height of the shield. In some cases, the two layer shield design may comprise an envelope configuration. In such cases, a stethoscope may be placed inside the envelope to cover a bottom portion of the scope, and a flap disposed above the opening of the shield may be used to cover the remaining portions of the stethoscope.

Figure 54:
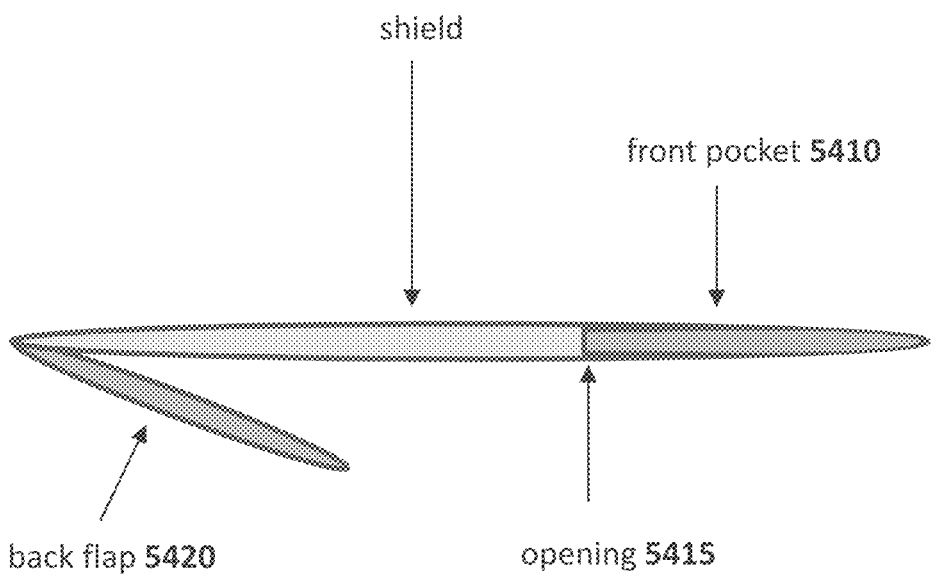

FIG. 54 schematically illustrates an example of a shield comprising a three layer design. The three layer design may comprise a front pouch 5410 or pocket comprising additional barrier material that is attached to a bottom portion of the front side of the shield. The additional barrier material may be substantially flat against a main body of the shield, and may provide an opening 5415 through which a portion of a scope may be inserted. The additional barrier material may be lifted relative to the main body of the shield to form the opening 5415 leading to an inner region or volume of the shield. The edges of the front pouch 5410 or pocket may be connected to or fused with the main body of the shield to form an enclosed inner region or volume configured to hold or cover at least a portion of the scope. The three layer shield design may further comprise a flap 5420 that is located on a back portion of the shield. The flap 5420 may comprise additional barrier material that may be reversed or pulled back and over any exposed regions of the scope that are not already covered by the front pouch 5410 or pocket. In some embodiments, the front pouch 5410 or pocket and the flap 5420 disposed on the back portion of the shield may be collectively used to completely cover the scope with a barrier material.

Figure 65A:
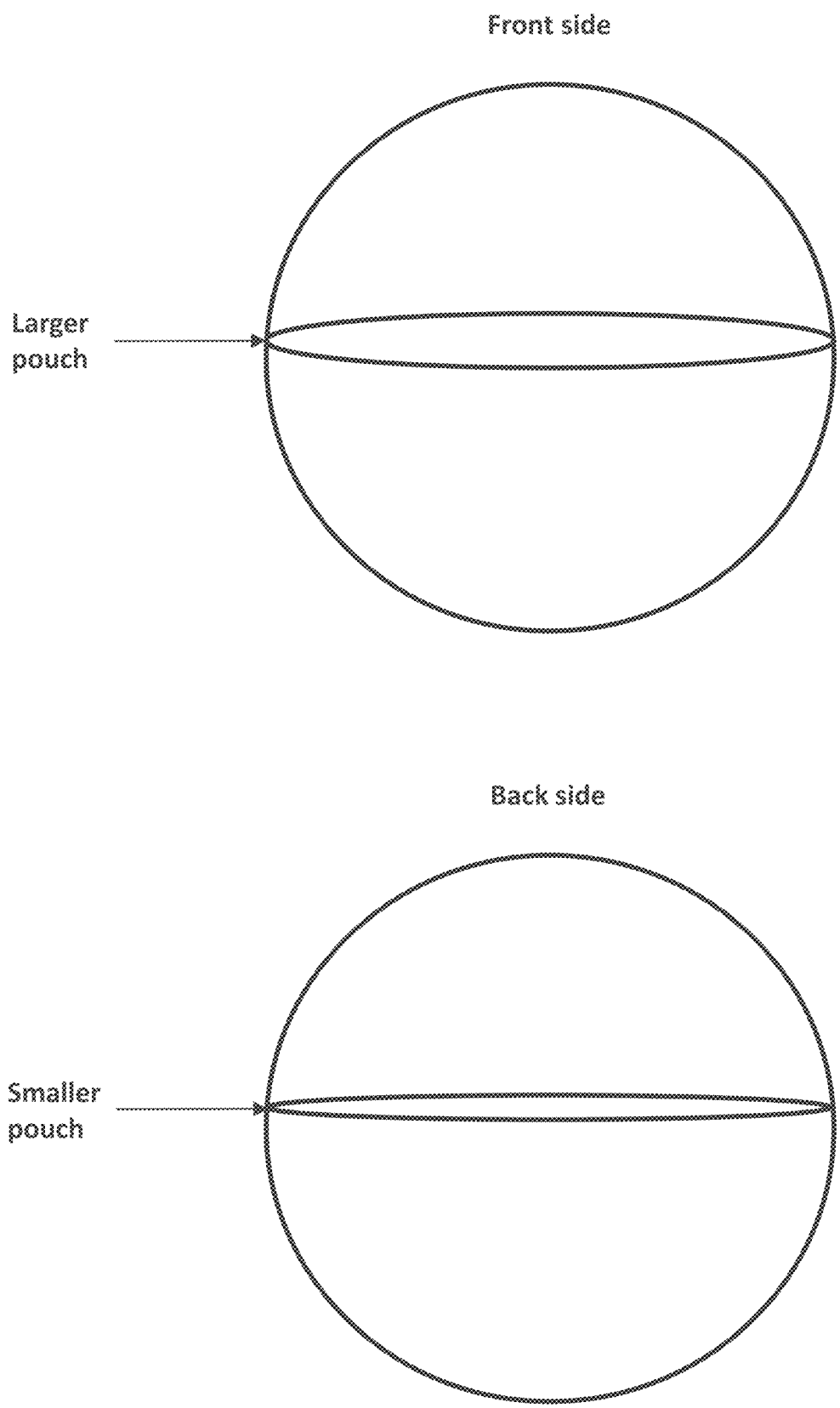
FIGS. 65A and 65B schematically illustrate additional examples of shield configurations that may be used compatibly with the barrier dispensers and dispense mechanisms of the present disclosure, in accordance with some embodiments.
Figure 65B:
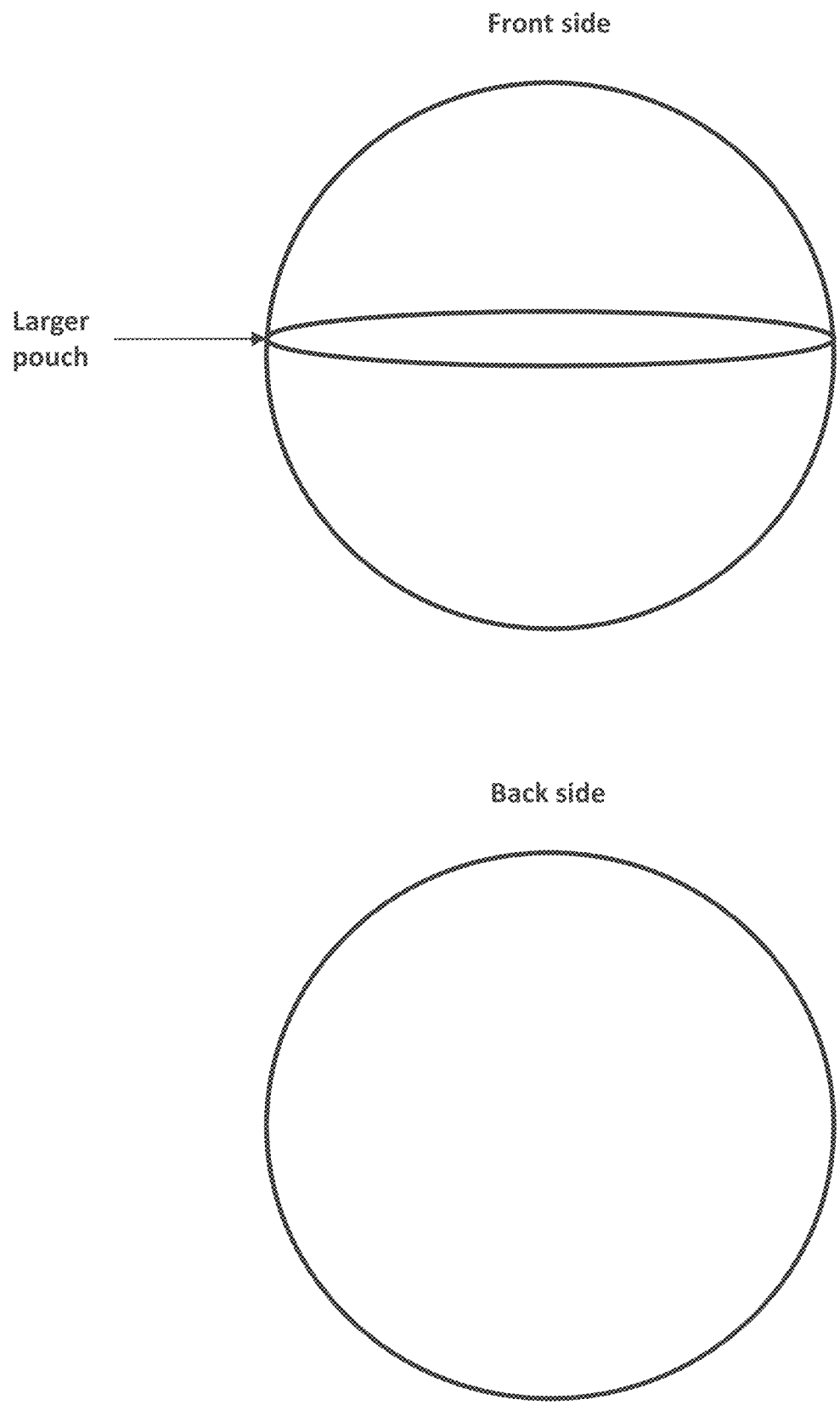

FIGS. 65A and 65B schematically illustrate additional non-limiting examples of shield designs which may be used with any of the barrier dispensers and/or dispense mechanisms disclosed herein. As shown in FIG. 65A, in some cases, the shield may comprise a front side with a first pouch and a back side with a second pouch. In some cases, the first pouch and the second pouch may comprise a same or similar size and/or shape. In other cases, the first pouch and the second pouch may comprise different sizes and/or shapes. For example, the first pouch may be larger than the second pouch. Alternatively, the second pouch may be larger than the first pouch. In any case, the first pouch and/or the second pouch may be configured to receive or envelope at least a portion of a surgical tool or instrument (e.g., a scope). As shown in FIG. 65B, in some cases, the shield may comprise a front side with a pouch and a back side that may not or need not comprise a pouch. In such cases, the pouch on the front side may be sized and/or shaped to receive or envelope at least a portion of a surgical tool or instrument. In some cases, the pouch on the front side may be sized and/or shaped to cover an entire head of a stethoscope.

Storage and Dispense Mechanisms

Figure 55:
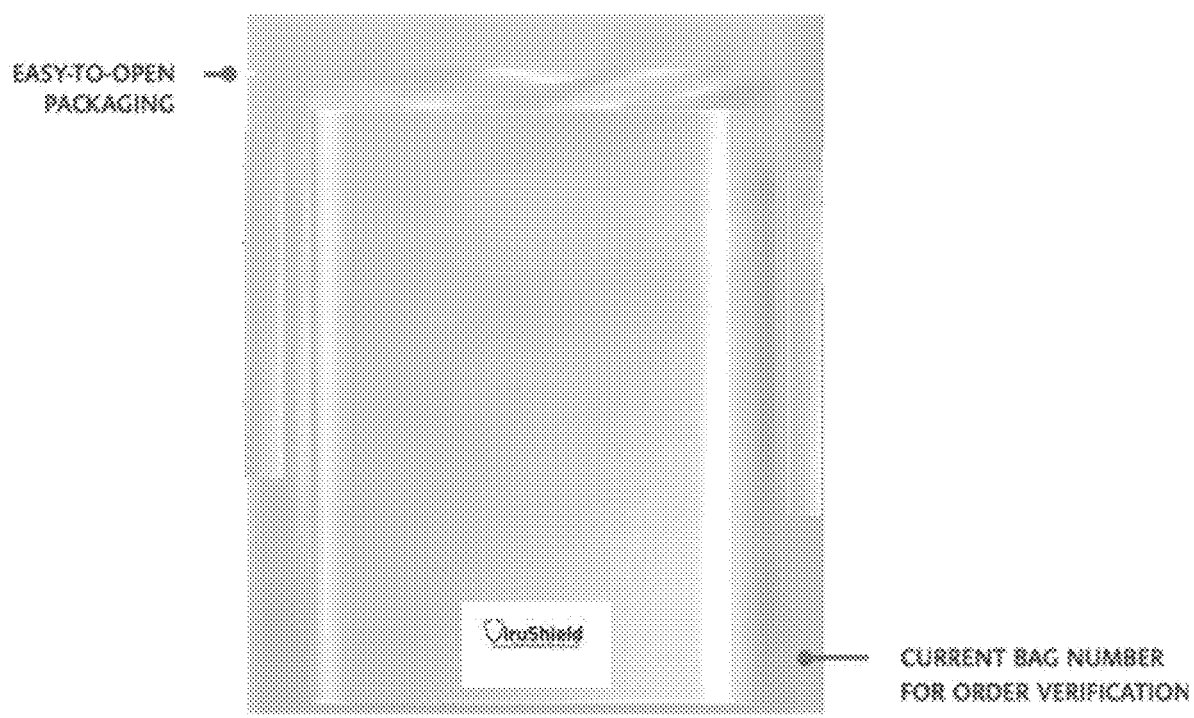
FIGS. 55-60 schematically illustrate various non-limiting examples of dispense mechanisms that can be used for the barrier dispensers of the present disclosure.
Figure 56:
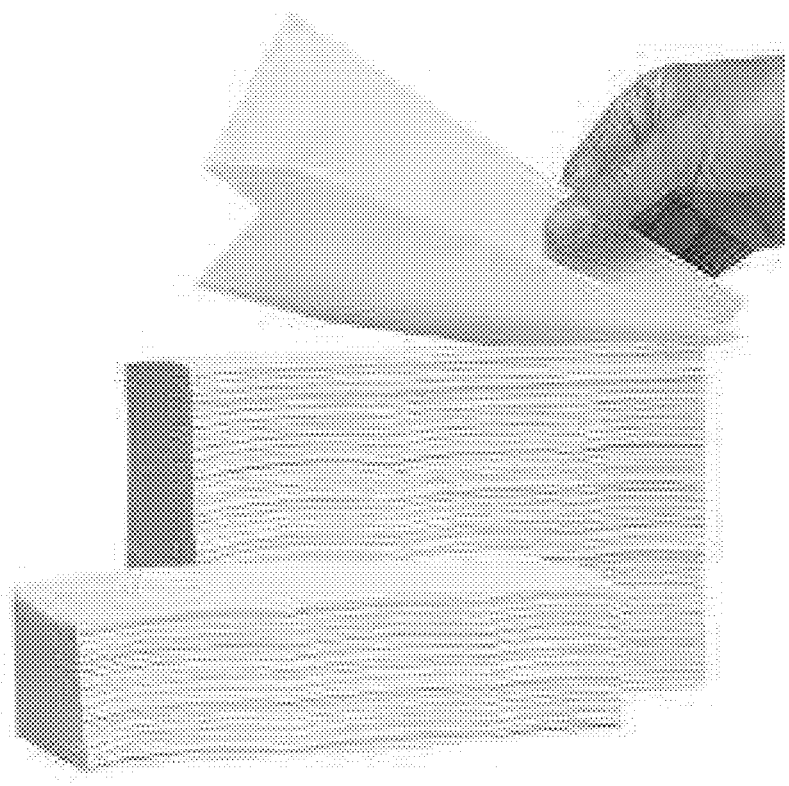

FIGS. 55-60 schematically illustrate various exemplary configurations for storing and dispensing multiple shields comprising a barrier material. As shown in FIG. 55, in some cases, the shields and barrier materials disclosed herein may be dispensed from a barrier dispenser when pulled in a downwards direction and/or an upwards direction, similar to a tissue dispenser. For instance, a user may pull a shield or barrier material out from the barrier dispenser. The shields or barrier materials may be organized in an interleafed fashion, as shown in FIG. 56. The barrier dispenser may comprise one or more openings through which the shields or barrier materials may be pulled out. The one or more openings may be located on a top portion, a bottom portion, or a side portion of the barrier dispenser. In some cases, the barrier dispenser may indicate a number of shields remaining and/or a number of shields already dispensed.

Figure 57:
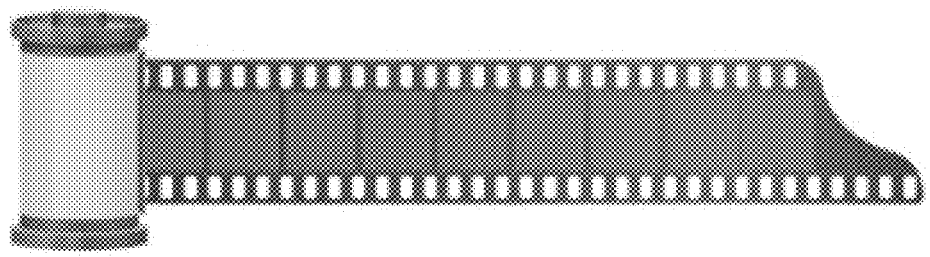

In some cases, the shields may be stored in a roll form and dispensed sequentially like a roll of camera film, as shown in FIG. 57. The shields may be pulled out by a user one by one and cut to size based on a size and/or a shape of a tool or instrument to be covered using the shield.

Figure 58:
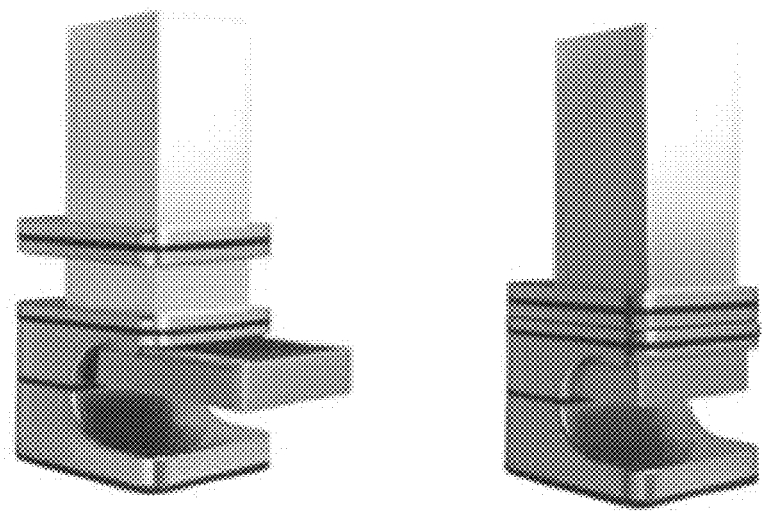

In some cases, the shields may be stored within a barrier dispenser comprising an enclosure and a movable component configured to translate forward and backwards to provide access to one or more shields stored within the enclosure of the barrier dispenser. An example of such a barrier dispensing mechanism is illustrated in FIG. 58. The movable component may permit access to the shields stored within the enclosure based on a user-provided input to dispense a shield. The user-provided input may comprise, for example, a physical input such as a push or a pulling force.

Figure 59:

In some cases, the barrier dispenser may comprise an enclosure or a box configured to hold a plurality of shields in a stacked configuration or a roll configuration, as shown in FIG. 59. The plurality of shields may be dispensed sequentially by a user when the user pulls out one or more shields from the enclosure or box. The plurality of shields may be attached to each other (e.g., along a perforated edge) and may be separated or cut by a user as desired.

Figure 60:
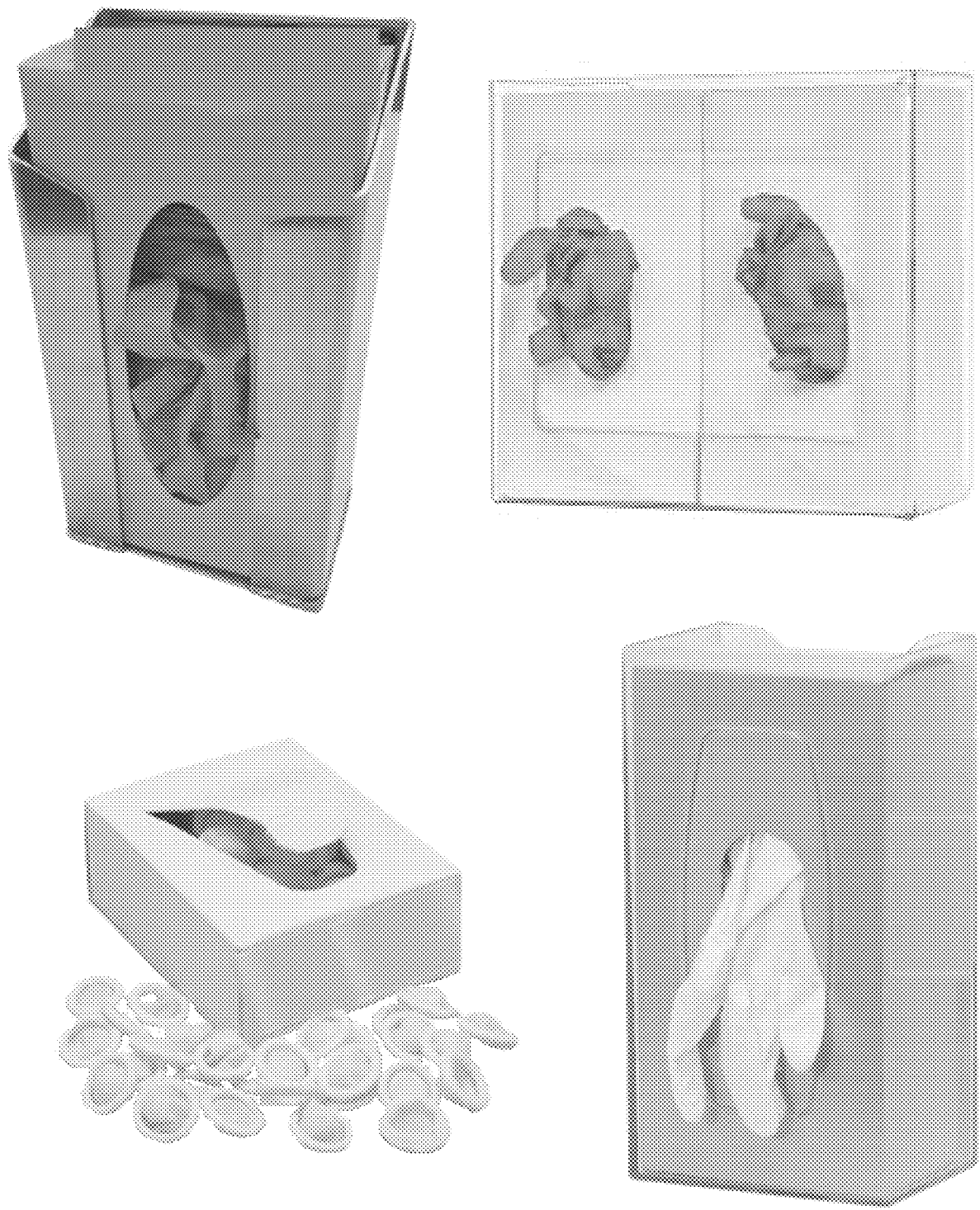
Figure 61:
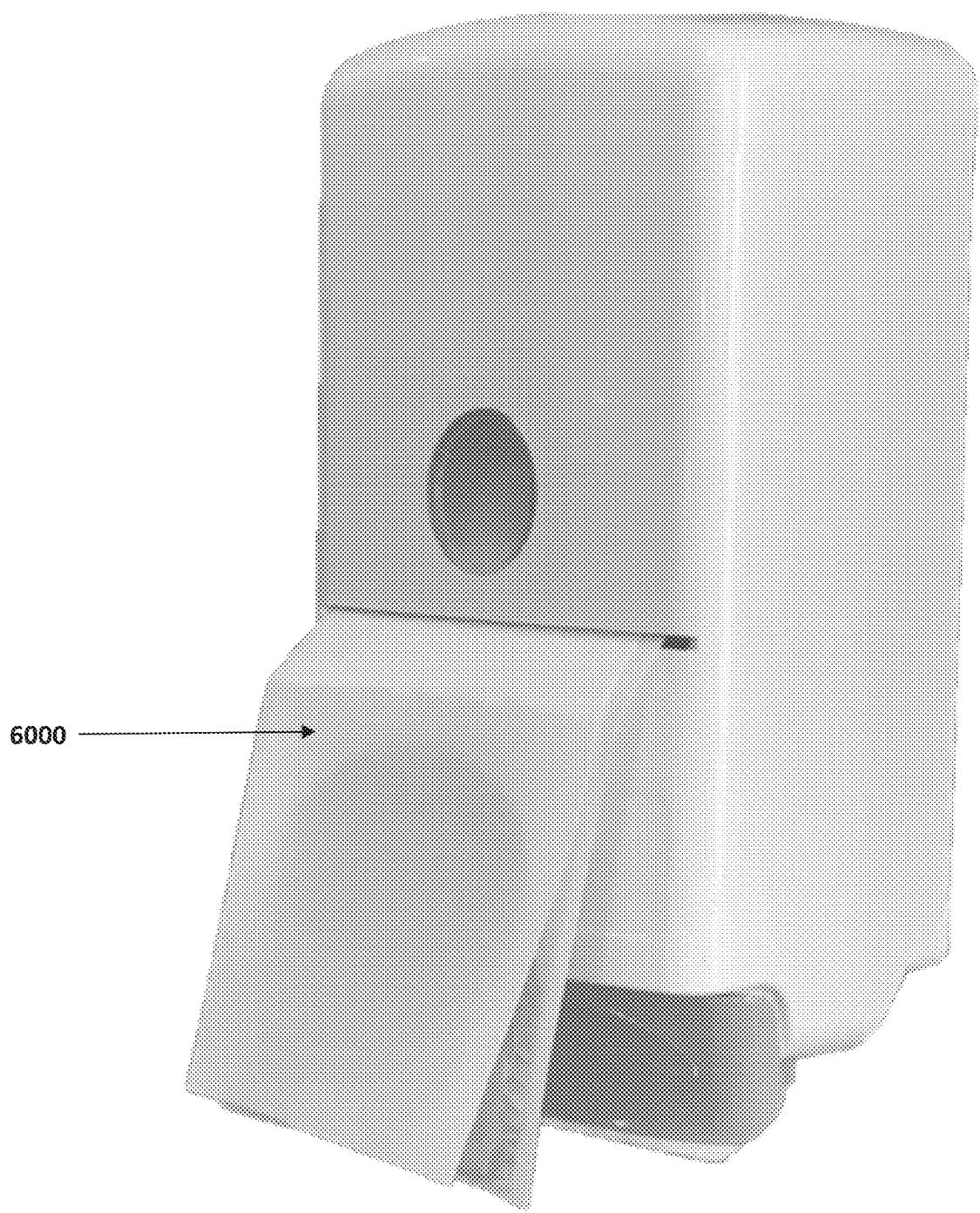
FIGS. 61-64 schematically illustrate dispensing a shield with aid of one or more shield delivery layers, in accordance with some embodiments.
Figure 62:
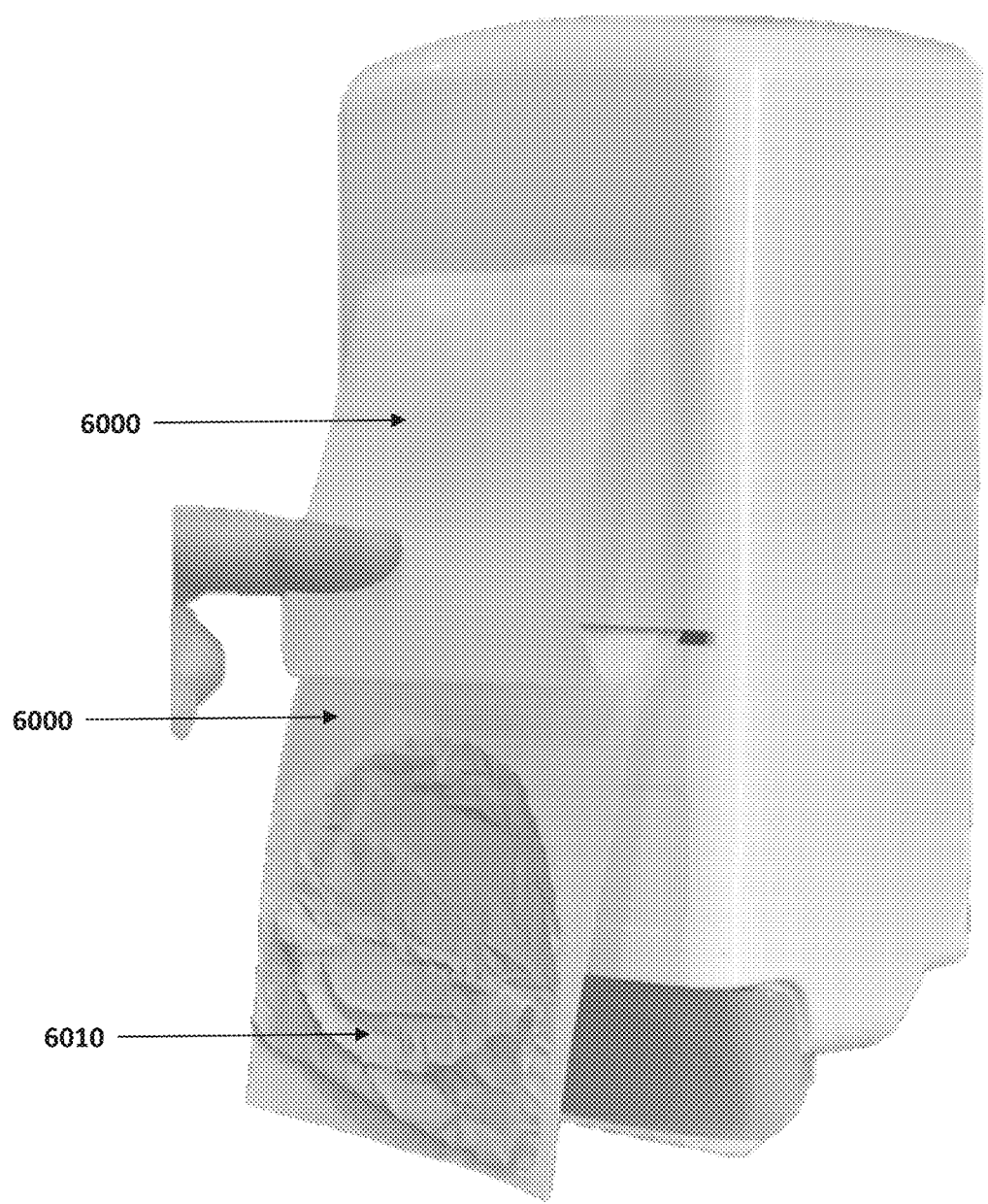
Figure 63:
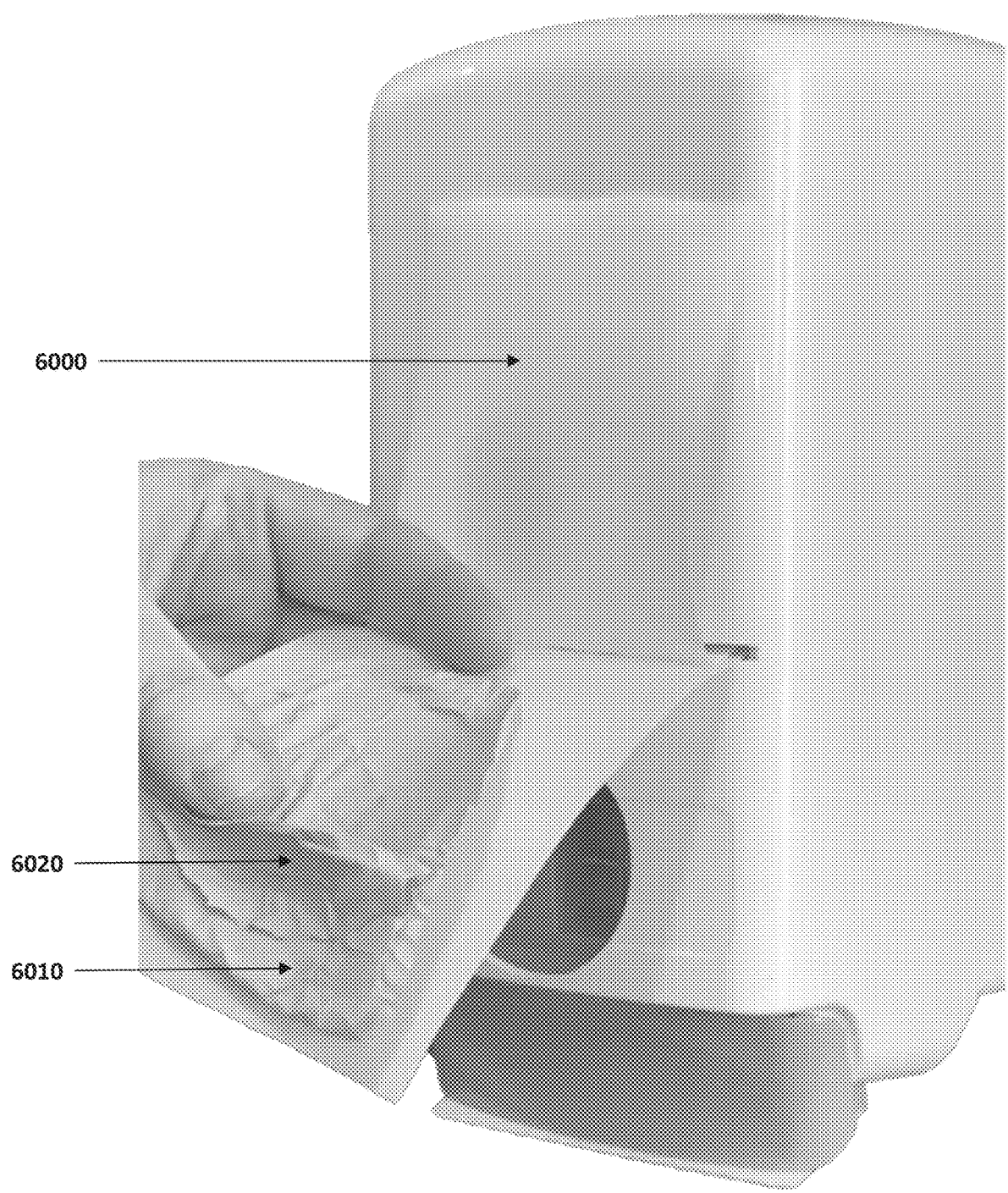
Figure 64:
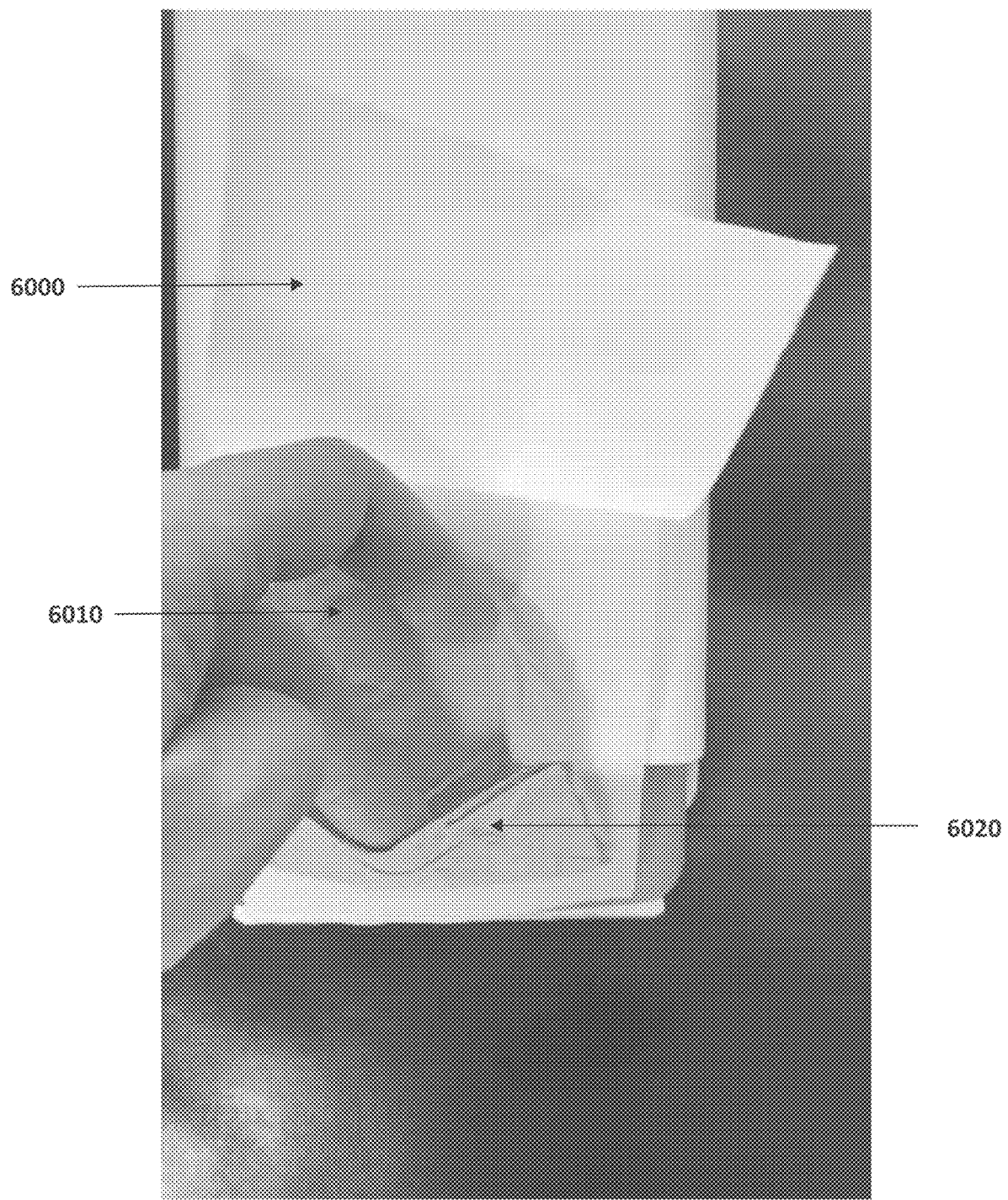

As shown in FIG. 60, in some cases the plurality of shields may be stored in an enclosure and dispensed from the enclosure one by one, similar to how disposable gloves may be dispensed. In such cases, the shields may be stacked on top of each other and pulled out one by one. The pulling motion to dispense the shields may cause another shield within the enclosure to protrude or extend outwards from the enclosure so that a user may continue to pull out additional shields as needed or desired. In such configurations, the shields may not or need not be attached to one another.

As described above, the shields may be arranged in a roll and dispensed by unrolling the shields, similar to how a film is dispensed. In some cases, the shields may be stacked on top of each other like gloves in a glove box. The shields may be removed one at a time from a housing containing the shields, or may be dispensed from a bottom of the housing and gravity fed. In other cases, the shields may be interleafed like a paper-based product. Alternatively, the shields may be stored in one or more sealed sachets or packets arranged in a roll configuration. In some cases, the shields may be stored in a plurality of sachets or packets that are attached together in series. The sachets or packets may comprise one or more single-use sachets or packets. The sachets or packets may be separated manually by a user (e.g., along a perforated line or edge between two or more sachets or packets).

FIGS. 61-64 schematically illustrate a shield being dispensed from a barrier dispenser with aid of one or more shield delivery layers. The shield may comprise any type of shield as described elsewhere herein, including shields having one or more layers. The barrier dispenser may comprise any type of barrier dispenser or dispensing mechanism as described elsewhere herein. In some cases, the shields of the present disclosure may be sandwiched between two shield delivery layers 6000. The shield delivery layers 6000 may comprise, for example, a paper material. The paper material may or may not comprise a light adhesive to secure the shields 6010 to the shield delivery layers 6000. The shield delivery layers 6000 may be configured to guide a removal or dispensing of the shields 6010 from the barrier dispenser. The shield delivery layers 6000 may provide a smooth surface that permits dispensing of the shields 6010 and prevents the shields 6010 from catching onto one or more portions of the dispenser (e.g., the opening of the dispenser), which can cause jamming or blockage of the barrier dispenser. The shield delivery layers 6000 may also help to flatten the shields 6010 so that a pouch 6020, pocket, or flap of the shields 6010 does not catch onto the dispenser and/or jam or block the outlet of the dispenser. The shield delivery layers 6000 may be transparent or opaque. See FIGS. 61-64 for a barrier dispenser capable of dispensing a top sheet and a bottom sheet with a shield in the center (i.e., between the top sheet and the bottom sheet).

Figure 66A:
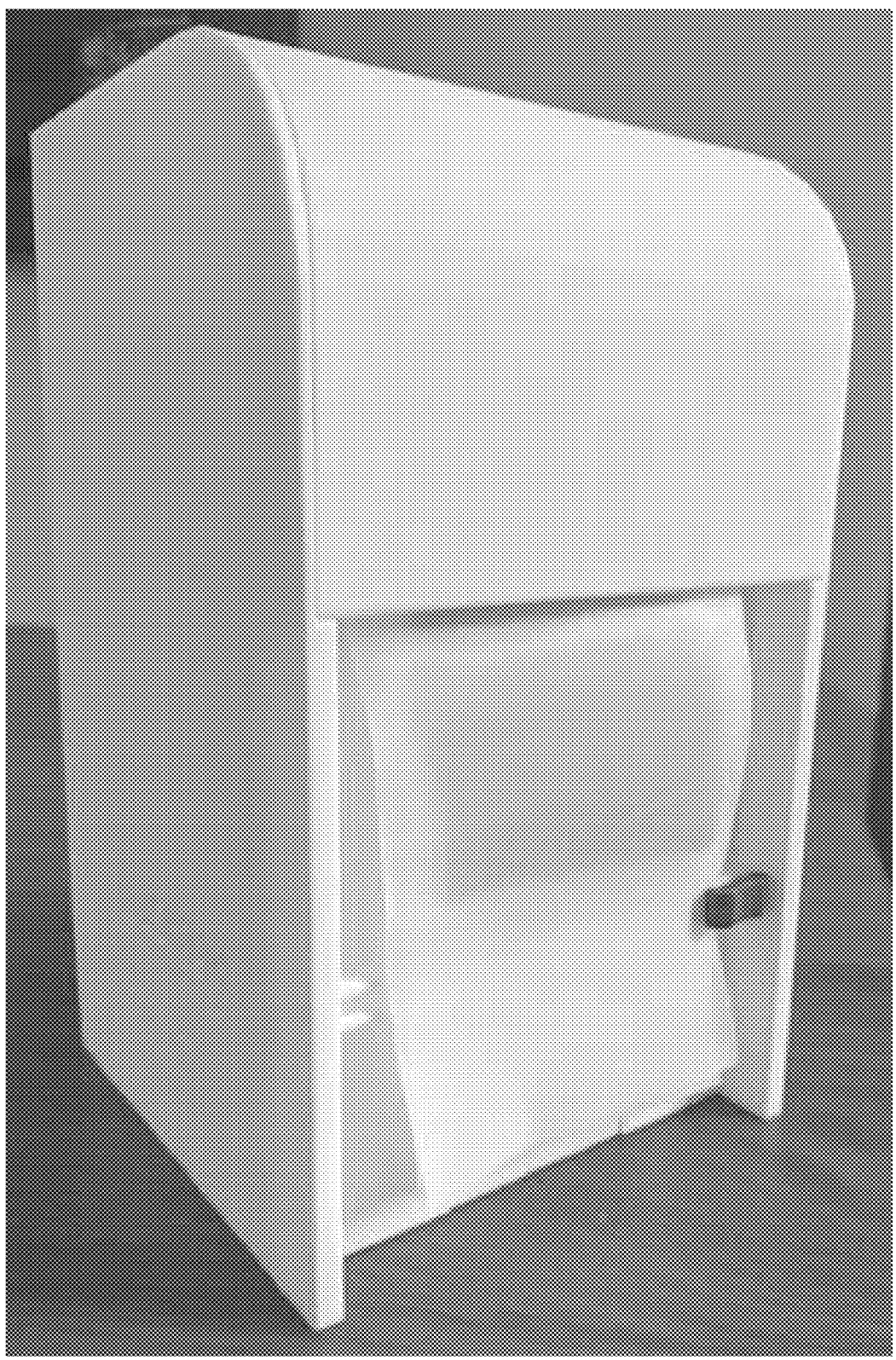
FIGS. 66A and 66B schematically illustrate additional examples of barrier dispensers that can dispense a barrier material positioned between a top layer and a bottom layer, in accordance with some embodiments.
Figure 66B:

FIGS. 66A and 66B schematically illustrate additional examples of barrier dispensers that can dispense a barrier material. The barrier material may be positioned between a top layer and a bottom layer. The top layer and/or the bottom layer may comprise a protective material.

Although certain embodiments and examples are provided in the foregoing description, the inventive subject matter extends beyond the specifically disclosed embodiments to other alternative embodiments and/or uses, and to modifications and equivalents thereof. For example, the apparatus and methods described herein can be applied to any type of object (other than stethoscopes) that requires a protective barrier to be applied in a reliable, quick and efficient manner. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

As used herein A and/or B encompasses one or more of A or B, and combinations thereof such as A and B. It will be understood that although the terms "first," "second," "third" etc. may be used herein to describe various elements, components, regions and/or sections, these elements, components, regions and/or sections should not be limited by these terms. These terms are merely used to distinguish one element, component, region or section from another element, component, region or section. Thus, a first element, component, region or section discussed below could be termed a second element, component, region or section without departing from the teachings of the present disclosure.

The terminology used herein is for the purpose of describing particular embodiments only and is not intended to limit the present disclosure. As used herein, the singular forms "a", "an" and "the" are intended to include the plural forms as well, unless the context clearly indicates otherwise. It will be further understood that the terms "comprises" and/or "comprising," or "includes" and/or "including," when used in this specification, specify the presence of stated features, regions, integers, steps, operations, elements and/or components, but do not preclude the presence or addition of one or more other features, regions, integers, steps, operations, elements, components and/or groups thereof.

Furthermore, relative terms, such as "lower" or "bottom" and "upper" or "top" may be used herein to describe one element's relationship to other elements as illustrated in the figures. It will be understood that relative terms are intended to encompass different orientations of the elements in addition to the orientation depicted in the figures. For example, if the element in one of the figures is turned over, elements described as being on the "lower" side of other elements would then be oriented on the "upper" side of the other elements. The exemplary term "lower" can, therefore, encompass both an orientation of "lower" and "upper," depending upon the particular orientation of the figure. Similarly, if the element in one of the figures were turned over, elements described as "below" or "beneath" other elements would then be oriented "above" the other elements. The exemplary terms "below" or "beneath" can, therefore, encompass both an orientation of above and below.

It should be understood from the foregoing that, while particular implementations have been illustrated and described, various modifications can be made thereto and are contemplated herein. It is also not intended that the invention be limited by the specific examples provided within the specification. While the invention has been described with reference to the aforementioned specification, the descriptions and illustrations of the preferable embodiments herein are not meant to be construed in a limiting sense. Furthermore, it shall be understood that all aspects of the invention are not limited to the specific depictions, configurations or relative proportions set forth herein which depend upon a variety of conditions and variables. Various modifications in form and detail of the described embodiments will be apparent to a person skilled in the art. It is therefore contemplated that the invention shall also cover any such modifications, variations and equivalents.

What is claimed is:

1. An apparatus comprising:
    a housing comprising a left side panel, a right-side panel, and a top panel, wherein the left side panel, the right-side panel, and the top panel each comprise one or more slots;
    a front panel that is insertable into the one or more slots of the left side panel and the right-side panel, wherein the front panel comprises one or more recessed regions sized and shaped to receive a portion of a medical tool or instrument;
    a source of a barrier material that is disposed within the housing and supported by the left side panel and the right-side panel; and
    a lid cover comprising a roller portion that is insertable into the one or more slots of the top panel, wherein the lid cover is pivotable relative to the housing when the roller portion is inserted into the one or more slots of the top panel,
    wherein the lid cover and the front panel form a gap through which a portion of the barrier material is permitted to extend when the barrier material is dispensed such that the extended portion of the barrier material hangs freely in proximity to the one or more recessed regions of the front panel.

2. The apparatus of claim 1, wherein at least one of the left side panel, the right-side panel, and the front panel comprises an optically transparent surface for viewing the source of the barrier material.

3. The apparatus of claim 1, wherein the housing further comprises a back panel comprising one or more holes for fastening the housing to a wall.

4. The apparatus of claim 1, wherein the source of the barrier material comprises a roll of the barrier material.

5. The apparatus of claim 1, wherein the barrier material comprises an antimicrobial, antiviral, antipathogenic, antiseptic, aseptic, or antibacterial material that is configured to reduce or eliminate contamination of the medical tool or instrument when applied on or around the medical tool or instrument, or any other material of a clean, non-sterile nature.

6. The apparatus of claim 1, wherein the medical tool or instrument comprises a scope.

7. The apparatus of claim 1, wherein the one or more recessed regions comprise two or more recessed regions having different sizes or shapes.

8. The apparatus of claim 1, further comprising a latch mechanism to secure the lid cover in a closed position.

9. The apparatus of claim 1, wherein the barrier material comprises a plurality of layers.

10. The apparatus of claim 1, wherein the barrier material is configured to envelope at least a portion of a tool or instrument such that a plurality of surfaces of the tool or instrument is covered by the barrier material.

11. The apparatus of claim 1, wherein the one or more recessed regions are adapted to allow the extended portion of the barrier material to be applied to the portion of the medical tool or instrument when the portion of the medical tool or instrument is placed within the one or more recessed regions.

12. The apparatus of claim 1, wherein the source of the barrier material is provided on a roller, wherein the roller is supported at each end by one of the left side panel and the right-side panel.

13. The apparatus of claim 1, wherein the front panel comprises a cutter for cutting and releasing the barrier material.

14. The apparatus of claim 13, wherein the cutter comprises a slidable cutting edge for cutting or releasing the barrier material when the barrier material is extended below the cutter.

15. The apparatus of claim 13, wherein the one or more recessed regions comprise a first recessed region disposed above the cutter and a second recessed region disposed below the cutter.

16. The apparatus of claim 1, wherein the lid cover comprises a curved profile that conforms to a shape or a profile of the left side panel and the right-side panel.

17. The apparatus of claim 16, wherein the left side panel and the right-side panel comprise one or more curved edges that conform to the curved profile of the lid cover.

18. The apparatus of claim 16, wherein the left side panel and the right-side panel each comprise a spacing sized and shaped to receive the lid cover when the lid cover is in a closed position such that the lid cover lies flush with one or more edges of the left side panel and the right-side panel.

19. The apparatus of claim 11, wherein the one or more recessed regions comprise (i) a first recessed region that is adapted to allow the extended portion of the barrier material to be applied to a first portion of the medical tool or instrument when the barrier material is extended by a first length and (ii) a second recessed region that is adapted to allow the extended portion of the barrier material to be applied to a second portion of the medical tool or instrument when the barrier material is extended by a second length.

20. The apparatus of claim 19, wherein the second length is greater than the first length.

21. The apparatus of claim 1, wherein the barrier material comprises one or more pouches, pockets, and/or flaps for receiving or covering at least a portion of a tool or instrument.

22. The apparatus of claim 21, wherein the barrier material comprises a pouch or pocket on a front side of the barrier material and a half pouch or flap on a back side of the barrier material.

\* \* \* \* \*

UNITED STATES PATENT AND TRADEMARK OFFICE
CERTIFICATE OF CORRECTION

| | |
|---|---|
| PATENT NO. | : 11,628,031 B2 |
| APPLICATION NO. | : 17/488057 |
| DATED | : April 18, 2023 |
| INVENTOR(S) | : Norman Tien-Yo Chien and Richard Alan Swartzbaugh |

It is certified that error appears in the above-identified patent and that said Letters Patent is hereby corrected as shown below:

On the Title Page

Item (71): "Henderson, NV" should read --Carlsbad, CA--

Item (73): "SANO CURATIO, LLC, Henderson, NV" should read --Sano Curatio, LLC, Carlsbad, CA--

Signed and Sealed this
Thirtieth Day of May, 2023

Katherine Kelly Vidal
*Director of the United States Patent and Trademark Office*